US012797391B2

(12) United States Patent
Pastor-Soler et al.

(10) Patent No.: US 12,797,391 B2
(45) Date of Patent: Nov. 17, 2026

(54) COMPOSITIONS CONTAINING AND THERAPIES USING BEMPEDOIC ACID AND TOLVAPTAN

(71) Applicant: Esperion Therapeutics, Inc., Ann Arbor, MI (US)

(72) Inventors: Núria M. Pastor-Soler, Altadena, CA (US); Kenneth R. Hallows, Altadena, CA (US); Stephen Lawrence Pinkosky, Plymouth, MI (US); William J. Sasiela, Bloomingdale, NJ (US); Ashley F. Hall, Camarillo, CA (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 318 days.

(21) Appl. No.: 18/565,762

(22) PCT Filed: Jun. 1, 2022

(86) PCT No.: PCT/US2022/031729
§ 371 (c)(1),
(2) Date: Nov. 30, 2023

(87) PCT Pub. No.: WO2022/256378
PCT Pub. Date: Dec. 8, 2022

(65) Prior Publication Data

US 2024/0366625 A1 Nov. 7, 2024

Related U.S. Application Data

(60) Provisional application No. 63/275,077, filed on Nov. 3, 2021, provisional application No. 63/195,843, filed on Jun. 2, 2021.

(51) Int. Cl.

| | |
|---|---|
| ***A61K 31/55*** | (2006.01) |
| ***A61K 31/20*** | (2006.01) |
| ***A61P 13/12*** | (2006.01) |

(52) U.S. Cl.
CPC .............. *A61K 31/55* (2013.01); *A61K 31/20* (2013.01); *A61P 13/12* (2018.01)

(58) Field of Classification Search
CPC .... A61K 2300/00; A61K 31/20; A61K 31/55; A61P 13/12
See application file for complete search history.

(56) References Cited

U.S. PATENT DOCUMENTS 3,152,148 A 10/1964 Easterly et al.
3,441,605 A 4/1969 Blake
(Continued)

FOREIGN PATENT DOCUMENTS

BR PI0318046 B1 3/2019
CA 2513660 A1 8/2004
(Continued)

OTHER PUBLICATIONS

Sans-Atxer Laia et al (International Journal of Nephrology and Renovascular disease, vol. vol. 11, Jan. 1, 2018 , pp. 41-51) (Year: 2018).*
(Continued)

*Primary Examiner* — Savitha M Rao
(74) *Attorney, Agent, or Firm* — Goodwin Procter LLP

(57) ABSTRACT

Provided herein are fixed-dose combinations comprising bempedoic acid and tolvaptan. Also provided herein are methods of treating autosomal dominant polycystic kidney disease (ADPKD) by administering a combination of bempedoic acid and tolvaptan. Further provided herein are methods of treating ADPKD by administering bempedoic acid.

20 Claims, 21 Drawing Sheets

(56) References Cited

U.S. PATENT DOCUMENTS 3,773,946 A 11/1973 Creger
3,930,024 A 12/1975 Creger
4,281,200 A 7/1981 Snoble
4,287,200 A 9/1981 Kawamatsu et al.
4,584,321 A 4/1986 Manghisi et al.
4,613,593 A 9/1986 Yamatsu et al.
4,634,119 A 1/1987 Pesthy
4,634,719 A 1/1987 Takaishi et al.
4,639,344 A 1/1987 Ueno et al.
4,689,344 A 8/1987 Bar-Tana
4,711,896 A 12/1987 Bar-Tana et al.
4,714,762 A 12/1987 Hoefle et al.
4,896,344 A 1/1990 Grady et al.
5,166,174 A 11/1992 Ueno et al.
5,225,439 A 7/1993 Ueno et al.
5,284,858 A 2/1994 Ueno et al.
5,380,709 A 1/1995 Ueno et al.
5,428,062 A 6/1995 Ueno et al.
5,502,198 A 3/1996 Picard et al.
5,504,073 A 4/1996 Homan
5,570,569 A 11/1996 Masuda
5,578,639 A 11/1996 Homan
5,631,365 A 5/1997 Rosenblum et al.
5,633,287 A 5/1997 Lee et al.
5,648,387 A 7/1997 Bisgaier et al.
5,750,569 A 5/1998 Bisgaier et al.
5,756,544 A 5/1998 Bisgaier et al.
5,783,600 A 7/1998 Bisgaier et al.
5,834,596 A 11/1998 Ageland et al.
5,886,034 A 3/1999 Ueno et al.
5,968,963 A 10/1999 Homan
5,981,595 A 11/1999 Picard et al.
6,004,925 A 12/1999 Dasseux et al.
6,017,905 A 1/2000 Roark et al.
6,037,323 A 3/2000 Dasseux et al.
6,093,719 A 7/2000 Bocan
6,093,744 A 7/2000 Lee et al.
6,124,309 A 9/2000 Bocan
6,143,755 A 11/2000 Bocan
6,207,822 B1 3/2001 Thiruvengadam et al.
6,362,236 B1 3/2002 Aviram et al.
RE37,721 E 5/2002 Rosenblum et al.
6,410,802 B1 6/2002 Dasseux et al.
6,459,003 B1 10/2002 Dasseux et al.
6,506,799 B1 1/2003 Dasseux
6,646,170 B2 11/2003 Dasseux et al.
6,673,780 B2 1/2004 Dasseux et al.
6,699,910 B2 3/2004 Dasseux et al.
6,703,422 B2 3/2004 Dasseux et al.
6,713,507 B2 3/2004 Dasseux et al.
6,790,953 B2 9/2004 Dasseux et al.
6,831,105 B2 12/2004 Dasseux
6,909,014 B2 6/2005 Dasseux et al.
7,053,080 B2 5/2006 Davis et al.
7,119,221 B2 10/2006 Dasseux et al.
7,192,940 B2 3/2007 Dasseux et al.
7,304,093 B2 12/2007 Dasseux et al.
7,335,689 B2 2/2008 Dasseux et al.
7,335,799 B2 2/2008 Dasseux et al.
7,405,226 B2 7/2008 Dasseux et al.
7,576,130 B2 8/2009 Dasseux et al.
7,705,177 B2 4/2010 Oniciu et al.
7,812,199 B2 10/2010 Dasseux et al.
7,838,554 B2 11/2010 Dasseux et al.
RE42,461 E 6/2011 Rosenblum et al.
8,067,466 B2 11/2011 Dasseux et al.
8,084,498 B2 12/2011 Dasseux et al.
8,153,690 B2 4/2012 Dasseux et al.
8,309,604 B2 11/2012 Dasseux et al.
8,497,301 B2 7/2013 Dasseux et al.
8,501,730 B2 8/2013 Torisawa et al.
8,623,915 B2 1/2014 Dasseux et al.
8,642,653 B2 2/2014 Dasseux et al.
8,975,300 B2 3/2015 Dasseux et al.
9,000,041 B2 4/2015 Dasseux et al.
9,006,290 B2 4/2015 Dasseux et al.
9,452,964 B2 9/2016 Dasseux et al.
9,624,152 B2 4/2017 Dasseux et al.
9,855,240 B2 1/2018 Zakrzewski
10,028,926 B2 7/2018 Bisgaier
10,047,028 B2 8/2018 Dasseux et al.
10,118,881 B2 11/2018 Dasseux et al.
10,905,694 B2 2/2021 Nakagawa et al.
10,912,751 B2 2/2021 Newton et al.
10,941,095 B2 3/2021 Dasseux et al.
11,116,739 B2 9/2021 Newton et al.
11,407,705 B2 8/2022 Copp et al.
11,613,511 B2 3/2023 Copp et al.
11,744,816 B2 9/2023 Newton et al.
11,760,714 B2 9/2023 Copp et al.
11,926,584 B2 3/2024 Copp et al.
11,987,548 B2 5/2024 Copp et al.
12,344,578 B2 7/2025 Copp et al.
12,398,087 B2 8/2025 Copp et al.
12,404,227 B2 9/2025 Copp et al.
2003/0180352 A1 9/2003 Patel et al.
2004/0209847 A1 10/2004 Dasseux et al.
2004/0214777 A1 10/2004 McGrath
2004/0214887 A1 10/2004 Dasseux et al.
2005/0043278 A1 2/2005 Dasseux et al.
2005/0119333 A1 6/2005 Dasseux
2005/0214887 A1 9/2005 Emori et al.
2007/0155704 A1 7/2007 Dasseux et al.
2007/0179120 A1 8/2007 Dasseux et al.
2008/0249166 A1 10/2008 Dasseux et al.
2009/0247489 A1 10/2009 Dasseux et al.
2010/0234342 A1 9/2010 Cifter et al.
2010/0291207 A1 11/2010 Gat et al.
2010/0297105 A1 11/2010 Geary et al.
2011/0262497 A1 10/2011 Injac et al.
2012/0129930 A1 5/2012 Dasseux et al.
2012/0135976 A1 5/2012 Kerc et al.
2012/0225908 A1 9/2012 Dasseux et al.
2013/0190354 A1 7/2013 Wen et al.
2013/0280176 A1 10/2013 Diezi et al.
2013/0302399 A1 11/2013 Feldhaus et al.
2014/0093564 A1 4/2014 Bradley et al.
2015/0005386 A1 1/2015 Bisgaier
2015/0344388 A1 12/2015 Dasseux et al.
2015/0344389 A1 12/2015 Dasseux et al.
2016/0058751 A1 3/2016 Vali et al.
2017/0349516 A1 12/2017 Dasseux et al.
2018/0064671 A1 3/2018 Newton et al.
2018/0078518 A1 3/2018 Newton et al.
2018/0214450 A1 * 8/2018 Kishore .................. A61P 13/12
2018/0338922 A1 11/2018 Abdelnasser et al.
2019/0008779 A1 1/2019 Oniciu et al.
2019/0084908 A1 3/2019 Dasseux et al.
2020/0117535 A1 4/2020 Deb et al.
2021/0139401 A1 5/2021 Copp et al.
2021/0139405 A1 5/2021 Copp et al.
2021/0322375 A1 10/2021 MacDougall et al.
2021/0322376 A1 10/2021 Lalwani
2021/0361605 A1 11/2021 Newton et al.
2021/0361618 A1 11/2021 Lalwani et al.
2022/0249380 A1 8/2022 Abdelnasser et al.
2022/0281795 A1 9/2022 Copp et al.
2022/0388937 A1 12/2022 Copp et al.
2023/0141635 A1 5/2023 Copp et al.
2023/0183160 A1 6/2023 Copp et al.
2023/0250043 A1 8/2023 Copp et al.
2024/0182396 A1 6/2024 Copp et al.
2024/0286987 A1 8/2024 Copp et al.
2024/0317665 A1 9/2024 Copp et al.
2025/0064767 A1 2/2025 Newton et al.
2025/0289793 A1 9/2025 Pinkosky et al.
2026/0146017 A1 5/2026 Copp et al.

FOREIGN PATENT DOCUMENTS

CN 107530308 A 1/2018
CN 107628975 A 1/2018
CN 109721486 A 5/2019
EP 0284108 A2 9/1988

(56) References Cited

FOREIGN PATENT DOCUMENTS

| | | | | |
|---|---|---|---|---|
| EP | 0824094 | A1 | 2/1998 | |
| EP | 0720599 | B1 | 5/1999 | |
| EP | 1047421 | A2 | 11/2000 | |
| EP | 1137634 | B1 | 6/2005 | |
| EP | 1597223 | A3 | 11/2005 | |
| EP | 2404890 | A1 | 1/2012 | |
| EP | 3270909 | A1 | 1/2018 | |
| EP | 3666750 | A1 | 6/2020 | |
| FR | 1545224 | A | 11/1968 | |
| GB | 1196594 | A | 7/1970 | |
| GB | 1196595 | A | 7/1970 | |
| GB | 1196596 | A | 7/1970 | |
| GB | 1196597 | A | 7/1970 | |
| GB | 1196598 | A | 7/1970 | |
| JP | 4931349 | B2 | 5/2012 | |
| JP | 2020117535 | A | 8/2020 | |
| MX | 349134 | B | 7/2017 | |
| WO | WO-1996/30328 | A1 | 10/1996 | |
| WO | WO-1998/30530 | A1 | 7/1998 | |
| WO | WO-1999/00116 | A2 | 1/1999 | |
| WO | WO-1999/900116 | | 1/1999 | |
| WO | WO-1999/26583 | A2 | 6/1999 | |
| WO | WO-2002030860 | A2 | 4/2002 | |
| WO | WO-2004/067489 | A2 | 8/2004 | |
| WO | WO-2005/062897 | A2 | 7/2005 | |
| WO | WO-2005/068412 | A1 | 7/2005 | |
| WO | WO-2007/058335 | A1 | 5/2007 | |
| WO | WO-2008/118883 | A1 | 10/2008 | |
| WO | WO-2012/040177 | A1 | 3/2012 | |
| WO | WO-2013/039969 | A1 | 3/2013 | |
| WO | WO-2014/099584 | A1 | 6/2014 | |
| WO | WO-2016/149191 | A1 | 9/2016 | |
| WO | WO-2016/149405 | A1 | 9/2016 | |
| WO | WO-2017023165 | A1 | 2/2017 | |
| WO | WO-2018/148417 | A1 | 8/2018 | |
| WO | WO-2018/218147 | A1 | 11/2018 | |
| WO | WO-2019161307 | A1 * | 8/2019 | ........... A61K 9/1652 |
| WO | WO-2020/041799 | A1 | 2/2020 | |
| WO | WO-2020/141419 | A2 | 7/2020 | |
| WO | WO-2020/257571 | A1 | 12/2020 | |
| WO | WO-2020/257573 | A1 | 12/2020 | |
| WO | WO-2021/110929 | A1 | 6/2021 | |
| WO | WO-2022/149161 | A1 | 7/2022 | |
| WO | WO-2025/014754 | A1 | 1/2025 | |

OTHER PUBLICATIONS

"Pharmaceutical substances. OFS. 1.1.0006.15", State Pharmacopoeia of the Russian Federation. XIII edition. Vol. I, entered into force on Jan. 1, 2016 (Russian Only).

AbMole Bioscience, ETC-1002 (Bempedoic acid), 2 pages, retrieved on Mar. 10, 2021 from <http://www.abmole.com/products/etc-1002.html>.

Ackerly, et al., 1995, "A novel approach to dual-acting thromboxane receptor antagonist/synthase inhibitors based on the link of 1.3-dioxane-thrombaxane receptor antagonists and -thromboxane synthase inhibitors", J. Med. Chem. 38:1608-1628.

Acton, et al., 1996, "Identification of scavenger receptor SR-B1 as high density lipoprotein receptor", Science. 271(5248):518-20.

Ahrens, et al., 1967, "A direct method for preparing pyridoxal and 4-pyridoxic acid (1)", J. Heterocyl. Chem. 4:625-26.

Ahuja, Chromatography & Separation Science (2003).

Akdim et al., "Efficacy and Safety of Mipomersen, an Antisense Inhibitor of Apolipoprotein B, in Hypercholesterolemic Subjects Receiving Stable Statin Therapy," J. Am. Coll. Cardiol., vol. 55, Apr. 13, 2010, pp. 1611-1618.

Akoh, Current management of autosomal dominant polycystic kidney disease, World J Nephrol 4(4): 468-479 (2015).

Alexander, K., et al., 1948, "4.4-Dichlorodibutyl ether and its derivatives from tetrahydrofuran", J. Am. Chem. Soc 70:1839-42.

Anonymous: "NCT01105598: A Multiple Ascending Dose Study of ETC-1002 in Subjects With Mild Dyslipidemia," Clinicaltrials.gov, Nov. 16, 2010, 5 pages, [Online] [Retrieved on Apr. 11, 2023].

Anonymous: "NCT01262638: A Study to Assess the Efficacy and Safety of ETC-1002 in Subjects With Elevated Blood Cholesterol and Either Normal or Elevated Triglycerides," Clinicaltrials.gov, Nov. 29, 2011, 5 pages, [Online] [Retrieved on Apr. 11, 2023].

Anonymous: "NCT01485146: A Multiple Ascending Dose Study of ETC-1002 in Healthy Subjects," Clinicaltrials.gov, Apr. 12, 2012, 4 pages, [Online] [Retrieved on Apr. 11, 2023].

Anonymous: "NCT01607294: A Single Center Study to Evaluate the Efficacy and Safety of ETC 1002 in Subjects With Type 2 Diabetes," Clinicaltrials.gov, Feb. 10, 2014, 4 pages, [Online] [Retrieved on Apr. 11, 2023].

Anonymous: "NCT01751984: A Study of the Efficacy and Safety of ETC-1002 in Subjects With Statin Intolerance," Clinicaltrials.gov, Aug. 19, 2013, 5 pages, [Online] [Retrieved on Apr. 11, 2023].

Anonymous: "NCT01779453: Study of the Safety, Pharmacokinetic Drug Interaction and Efficacy of ETC-1002 and Atorvastatin in Subjects With Hypercholesterolemia," Clinicaltrials.gov, Aug. 19, 2013, 5 pages, [Online] [Retrieved on Apr. 11, 2023].

Anonymous: "NCT01941836: Evaluation of ETC-1002, Ezetimibe, and the Combination in Hypercholesterolemic Patients," Clinicaltrials.gov, Nov. 14, 2013, 9 pages, [Online] [Retrieved on Apr. 11, 2023].

Anonymous: "NCT01941836: Evaluation of ETC-1002, Ezetimibe, and the Combination in Hypercholesterolemic Patients," Clinicaltrials. gov, Nov. 25, 2014, 8 pages, [Online] [Retrieved on Apr. 11, 2023].

Anonymous: "NCT02044627: Single Radiolabeled Dose Study to Investigate the Absorption, Metabolism and Excretion of [14C]-ETC-1002," Clinicaltrials.gov, Jan. 22, 2014, 4 pages, [Online] [Retrieved on Apr. 11, 2023].

Anonymous: "NCT02072161: Evaluation of ETC-1002 vs Placebo in Patients Receiving Ongoing Statin Therapy," Clinicaltrials.gov, Feb. 24, 2014, 6 pages, [Online] [Retrieved on Apr. 11, 2023].

Anonymous: "NCT02072161: Evaluation of ETC-1002 vs Placebo in Patients Receiving Ongoing Statin Therapy," Clinicaltrials.gov, Apr. 3, 2014, pp. 1-9, [Online] [Retrieved on Jun. 20, 2018] Retrieved from the Internet <URL:https://clinicaltrials.gov/ct2/history/NCT02072161?V_2=View#StudyPageTop>.

Anonymous: "NCT02178098: Evaluation of ETC-1002 in Patients With Hypercholesterolemia and Hypertension," Clinicaltrials.gov, Jun. 26, 2014, 7 pages, [Online] [Retrieved on Apr. 11, 2023].

Anonymous: "NCT02659397: A Study Of Pharmacokinetics, Pharmacodynamics And Safety Of Adding ETC-1002 To Atorvastatin 80 mg," Clinicaltrials. gov, Mar. 29, 2019, 6 pages, [Online] [Retrieved on Apr. 11, 2023].

Anonymous: "NCT02666664: Evaluation of Long-Term Safety and Tolerability of ETC-1002 in High-Risk Patients With Hyperlipidemia and High CV Risk (CLEAR Harmony)," Clinicaltrials.gov, May 11, 2020, 10 pages, [Online] [Retrieved on Apr. 11, 2023].

Anonymous: "NCT02988115: Evaluation of the Efficacy and Safety of Bempedoic Acid (ETC- 1002) in Patients With Hyperlipidemia and Statin Intolerant (CLEAR Serenity)," Clinicaltrials.gov, Apr. 3, 2020, 6 pages, [Online] [Retrieved on Apr. 11, 2023].

Anonymous: "NCT02991118: Evaluation of Long-Term Efficacy of Bempedoic Acid (ETC-1002) in Patients With Hyperlipidemia at High Cardiovascular Risk (CLEAR Wisdom)," Clinicaltrials.gov, Apr. 27, 2020, 9 pages, [Online] [Retrieved on Apr. 11, 2023].

Anonymous: "NCT02993406: Evaluation of Major Cardiovascular Events in Patients With, or at High Risk for, Cardiovascular Disease Who Are Statin Intolerant Treated With Bempedoic Acid (ETC-1002) or Placebo (CLEAR Outcomes)," Clinicaltrials.gov, Jan. 3, 2024.

Anonymous: "NCT02993406: Evaluation of Major Cardiovascular Events in Patients With, or at High Risk for, Cardiovascular Disease Who Are Statin Intolerant Treated With Bempedoic Acid (ETC-1002) or Placebo (CLEAR Outcomes)," Clinicaltrials.gov, Dec 7, 2022, 5 pages, [Online] [Retrieved on Apr. 11, 2023].

Anonymous: "NCT03001076: Evaluation of the Efficacy and Safety of Bempedoic Acid (ETC-1002) as Add-on to Ezetimibe Therapy in Patients With Elevated Ldl-C (Clear Tranquility)," Clinicaltrials. gov, May 11, 2020, 8 pages, [Online] [Retrieved on Apr. 11, 2023].

Anonymous: "NCT03051100: Evaluation of the Efficacy and Safety of Bempedoic Acid (ETC-1002) 180mg, Ezetimibe 10mg, and

(56) References Cited

OTHER PUBLICATIONS

Atorvastatin 20 mg Triplet Therapy in Patients With Elevated LDL-C," Clinicaltrials. gov, Apr. 3, 2020, 6 pages, [Online] [Retrieved on Apr. 11, 2023].

Anonymous: "NCT03067441: Assessment of the Long-Term Safety and Efficacy of Bempedoic Acid (CLEAR Harmony OLE)," Clinicaltrials.gov, Mar. 1, 2021, 7 pages, [Online] [Retrieved on Apr. 11, 2023].

Anonymous: "NCT03193047: Evaluation of the Efficacy and Safety of Bempedoic Acid (ETC- 1002) 180mg When Added to PCSK9 Inhibitor Therapy," Clinicaltrials.gov, Apr. 3, 2020, 7 pages, [Online] [Retrieved on Apr. 11, 2023].

Anonymous: "NCT03337308: A Study Evaluating the Safety and Efficacy of Bempedoic Acid Plus Ezetimibe Fixed-Dose Combination Compared to Bempedoic Acid, Ezetimibe, and Placebo in Patients Treated With Maximally Tolerated Statin Therapy," Clinicaltrials.gov, Apr. 8, 2020, 8 pages, [Online] [Retrieved on Apr. 11, 2023].

Anonymous: "NCT03531905: Bempedoic Acid + Ezetimibe Fixed-Dose Combination (FDC) Study in Patients With Type 2 Diabetes and Elevated LDL-C," Clinicaltrials. gov, Apr. 9, 2020, 8 pages, [Online] [Retrieved on Apr. 11, 2023].

Anonymous: "NCT04579367: Treatment With Bempedoic Acid and/or Its Fixed-dose Combination With Ezetimibe in Primary Hypercholesterolemia or Mixed Dyslipidemia (MILOS)," Clinicaltrials. gov, Jan. 31, 2023, 6 pages, [Online] [Retrieved on Apr. 11, 2023].

Anonymous: "NCT04784442: A Dose-finding Trial of ETC-1002(Bempedoic Acid) in Patients With Hypercholesterolemia," Clinicaltrials.gov, Aug. 22, 2022, 5 pages, [Online] [Retrieved on Apr. 11, 20231.

Anonymous: "NCT05103254: Bempedoic Acid Pregnancy Surveillance Program," Clinicaltrials.gov, Feb. 21, 2023, 5 pages, [Online] [Retrieved on Apr. 11, 2023].

Anonymous: "NCT05263778: Cholesterol Lowering Via Bempedoic Acid/Ezetimibe, an ACL-Inhibiting Regimen in Acute Coronary Syndrome Study," Clinicaltrials.gov, Mar. 3, 2022, 6 pages, [Online] [Retrieved on Apr. 11, 2023].

Anonymous: "NCT05488431: Cholesterol and Inflammation Lowering Via Bempedoic Acid, an ACL-inhibiting Regimen in HIV Trial (Clear Hiv Trial)," Clinicaltrials.gov, Jan. 9, 2023, 8 pages, [Online] [Retrieved on Apr. 11, 2023].

Anonymous: "NCT05546398: Survey Followed by a Retrospective Chart Review to Describe the Key Factors Leading to Physician's Decision to Treat Patients at High and Very High Cardiovascular Risk With hypercholesterolemia or Mixed Dyslipidemia With NUSTENDI®, "Clinicaltrials.gov, Dec 1, 2022, 6 pages, [Online] [Retrieved on Apr. 11, 2023].

Anonymous: "NCT05683340: A Confirmatory Trial of ETC-1002 in Patients With Hyper-LDL Cholesterolemia," Clinicaltrials.gov, Mar. 23, 2023, 4 pages, [Online] [Retrieved on Apr. 11, 2023].

Anonymous: "NCT05687071: A Long-term Trial of ETC-1002 in Patients With Hyper-LDL Cholesterolemia," Clinicaltrials.gov, Mar. 23, 2023, 4 pages, [Online] [Retrieved on Apr. 11, 2023].

Anonymous: "NCT05694260: A Phase 2 Clinical Study in Children With HeFH Aged 6 to 17 Treated Once Daily With Bempedoic Acid Oral Dosing (CLEAR Path 1)," Clinicaltrials.gov, Mar. 6, 2023, 5 pages, [Online] [Retrieved on Apr. 11, 2023].

Anonymous: "NCT05798390: Treatment With Bempedoic Acid And/Or Its Fixed-dose Combination With Ezetimibe in Routine Clinical Practice in Patients With Primary Hypercholesterolemia Or Mixed Dyslipidemia (MILOS-Spain)," Clinicaltrials.gov, Apr. 4, 2023, 5 pages, [Online] [Retrieved on Apr. 11, 2023].

Ansels, Pharmaceutical Dosage Forms and Drug Delivery Systems, 7th Ed. 1999, Lippincott, Williams and Wilkins; Chapters 3 and 7; pp. 60-100 and 179-228.

ApexBio Technology - ETC-1002 (Bempedoic acid), 4 pages, retrieved on Jul. 13, 2021 from <https://www.apexbt.com/etc-1002.html>.

Ark Pharma Scientific Limited - ETC-1002 (Bempedoic acid), 2 pages, retrieved on Jul. 13, 2021 from << http://www.arkpharmtech.com/product/32890.html>>.

Asclepia Capital: Clarifying The Conversation Part II: Esperion Therapeutics, INc. (ESPR), Sep. 7, 2015, 9 pages.

AstaTech Inc, Bempedoic acid, 1 page, retrieved on Jul. 13, 2021 from <https://www.astatechinccom/CPSResult.php?CRNO=86963>.

Aulton et al., Aulton's Pharmaceutics: The Design and Manufacture of Medicines, 4th Edition, Edited by Michael E. Aulton and Kevin M.G. Taylor, 2013, Churchill Livingstone Elsevier, Chapter 12.

Azim et al. (2013) "HPLC Method Development and Validation: A Review," Int. Res. J. Pharm. 4(4)39-46.

Badimon, et al., 1992, "Role of High density lipoproteins in the regression of atherosclerosis", Circulation 85 (Suppl); 11186-94.

Bailey, et al. "Convenient general method for the preparation of primary alkyllithiums by lithium-iodine exchange," (1990) J. Org. Chem. Vol. 55, No. 19, pp. 5404-5406.

Ballantyne et al. (2013) "Efficacy and Safety of a Novel Dual Modulator of Adenosine Triphosphate-Citrate Lyase and Adenosine Monophosphate-Activated Protein Kinase in Patients With Hypercholesterolemia Results of a Multicenter, Randomized, Double-Blind, Placebo- Controlled, Parallel-Group Trial" JACC 62(13) 1154-1162.

Ballantyne et al. (2016) "Effect of ETC-1002 on Serum Low-Density Lipoprotein Cholesterol in Hypercholesterolemic Patients Receiving Statin Therapy," Am. J. Cardio 117:1928-1933.

Ballantyne et al. (2018) "Efficacy and safety of bempedoic acid added to ezetimibe in statin- tolerant patients with hypercholesterolemia: A randomized, placebo-controlled study," Atherosclerosis 277:195-203.

Ballantyne, C et al., "Abstract 17499: ETC-1002 Incrementally Lowers Low Density Lipoprotein-Cholesterol in Patients with Hypercholesterolemia Receiving Stable Statin Therapy," Circulation, Nov. 6, 2015, p. 1, vol. 132, No. Suppl. 3.

Ballantyne, C et al., "Efficacy and Safety of a Novel Dual Modulator of Adenosine Triphosphate-Citrate Lyase and Adenosine Monophosphate-Activated Protein Kinase in Patients with Hypercholesterolemia," Journal of the American College of Cardiology, Sep. 24, 2013, pp. 1154-1162, vol. 62, No. 13.

Bangalore et al. (2007) "Fixed-Dose Combinations Improve Medication Compliance: A Meta- Analysis" American Journal of Medicine 120:713-719.

Bari et al. (2007) "Impurity Profile: Significance in Active Pharmaceutical Ingredient," Eurasian Journal of Analytical Chemistry 2(1):32-53.

Barrans, et al., 1996, "Pre-beta HDL; structure and metabolism", Biochim, Biophys. Acta. 1300(2):73-85.

Bar-Tana, et al. (1989) "Synthesis and Hypolipidemic and Antidiabetogenic Activities of B, B,B', B'- Tetrasubstituted, Long-Chain Dioic Acids," J. Med. Chem. 32:2072-2084.

Barter et al., "Effects of Torcetrapib in Patients at High Risk for Coronary Events," N. Eng. J. Med., 2007, 351(21), 2109-2122.

Bays et al., "Bempedoic acid safety analysis: Pooled data from four phase 3 clinical trials," Journal of Clinical Lipidology, 14: 649-659 (2020).

Becker, et al., 1982, "Intramolecular photoaddition of terminal allenes to conjugated cyclohexenones", J. Org. Chem. 47:3297-3310.

Beilstein Report for Compound Beilstein Registry No. 1741087, based in part on Crisan et al. (1956), Ann. Chim, (Paris), 13(1): 436-459.

Beilstein Report for Compound Beilstein Registry No. 1778991, based in part on Pechmann (1904), Chem. Ber., 37: 3819.

Beilstein Report for Compound Beilstein Registry No. 1784568, based in part on English (1941), J. Am. Chem. Soc., 63 (4): 941-943.

Beilstein Report for Compound Beilstein Registry No. 2961112, based in part on Lardelli et al. (1967), Recl. Trav. Chim., 86: 481-503.

Beilstein Report for Compound Beilstein Registry No. 5836264, based in part on Weber et al. (1992), J. Med. Chem., 35(21): 3755-3773.

(56) References Cited

OTHER PUBLICATIONS

Beilstein Report for Compound Beilstein Registry No. 7473723, based in part on Rieke et al. (1996), J. Org. Chem., 61(8): 2726-2730.
Bell (2013) "Combine and conquer: advantages and disadvantages of fixed-dose combination therapy" Diabetes, Obesity & Metabolism 15:291-300.
Bell et al. (2005) "alpha-Cycloalkyl-substituted omega-keto-dicarboxylic acids as lipid regulating agents" Bioorganic & Medicinal Chemistry 13:223-236.
Berenson, A., "For Widely Used Drug, Question of Usefulness Is Still Lingering," The New York Times Company, Sep. 1, 2008, @2018, 12 pages, [Online] [Retrieved Jan. 25, 2018] Retrieved from the Internet: < URL:http://www.nytimes.com/2008/09/02/business/02vytorin.html>.
Berkhout et al., The effect of (-)-hydroxycitrate on the activity of the low-density-lipoprotein receptor and 3-hydroxy-3-methylglutaryl-CoA reductase levels in the human hepatoma cell line Hep G2, Biochem J 272(1): 181-186 (1990).
Bernady, et al. "Prostaglandins and congeners. 20. Synthesis of prostaglandins via conjugate addition of lithium trans-1-alkenyltrialkylalanate reagents. A novel reagent for conjugate 1,4-additions," J. Org. Chem. (1979) vol. 44, No. 9, pp. 1438-1447.
Bhanot, et al. "Synthetic studies on Terpenoids. 5. Syntheses of g- and d-Lactones from b-(2,7- Dimethyl-1,2-dihdroxycycloheptyl)propionic Acid," J. Org. Chem. (1977) vol. 42, pp. 1623-1627.
Bicking, et al., "11, 12-Secoprostaglandins. 1. Acylhydroxyalkanoic acids and related compounds", J. Med. Chem., 1977, pp. 35-43, vol. 20.
Bilen et al. (2016) "Bempedoic Acid (ETC-1002): An Investigational Inhibitor of ATP Citrate Lyase," Curr. Atheroscler. Rep. 18:61 (7 pages).
BioChemPartner—Bempedoic acid, 2 pages, retrieved on Jul. 13, 2021 from <http://www.biochempartner.com/738606-46-7-BCP16083>.
Bisgaier, et al., 1997, "Attenuation of plasma low density lipoprotein cholesterol by select 3- hydroxy-3-methylglutaryl coenzyme A reductase inhibitors in mice of low density lipoprotein receptors", J. Lipid Res. 38 (12):2502-2515.
Bisgaier, et al., 1998, "A novel compound that elevates high density lipoprotein and activates the peroxisome proliferator activated receptor", J. Lipid Res. 39(1): 17-30.
Bitzur et al., Intolerance to Statins: Mechanisms and Management, Diabetes Care, 36(2): S325-S330 (2013).
Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.
Blatt, et al., "The reducing action of Grignard reagent and the synthesis of tertiary aliphatic carbinols", J. Org. Chem., 1932, pp. 1495-1499, vol. 54.
Bongini, et al., 1979 "A simple and practical method for tetrahydropyranylation of alcohols and phenols", Synthesis 618-620.
Braatz et al., "Crystallization: Particle Size Control," Encyclopedia of Pharmaceutical Technol. 3d edition, vol. 1:858-71 at 858 (J. Swarbrick, ed., Informa Healthcare USA, Inc, 2007).
Brown, et al. "Selective reductions. 26. Lithuim triethylborohydride as an exceptionally powerful and selective reducing agent in organic synthesis. Exploration of the reactions with selected organic compounds containing representative functional groups," J. Org. Chem. (1980) vol. 45, No. 1, pp. 1-12.
Brown, H. C. et al. "Hydroboration. 67. Cyclic hydroboration of acyclic alpha, omega-dienes with 9- borabicyclo[3.3.1]nonane/borane-dimethyl sulfide," J. Org. Chem. (1984) vol. 49, No. 6, pp. 1072-1078.
Brown, H. C. et al. "Selective reductions. VII. Reaction of lithium trimethoxyaluminohydride with selected organic compounds containing representative functional groups," J. Am. Chem. Soc (1965) vol. 87, No. 24, pp. 5614-5620.
Bruce, et al., 1998, "Plasma lipid transfer proteins, high-density lipoproteins, and reverse cholesterol transport", Annu Rev Nutr. 1998; 18:297-330.
Byrn et al., 1995, "Pharmaceutical Solids: A Strategic Approach to Regulatory Considerations," Pharmaceutical Research, 12(7): 945-854.
Byrne et al. (2016) "Tools and techniques for solvent selection: green solvent selection guides" Sustain Chem Process 4(7) (24 pages).
Caira (1998) "Crystalline Polymorphism of Organic Compounds," Topics in Current Chemistry 198:163-208.
Campagna, et al., 1994, "Cyclic Amidine Analogues of Taurine and Homotaurine; Synthesis and Effects on Rat Skeletal Muscle", Farmaco, Ed. Sci 49:653-658.
Cannon et al., "Ezetimibe Added to Statin Therapy after Acute Coronary Syndromes," N. Eng. J. Med., 2015, 372(25), 2387-2397.
Carothers et al., 1924, "Platinum oxide as a catalyst in the reduction of organic compounds. V. The preparation of primary alcohols by the catalytic hydrogenation of aldehydes," J. Am. Chem. Soc 46:1675-83.
Cerny, et al., 1969, "Properties of Sodium Bis-(2-Methoxyethoxy)-Aluminum Hydride", Collect Czech Chem Comm. 34:1025-33.
Chadwick, et al., 1979, "Reaction between N-Alkylpyroles and Alkyllithium Reagents" J. Chem Soc, Perkin Trans. 12845.
Chaikin et al. (1949) "Reduction of Aldehydes, Ketones and Acid Chlorides by Sodium Borohydride," J. Am. Chem. 71:122-125.
Chapman et al., 2005, "Predictors of Adherence with Antihypertensive and Lipid-Lowering Therapy", Arch. Intern. Med., 165(10): 1147-1150.
Chemical Engineering in the Pharmaceutical Industry: Drug Product Design, Development, and Modeling (2ed Mar. 29, 2019).
ChemScene LLC, Bempedoic acid, 2 pages, retrieved on Mar. 10, 2021 from <http://abachemscene.com/738606-46-7.html>.
Chen, et al., 1998, "Asymmetric total synthesis of phosphatidylinositol 3-phosphate and 4- phosphate derivatives", J. Org. Chem. 63:6511-22.
Chow et al., Sample Size Calculations in Clinical Research (2nd ed.). Chapman & Hall/CRC, 480 pages (2008).
Chung et al., The Prevalence of Negative Studies with Inadequate Statistical Power: An Analysis of the Plastic Surgery Literature, Plastic and Reconstructive Surgery 109(1) 1-6 (2002).
Clauss et al. (2009) "Ezetimibe treatment of pediatric patients with hypercholesterolemia," J Pediatr. 154(6):869-72.
Clayden et al., Organic Chemistry (2nd Ed 2012).
Comins, et al., 1981, "A one pot synthesis of unsymmetrical secondary alcohols from two grignard reagents", Tetrahedron Lett. 22:1085-88.
Corbridge, 1985, "Phosphorus: An Outline of its Chemistry, Biochemistry and Technology", Studies in Inorganic Chemistry, 3rd ed, pp. 357-395.
Corey, et al., 1967, "A useful method for the conversion of alcohols into iodides", J. Org. Chem. 32:4160-4161.
Corey, et al., 1979, "Useful procedures for the oxidation of alcohols involving pyridinum dichromate in aprotic media", Tetrahedron Lett. 5:399-402.
Cramer et al. "Effects of a novel dual lipid synthesis inhibitor and its potential utility in treating dyslipidemia and metabolic syndrome" J. Lipid Res .; 2004; 1289-1301.
Dalton, J.C. et al. (1971) "Type I and Type II Photochemical Reactions of Some Five- and Six- Membered Cycloalkanones," J. Am. Chem. Soc, 93 (26): 7213-21.
Danheiser, et al., 1991, "A Practical and Efficient Method for Synthesis of b-Lactones", J. Org. Chem. 58:1176-65.
Dansky HM, Fisher Ea, 1999, "High-density lipoprotein and plaque regression: the good cholesterol gets even better", Circulation 100(17): 1762-3.
Davidson et al., Colesevelam Hydrochloride (Cholestagel): A New, Potent Bile Acid Sequestrant Associated With a Low Incidence of Gastrointestinal Side Effects, JAMA Internal Medicine 159(16): 1893 - 1900 (1999).
DC Chemicals—Bempedoic acid, 2 pages, retrieved on Jul. 13, 2021 from <https://www.dcchemicals.com/product_show-Bempedoic_Acid_ETC_1002_ESP_55016 .html>.

(56) References Cited

OTHER PUBLICATIONS

De Sarlo, et al., 1971, "Isoxazolin-5-one", J. Chem Soc 88-89.
Decossin, et al., 1997, "Subclasses of LpA-I in coronary artery disease: distribution and cholesterol efflux ability", Eur J Clin Invest. 27(4): 299-307.
Drug Bank Online, Bempedoic acid, 9 pages, retrieved on Jul. 12, 2021 from <https://go.drugbank.com/drugs/DB11936>.
Dubois et al., Tolvaptan, British J. of Clin. Pharmacol., 73(1): 9-11 (2012).
Eaton, et al., 1972, "Hydroxypropylation", J. Org. Chem. 37:1947-50.
Ehlinger, et al., 1980, "Silicon in Synthesis. 10. The (trimethylsiyl)allyl Anion: A. beta-Acyl anion equivalent for the conversion of aldehydes and ketones into gamma-lactone", J. Am. Chem. Soc 102:5004-11.
Eisch, et al. 1978, "Synthesis of lactones via the titanium-catalyzed hydromagnesiation of alkenols", J. Organomet. Chem. 160:C8-C12.
Elder et al. (2008) "Control and analysis of alkyl and benzyl halides and other related reactive organohalides as potential genotoxic impurities in active pharmaceutical ingredients (APIs)," J. Pharm. & Biomed Analysis 48:497-500.
ENovation Chemicals LLC - Bempedoic acid, 1 pages, retrieved on Jul. 13, 2021 from <https://www.enovationchem.com/ProductDetails.asp?cellC=+bgcolor%3D%27%23E8F8FF%27+ &ProductID=KP-43530>.
ESP-006EAD1 Declaration by Richard R. Copp, dated Sep. 23, 2024, 9 pages.
ESP-006WOC1 Declaration by Michael P. Scannell Under 37 CFR 1.132, dated Jun. 10, 2021, 11 pages.
ESP-006WOC4 Declaration by Richard R. Copp Under 37 CFR 1.132, dated Oct. 3, 2022, 22 pages.
Esperion Therapeutics Announces Positive Top-Line Phase 2b Results for ETC-1002, An Investigational Therapy for Patients with Hypercholesterolemia; available at https://www.esperion.com/news-releases/news-release-details/esperion-therapeutics-announces- positive-top-line-phase-2b (Publication date: Oct. 1, 2014).
Esperion Therapeutics Announces Positive Top-Line Results from Phase 2 Clinical Study of ETC-1002 as an Add-On to Statin Therapy in Patients with Hypercholesterolemia, Sep. 3, 2013, 1-2.
Esperion Therapeutics Investor & Analyst Reception, Nov. 17, 2014, 21 pages.
Esperion Therapeutics Presents Full Results of Phase 2 Clinical Study Demonstrating that ETC-1002 Lowered LDL-C by an Average of 32 Percent and Was Well Tolerated in Patients with Hypercholesterolemia and History of Statin Intolerance; Nov. 18, 2013, available at https://www.esperion.com/news-releases/news-release-details/esperion-therapeutics-presents-full-results-phase-2-clinical-0.
Esperion Therapeutics Presents Full Results of Phase 2 Clinical Trial Showing Its Novel Oral Therapy ETC-1002 Lowered LDL-C By Up to 43 Percent in Hypercholesterolemic Patients with Type 2 Diabetes Data Presented at ATVB 2013 Scientific Sessions, May 2, 2013, 1-2.
Esperion Therapeutics Reports Second Quarter Financial Results and Provides Corporate Update, Aug. 12, 2013, 1-3.
Esperion Therapeutics, "Esperion Therapeutics Announces Positive Top-Line Phase 2b Results for ETC-1002, an Investigational Therapy for Patients With Hypercholesterolemia," Esperion Press Release, Oct. 1, 2014, entire document.
European Extended Search Report, European Application No. 16765550.5, Oct. 8, 2018, 8 pages.
European Extended Search Report, European Application No. 16765682.6, Jun. 28, 2018, 10 pages.
European Medicines Agency, "Concept paper on the need to revise the Guideline on the clinical development of fixed dose combinations of medicinal products regarding dossier content requirements," Committee for Medicinal Products for Human Use (CHMP) of the EMA, Feb. 11, 2013.
Excenen PharmaTech—ETC-1002 (Bempedoic acid), 2 pages, retrieved on Jul. 13, 2021 from <https://excenen.com/searchresultlist.php?id=EX-A1243>.
Ezetimibe Tablets (Zetia) label (2012).
FDA Guidance For Industry: Drug Substance Chemistry, Manufacturing, and Controls Information, Aug. 6, 2010.
FDA Guidance For Industry: Manufacturing, Processing, or Holding Active Pharmaceutical Ingredients, Mar. 1998.
FDA Guidance for Industry: Q3A Impurities in New Drug Substances, Jun. 2008.
Fielding & Fielding, 1995, "Molecular physiology of reverse cholesterol transport", J. Lipid Res. 36(2):211-28.
Filippov et al. "ETC-1002 Regulates Immune Response, Leukocyte Homing and Adipose Tissue Inflammation via LKB1-Dependent Activation of Macrophage Ampk." J. Lipid Res .; 2013; 54; 2095-2108.
Filippov et al., LDL-cholesterol reduction in patients with hypercholesterolemia by modulation of adenosine triphosphate-citrate lyase and adenosine monophosphate-activated protein kinase, Curr Opin Lipidol 25: 309-315 (2014).
Finkelstein, H. Ber. 1910, Dtsch. Chem. Ges., 43, 1528-15232.
Foody (2013) "Familial Hypercholesterolemia: An Underrecognized but Significant Concern in Cardiology Practice," Clin. Cardiol. 37(2): 119-125.
Fraser, et al., 1985, "Acidity measurements in THF. V. Heteroaromatic compounds containing 5- membered rings", Can J. Chem. 63:3505-09.
Fujiwara et al. (2005) "First-Principles and Direct Design Approaches for the Control of Pharmaceutical Crystallization," J. Process Control 15:493-504.
Gabow, Autosomal Dominant Polycystic Kidney Disease, The New England Journal of Medicine, 329: 332-342 (1993).
Gagne et al.(2013) Efficacy and Safety of Ezetimibe Monotherapy in 6-10 Year Old Children with Heterozygous Familial or Nonfamilial Hypercholesterolemia; Journal of Clinical Lipidology 7(3):257-258.
Garegg, et al., 1980, "Novel Reagent System for converting a Hydroxy-group into an lodo-group in carbohydrates with inversion of Configuration", J.CS. Perkin | 2866-2868.
Gautam et al., "Fixed dose drug combinations (FDCs): rational or irrational: a view point," Br. J. Clin. Pharmacol., 2008, May 65(5), 795-796.
Gearing, et al., 1993, "Interaction of the peroxisome-proliferator-activated receptor and retinoid X receptor", Proc. Natl. Acad. Sci. USA 90(4): 14440-1444.
Gigg, et al., 1967, "The Preparation of Unsymmetrical Diglycerides", J. Chem. Soc, C 431-434.
Gleiter, R. et al. "Synthesis and properties of 4,4,9,9-tetramethyl-1-oxa-cycloundecane-5,6,7,8- tetrone and 5,5, 10, 10-tetramethyl-1-oxa-cyclotridecane-6,7,8,9-tetrone," Chemistry—A European Journal (1996) vol. 2, No. 3, pp. 271-277.
Gleiter, R. et al., "Synthesis of 5,5, 10, 10-tetramethyl-1-oxacyclotridecane-6,7,8,9-tetrone—on the mechanism of the Rubotom reaction," Eur. J. Org. Chem. (1995) No. 9, pp. 1655-1661.
Green and Kehinde, 1975, "An established predispose cell line and its differentiation in culture II. Factors affecting the adipose conversion", Cell. 5(1): 19-27.
Greene, T.W., 1999, "Protection for the Hydroxyl Group, Including 1,2-and 1,3-Diols", Protective Groups in Organic Synthesis.
Gribble, et al. (1996) "ATP-Citrate Lyase as a Target for the Hypolipidemic Intervention. Design and Synthesis of 2-Substituted Butanedioic Acids as Novel, Potent Inhibitors of the Enzyme," J. Med Chem. 39:3569-2584.
Grigore et al., "Combination therapy in cholesterol reduction: focus on ezetimibe and statins," Vascular Health and Risk Management 2008, 4(2), 267-278.
Gutierrez et al. (2014) "Efficacy and Safety of ETC-1002, a Novel Investigational Low-Density Lipoprotein-Cholesterol-Lowering Therapy for the Treatment of Patients With Hypercholesterolemia and Type 2 Diabetes Mellitus" Arteriosclerosis, Thrombosis & Vascular Biology 34:676-683.
Guyton et al., An assessment by the Statin Intolerance Panel: 2014 update, J Clin Lipidol 8: S72- S81 (2014).

(56) References Cited

OTHER PUBLICATIONS

Hallows et al., "Beneficial Effects of Bempedoic Acid Treatment in ADPKD Mice," Journal of the American Society of Nephrology 32(10S): 403 (2021).
Hamilton-Craig et al. (2010) "Combination Therapy of Statin and Ezetimibe for the Treatment of Familial Hypercholesterolemia," Vascular Health and Risk Management 6:1023-1037.
Hangzhou MolCore BioPharmatech Co., Ltd. - Bempedoic acid, 7 pages, retrieved on Jul. 13, 2021 from <https://www.molcore.com/product/738606-46-7>.
Harris and Kletzien, 1994, "Localization of pioglitazone response element in the adipocyte fatty acid-binding protein gene", Mol Pharmacol. 45(3):439-45.
Hayden and Ma, 1992, "Molecular genetics of human lipoprotein lipase deficiency", Mol Cell Biochem. 113(2):171-6.
Heyman, et al., 1992, "9-cis retinoic acid is high affinity ligand for the retinoid X receptor", Cell 68(2): 397-406.
Hidaka and Fidge, 1992, "Affinity purification of the hepatic high-density lipoprotein receptor identifies two acidic glycoproteins and enables further characterization of their binding properties", Biochem. J. 15(Pt1): 161-7.
Hilfiker et al., 2006, "Relevance of Solid-state Properties for Pharmaceutical Products," Polymorphism: in the Pharmaceutical Industry, pp. 1-19.
Hirano, et al., 1997, "Genetic cholesteryl ester transfer deficiency is extremely frequent in the Omagari area of Japan. Marked hyperalphalipoproteinema caused by CETP gene mutation is not associated with longevity", Arterioscler. Thromb. VascBiol. 17(6): 1053-1059.
Hovingh et al. (2013) "Diagnosis and Treatment of Familial Hypercholesterolaemia," European Heart Journal 34:962-971.
Hoyer, et al., 1986, "Catalysis by acidic clay of the protective tetrahydropyranylation of alcohols and phenols", Synthesis 655-57.
Hudlicky, M., 1996, "Reduction of aldehydes and their derivatives", Reductions in Organic Chemistry, 2nd ed. pp. 137-139.
Hudlicky, M., 1996, "Reduction of esters and lactones of carboxylic acids", Reduction in Organic Chemistry 2nd ed. pp. 212-217.
Hunyadi et al. (2018) "Crystalline form of 8-hydroxy-2,2, 14, 14-tetramethylpentadecanedioic acid," 18(7A): 1-9 (No. IPCOM00025443D).
ICH Harmonised Tripartite Guideline-Impurities in New Drug Substances Q3A(R2), Oct. 25, 2006.
ICH Harmonised Tripartite Guideline-Specifications: Test Procedures And Acceptance Criteria For New Drug Substances And New Drug Products: Chemical Substances Q6A, Step 4 version, Oct. 6, 1999.
ICH Harmonized Tripartite Guideline, Impurities in new drug substances Q3A(R2),(The International Council for Harmonization, Oct. 25, 2006).
International Search Report and the Written Opinion of the International Search Authority, or the Declaration, Int'l Application No. PCT/US18/17434, mailed Apr. 19, 2018, 16 pages.
International Search Report and Written Opinion for PCT/2022/031729, dated Sep. 12, 2022, 11 pages.
International Search Report and Written Opinion for PCT/US2018/034646 mailed Jul. 24, 2018 12 pages.
International Search Report and Written Opinion for PCT/US2019/018356, mailed May 16, 2019, 11 pages.
International Search Report and Written Opinion for PCT/US2019/048183, mailed Nov. 7, 2019, 9 pages.
International Search Report and Written Opinion forPCT/US2015/021677, Apr. 16, 2015, 8 pages.
International Search Report and Written Opinion, International Application No. PCT/US2020/038622, mailed on Nov. 25, 2020 (25 pages).
International Search Report and Written Opinion, International Application No. PCT/US2020/038624, mailed Sep. 15, 2020 (16 pages).
International Search Report for PCT/US2016/022319, Jun. 3, 2016, 2 pages.
International Search Report, International Application No. PCT/US2003/041411, mailed Dec. 8, 2004 (12 pages).
Ishibashi, et al., 1993, "Hypercholesterolemia in low density lipoprotein receptor knockout mice and its reversal by adenovirus-mediated gene delivery", J. Clin. Invest. 92(2):883-93.
Ishibashi, et al., 1994, "Massive xanthomatosis and atherosclerosis in cholesterol-fed low density lipoprotein receptor-negative mice", J. Clin Invest. 93(5):1885-93.
Ishii et al., 1983, "Catalytic Regioselective Dehydrogenation of Unsymmetrical alpha Omega-Diols Using Ruthenium Complexes", Tetrahedron Lett. 26:2677-2680.
Ishii, et al., 1986, "Ruthenium Complex Catalyzed Regioselective Dehydrogenation of Unsymmetrical alpha Omega-Diols", J. Org. Chem. 51:2034.
Isseman and Green, 1990, "Activation of a member of the steroid hormone receptor superfamily by peroxisome proliferators", Nature 347(6294):645-650.
Ito et al., Muscle symptoms in statin users, associations with cytochrome P450, and membrane transporter inhibitor use: a subanalysis of the USAGE study, J Clin Lipid, 8: 69-76 (2014).
Ito, et al., 2000, "Regio-and diastereocontrol in carbonyl allylation by 1-halobut-2-enes with Tin(II) halides", J Org Chem. 65(2):494-8.
Iwai, et al., 1966, "Studies on acetylenic compounds. XLIV. Synthesis of 3-aminoisoxazoles and 3- hydroxyisoxazoles (3-Isoxazolones)", Chem. Pharm. Bull. 14:1277-88.
Jacobs (1997) lonic Species, in Understanding Organic Reaction Mechanisms 30-58 (Cambridge Univ. Press 1997).
Jetter, R., "Long-chain alkanediols from Myricaria germanica leaf cuticular waxes," Phytochemistry, 55 (2), 2000, pp. 169-176.
Johnston, et al., 1988, "A new, mild heterogeneous catalyst for the tetrahydropyranylation of alcohols and phenols", Synthesis 393-4.
Jones, Jr. (1997) The Chemistry of Alcohols Revisited and Extended: Glycols, Ethers, and Related Sulfur Compounds, in Organic Chemistry 817-876 (W. W. Norton & Company 1997).
Jurg Husler, Statistical Analyses for Clinical Studies, Quintessence Publ., 121 -134 (2015).
Kanai, et al., 1995, "Catalytic Asymmetric Conjugate Addition of Grignard Reagents Mediated by Copper (I)-Chiral Bidentate Phosphine Complex", Tetrahedron Lett. 36:4275-4278.
Kane, New horizons in lipid management, J Am Coll Cardiol 62: 1163-4 (2013).
Kastelein et al. (2013) "Efficacy and Safety of Ezetimibe Monotherapy in Children Six to Ten Years of Age With Heterozygous Familial or Non-Familial Hypercholesterolemia," JACC 61(10) (10_ Supplement) E1466.
Katritzky, et al., 1993, "Generation and Reactions of sp2-Carbanionic Centers in the Vicinity of Heterocyclic Nitrogen Atoms", Adv. Het. Chem. 56:155-303.
Katsiki et al., "Non-alcoholic Fatty Liver Disease and Dyslipidemia: An Update," 2016, Metabolism, 65(8), pp. 1109-1123.
Keller and Wahli, 1993, "Peroxisome proliferator-activated receptors-A link between endocrinology and Nurition?" TEM, 4:291-295.
Keller, et al., 1993, "Fatty acids and retinoids control lipid metabolism through activation of peroxisome proliferator-activated receptor-retinoid X receptor heterodimers", Proc. Natl. Acad. Sci. USA 90(6): 2160-2164.
Kessar, et al., 1997, "Lewis acid complexation of tertiary amines and related compounds: A strategy for a a-deprotonation and stereocontrol", Chem. Rev. 97:721-37.
Klencsár et al. (2017) "Development and validation of a novel quantification approach for gradient elution reversed phase high-performance liquid chromatography coupled to tandem ICP-mass spectrometry (RP-HPLC-ICP-MS/MS) and its application to diclofenac and its related compounds," Anal. Chim. Acta 974:43-53.
Kletzein, et al., 1991, "Enhancement of adipocyte differentiation by an insulin-sensitizing agent", Mol Pharmacol 41(2):393-398.
Kliewer, et al., 1992, "Convergence of 9-cis retinoic acid and peroxisome proliferator signaling pathways through heterodimer formation of their receptors", Nature 27;358(6389): 771-4.
Klug (1993) The Influence of Impurities and Solvents on Crystallization, in Handbook of Industrial Crystallization 65-87 (A.S. Myerson ed., 1993).

(56) References Cited

OTHER PUBLICATIONS

Knopp et al., Effects of fenofibrate on plasma lipoproteins in hypercholesterolemia and combined hyperlipidemia, Am J Med, 83: 50-59 (1987).
Kolata, G., "Dashing Hopes, Study Shows a Cholesterol Drug Had No Effect on Heart Health," The New York Times Company, Apr. 3, 2016, @2018, 9 pages, [Online] [Retrieved Jan. 25, 2018] Retrieved from the Internet: < URL:https://www.nytimes.com/2016/04/04/health/dashing- hopes-study-shows-cholesterol-drug-has-No.benefits.html>.
Kumar et al. (2013) "Recent Analytical Method Developed by RP-HPLC," Global Journal of Pharmacology 7(3)232-240.
Kurata, et al., 1998, "A candidate high density lipoprotein (HDL) receptor, HB2, with possible multiple functions shows sequence homology with adhesion molecules", J. Atherosclerosis and Thrombosis 4(3):112-7.
Kurz, et al., 1985, "Anomalous selectivities in methyl transfers to water: An explanation using free energy surfaces which model the effects of non-equilibrium solvation", Isr. J. Chem. 26:339-48.
Kurz, et al.. "Evidence for rate-determining solvation change in methyl transfer to water. Solvent dependence of H2O/D20 kinetic isotope effects," J. Am. Chem. Soc (1986) vol. 108, pp. 2960-2968.
Kusters et al. (2015) "Efficacy and Safety of Ezetimibe Monotherapy in Children with Heterozygous Familial or Nonfamilial Hypercholesterolemia," The Journal of Pediatrics 166(6): 1377-1384.
Kwan et al., 2013, "Polypharmacy: Optimizing Medication Use in Elderly Patients", CGS Journal of CME, 4(1):21-27.
Lagrost, et al., 1996, "Opposite effects of cholesteryl ester transfer protein and phospholipid transfer protein on the size distribution of plasma high density lipoproteins. Physiological relevance in alcoholic patients", J. Biol. Chem.271(32):19058-65.
Lambert et al., "Current Treatment of Familial Hypercholesterolaemia," European Cardiology Review, 2014, 9(2), 76-81.
Landshultz, et al., 1996, "Regulation of scavenger receptor, class B, type I, a high density lipoprotein receptor, in liver and steroidogenic tissues of the rat", J. Clin. Invest. 98(4):984-995.
Larock, 1989, Comprehensive Organic Transformations; Ch. 6, VCH: New York, pp. 446-448.
Lazarow and Fujiki, 1985, "Biogenesis of peroxisomes", Annu Rev Cell Biol. 1:489-530.
Levin, et al., 1992, "9-cis retinoic acid stereoisomer binds and activates the nuclear receptor RXR alpha", Nature 355(6358):359-61.
Lipka (2003) "Ezetimibe: a first-in-class, novel cholesterol absorption inhibitor," Cardiovascular Drug Reviews 21(4):293-312.
Lorimer (2011) "Oral Dosage Formulation Development"; available at https://www.almacgroup.com/wp-content/uploads/2015/02/Almac-Article_Achieving-faster- formulation-of-solid-oral-dosage-forms-for-FIH-supplies_Contract-Pharma_May-2011.pdf.
Ludwig, et al., 1989, "Rapid and efficient synthesis of nucleoside 5'-0-(1-thiotriphosphates), 5'- triphosphates and 2', 3'-Cyclophosphorothioates using 2-Chloro-4H-1,3,2-benzodioxaphosphorin- 4-one", J. Org. Chem. 54:631-35.
Maddaford, et al., 1993, "A general asymmetric synthesis of (-)-alpha-Dimethylretrodendrin and its diastereomers", J. Org. Chem 58:4132-38.
Mampuya et al., Treatment strategies in patients with statin intolerance: the Cleveland Clinic experience, Am Heart J. 166(3): 597-603 (2013).
March, J., 1992, Advanced Organic Chemistry: Reactions, Mechanisms, and Structure 4th ed., pp. 248-272, 1196-98, 437-438, 920-929.
Masamune, et al. "Tylonolide hemiacetal, the aglycone of tylosin, and its partial synthesis," J. Am. Chem. Soc (1976) vol. 98, No. 24, pp. 7874-7875.
Masuda et al.(2009) "Ezetimibe improves postprandial hyperlipidaemia in patients with type IIb hyperlipidemia" European Journal of Clinical Investigation 39:689698.
Masuda et al., "Ezetimibe Improves Postprandial Hyperlipidaemia in Patients with Type IIb Hyperlipidaemia," Eur. J. Clin. Invest., vol. 39 (8), 2009, pp. 689-698.
Mauro et al. (2003) "Ezetimibe for Management of Hypercholesterolemia," The Annuals of Pharmacotherapy 37:839-848.
McCune et al., "Effect of Mevinolin on Cholesterol Metabolism in Obese and Lean Zucker Rats," Biochemical Pharmacology (1987) vol. 36, pp. 875-879. (abstract only).
MedChemExpress LLC, Bempedoic acid, 3 pages, retrieved on Mar. 10, 2021 from <https://www.medchemexpress.com/ETC-1002.html>.
Menger, et al., 1981, "Synthetically useful oxidations at solid sodium permanganate surfaces", Tetrahedron Lett. 22:1655-56.
Miyashita, et al., 1977, "Pyridinium .rho .- Toluenesulfonate. A mild and efficient catalyst for the tetrahydropyranylation of alcohols", J. Org. Chem 42:3772-74.
Mizukami, et al., 2015, "Halogen Exchange Reaction of Aliphatic Fluorine Compounds with Organic Halides as Halogen Source," Organic Letters 17:5942-5945.
Moffet, et al., 1963, "2-(1-Pyrrolidyl)Propanol", Org. Synth. Collect 4:834-5.
Moriarty et al., Odyssey Alternative: Efficacy and safety of the proprotein convertase subtilisin/kexin type 9 monoclonal antibody, alirocumab, versus Ezetimibe, in patients with statin intolerance as defined by a placebo run-in and statin rechallenge armd, American Heart Association 2014 Scientific Sessions, Nov. 17, 2014, 3 pages.
Morris et al. (2003) "Ezetimibe for Hypercholesterolemia," American Family Physician 2 p. https://www.aafp.org/pubs/afp/issues/2003/1015/p1595.html.
Moßhammer et al., Mechanisms and assessment of statin-related muscular adverse effects, British Journal of Clinical Pharmacology, 78(3): 454-466 (2014).
Moynihan et al. (2017) "Impurity Occurrence and Removal in Crystalline Products from Process Reactions" Organic Process Research and Development 21(5): 689-704.
Mueller et al. (2004) "Long Hydrocarbon Chain Keton Diols and Diacids that Favorably Alter Lipid Disorders in Vivo," J. Med. Chem. 47:6082-6099.
Mulzer, 1995, Comprehensive Organic Functional Group Transformations Oxford 5 p. 161.
Musechem, Bempedoic acid, 6 pages, retrieved on Mar. 10, 2021 from <https://www.musechem.com/product/1004743.html>.
Myers, et al., 1992, "Studies on the thermal generation and reactivity of a class of (.alpha., .pi.)- 1,4-biradicals", J. Am. Chem. Soc 114:9369-86.
Nagano H., et al., "Stereoselectivitiy in the formation and radical reduction of cyclic bromoacetals, key intermediates for the synthesis of delta-hydroxy-and epilson-hydroxy-alpha-methylcarboxylic acid esters", Tetrahedron Letters, 2003, pp. 6867-6870, vol. 44, No. 36.
Nan F, et al., "Dual Function Glutamate-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.
NCT01751984 (2012) "A Placebo-Controlled, Randomized, Double-Blind, Parallel Group, Multicenter Study to Evaluate the Efficacy and Safety of ETC-1002 in Subjects With Hypercholesterolemia and a History of Statin Intolerance".
NCT01941836 (2013) "A Randomized, Double-Blind, Parallel Group, Multicenter Study to Evaluate the Efficacy and Safety of ETC-1002, Ezetimibe, and the Combination in Hypercholesterolemic Patients With or Without Statin Intolerance".
NCT02659397 (2016) "A Study Of Pharmacokinetics, Pharmacodynamics And Safety Of Adding ETC-1002 To Atorvastatin 80 mg".
NCT02666664 (2020) Evaluation of Long-Term Safety and Tolerability of ETC-1002 in High-Risk Patients with Hyperlipidemia and Higyh CV Risk (CLEAR Harmony).
NCT02988115 (2016) "Evaluation of the Efficacy and Safety of Bempedoic Acid (ETC-1002) in Patients With Hyperlipidemia and Statin Intolerant (CLEAR Serenity)".
NCT02991118 (2016) "Evaluation of Long-Term Efficacy of Bempedoic Acid (ETC-1002) in Patients With Hyperlipidemia at High Cardiovascular Risk (CLEAR Wisdom)".

(56) References Cited

OTHER PUBLICATIONS

NCT02993406 (2016) "Evaluation of Major Cardiovascular Events in Participants With, or at High Risk for, Cardiovascular Disease Who Are Statin Intolerant Treated With Bempedoic Acid (ETC-1002) or Placebo (CLEAR Outcomes)".
NCT03001076 (2016) "Evaluation of the Efficacy and Safety of Bempedoic Acid (ETC-1002) as Add-on to Ezetimibe Therapy in Patients With Elevated Ldl-C (Clear Tranquility)".
NCT03051100 (2017) "Evaluation of the Efficacy and Safety of Bempedoic Acid (ETC-1002) 180mg, Ezetimibe 10mg, and Atorvastatin 20 mg Triplet Therapy in Patients With Elevated LDL-C".
NCT03067441 (2021) "Assessment of the Long-Term Safety and Efficacy of Bempedoic Acid (CLEAR Harmony OLE)".
NCT03193047 (2017) "Evaluation of the Efficacy and Safety of Bempedoic Acid (ETC-1002) 180mg When Added to PCSK9 Inhibitor Therapy".
NCT03337308 (2017) "A Study Evaluating the Safety and Efficacy of Bempedoic Acid Plus Ezetimibe Fixed-Dose Combination Compared to Bempedoic Acid, Ezetimibe, and Placebo in Patients Treated With Maximally Tolerated Statin Therapy".
Nemali, et al., 1988, "Comparison of constitutive and Inducible levels of expression of paroxisomal beta-oxidation and catalase genes in liver and extrahepatic tissues of rat", Cancer Res. 48(18): 5316-24.
Nikolic et al.(2014) "ETC-1002: A Future Option for Lipid Disorders?" Atherosclerosis 237:705-710.
Norata et al., "New Therapeutic Principles in Dyslipidemia: Focus on LDL and Lp(a) Lowering Drugs," Eur. Heart J., vol. 34(24); 3/18//2013, pp. 1783-1789a.
Nystrom, et al., 1947, "Reduction of Organic Compounds by Lithium Aluminum Hyride", J. Am. Chem. Soc 69:1197-1199.
Nystrom, et al., 1949, "Lithium Borohydride as a Reducing Agent", J. Am. Chem. Soc 71:3245-48.
Ogata, et al., 1969, "Kinetics of the Baeyer-Villiger reaction of benzaldehydes with perbenzoic acid in aquoorganic solvents", J. Org. Chem. 34:3985-91.
Okamoto, et al., 1985, "Synthesis of Alkyl Dihydrogenphosphate by the Reaction of Alcohols and Silyl Polyphosphate", Bull Chem. Soc. Jpn. 58:3393-3394.
Olah, et al., 1979, "Transformations with Chlorotrimethylsilane/ Sodium lodide, a Convenient In Situ lodotrimethylsilane Reagent", J. Org. Chem 44:8, 1247-1251.
Olah, et al., 1984, "N-Formylmorpholine: A New and Effective Formylating Agent for the Preparation of Aldehydes and Dialkyl(1-Formylalkyl)phosphonates from Grignard or Organolithium Reagents", J. Org. Chem. 49:3856-3857.
Olah, et al., 1987, "Formylating Agents", Chem. Rev. 87:4, 671-686.
Oniciu et al., (2006) "Influence of Various Central Moieties on the Hypolipidemic Properties of Long Hydrocarbon Chain Diols and Diacids," American Chemical Society 49(1) (15 pages).
Oster, et al., 1983, "Generation and Reactions of the Dianion of 3-Hydroxy-5-methylisoxazole, a convenient b-keto Amide Synthon", J. Org. Chem 48:4307-4311.
Parhofer et al., Expert opinion on the integration of combination therapy into the treatment algorithm for the management of dyslipidaemia: the integration of ezetimibe and bempedoic acid may enhance goal attainment, European Heart Journal -Cardiovascular Pharmacotherapy, 11(4): 367-37 (2025).
Parker et al., Effect of statins on skeletal muscle function, Circulation 127: 96-103 (2013).
Parra, et al., 1992, "A case-control study of lipoprotein particles in two populations at contrasting risk for coronary heart disease. The ECTIM Study", Arterioscler Thromb. 12:701-707.
Patel et al. (2003) "Ezetimibe (Zetia): A New Type of Lipid-Lowering Agent," 16(3) Baylor University Medical Center Proceedings 16(3):354-358.
Paton et al. (2017) "Bempedoic acid," Drugs of the Future, 42(4):201-208.
Pejic; "Familial Hypercholesterolemia;" The Ochsner Journal; 2014; 14(4); 669-672.
Phan et al.(2012) "Ezetimibe therapy: mechanism of action and clinical update," Vascular Health & Risk Management 8:415-427.
Pilaniya et al. 2010, "Recent trends in the impurity profile of pharmaceuticals," J. Adv. Pharm. Tech. Res., 1(3): 302-310.
Pinkosky et al., (2013) "AMP-activated protein kinase and ATP-citrate lyase are two distinct molecular targets for ETC-1002, a novel small molecule regulator of lipid and carbohydrate metabolism," J. Lipid Res. 54: 134-151.
Pinkosky, S.L. et al., "Liver-Specific ATP-Citrate Lyase Inhibition by Bempedoic Acid Decreases LDL-C and Attenuates Atherosclerosis," Nature Communications, Nov. 28, 2016, pp. 1-13.
Plato et al., 1969, "Differential Scanning Calorimetry as a General Method for Determining the Purity and Heat of Fusion of High-Purity Organic Chemicals. Application to 95 Compounds," Analytical Chemistry, 41(2):330-336.
Pollex et al. (2008) "Emerging antidyslipidemic drugs," Expert Opinion Emerging Drugs 13(2):363- 81 ,.
Pop, et al., 1997, "Allylic and Phenolic Phosphate Esters of Dexanabinol", Org. Prep. And Proc. Int. 29:341-347.
Price (2018) "What Could Possibly Go Wrong in API Development," Pharmaceutical Outsourcing - The Journal of Pharmaceutical & Biopharm. 7 pages.
Ramirez, et al. "Phosphorylation by means of cyclic enediol phosphates," Acc. Chem. Res. (1978) vol. 11, p. 239.
Raunio, et al., 1957, "Addition of Propargyl Acetal to Cyclohexanone in the Presence of Sodamide", J. Org. Chem 22:570.
Reaven, 1993, "Role of Insulin resistance in human disease (syndrome X): an expanded definition", Annu Rev Med. 44:121-31.
Reddy and Lalwani, 1983, "Carcinogenesis by hepatic peroxisome proliferators: evaluation of the risk of hypolipidemic drugs and industrial plasticizers to humans", Crit Rev Toxicol. 12(1): 1-58.
Reiner et al., ESC/EAS Guidelines for the management of dyslipidemias: the Task Force for the management of dyslipidemias of the European Society of Cardiology (ESC) and the European Atherosclerosis Society (EAS), Eur Heart J. 32(14): 1769-818 (2011). doi: 10.1093/ eurheartj/ehr158. Epub Jun. 28, 2011. PMID: 21712404.
Remington, The Science and Practice of Pharmacy, Nineteenth Edition-1995, p. 710-712; pp. 1615-1617.
Rigotti, et al., 1996, "Regulation by adrenocorticotropic hormone of the in vivo expression of scavenger receptor class B type I (Sr-Bi), a high density lipoprotein receptor, in steroidogenic cells of the murine adrenal", J. Biol. Chem. 1996, vol. 271(52): 33545-9.
Robins and Fasulo, 1997, "High density lipoproteins, but not other lipoproteins, provide a vehicle for sterol transport to bile", J Clin Invest. 98(3): 380-4.
Robinson (2013) "Management of Familial Hypercholesterolemia: A Review of the Recommendations from the National Lipid Association Expert Panel on Familial Hypercholesterolemia," J Manag Care Pharm. 19(2): 139-49.
Rose-Kahn (1985) "Inhibition of Lipid Synthesis by BB'-Tetramethyl-substituted, C14-C22, a, w- Dicarboxylic Acids in Cultured Rat Hepatocytes," The Journal of Biological Chemistry 260(14):8411-8415.
Rosenson et al., An assessment by the Statin Muscle Safety Task Force: 2014 update, J Clin Lipidol, 8: S58-S71 (2014).
Rowe, "Handbook of Pharmaceutical Excipients, 6th Ed." 2009, Pharmaceutical press, pp. 129-133, 185-188, 317-324, 364-369, 404-407, 581-585, 651-653 and 663-666.
Rowe, et al., Handbook of Pharmaceutical Excipients, 6th Ed. (2009).
Sabatine et al., "Evolocumab and Clinical Outcomes in Patients with Cardiovascular Disease," 2017, 376(18), 1713-1722.
Salen et al., Intestinal Cholesterol Absorption Inhibitor Ezetimibe Added to Cholestyramine for Sitosterolemia and Xanthomatosis, Gastroenterolody 130(6): 1853-1857 (2006).
Sam, et al., 1972, "Crown Polyether Chemistry, Potassium Permanganate Oxidations in Benzene", J. Am. Chem. Soc 94:4024.
Saougos et al., Differential effect of hypolipidemic drugs on lipoprotein-associated phospholipase A2, Arterioscler Thromb Vasc Biol 27: 2236-43 (2007).

(56) References Cited

OTHER PUBLICATIONS

Saulnier, et al., 1982, "Generation and Reactions of 3-Lithio-1-(phenylsulfonyl)Indole", J. Org. Chem 47:757.
Schaper, U.A. (1980) "Die gemischte Guerbet-Reaktion zwischen cyclischen und acyclischen Alkoholen," Fette, Seifen, Anstrichmittel, Industrieverlag von Hernhaussen kg, 82 (11): 454-456.
Schwartz et al., "Alirocumab and Cardiovascular Outcomes after Acute Coronary Syndrome," N. Eng. J. Med., 2018, 379(22), 2097-2107.
Selleck Chemicals, ETC-1002 (Bempedoic acid), 3 pages, retrieved on Mar. 10, 2021 from <https://www.selleckchem.com/products/etc-1002.html>.
Shen, "Cover Up," Innovations in Pharm Tech 52, (2015), pp. 44-47.
Shirley, et al., 1995, "Metalation of pyrrole, 1-methylpyrrole, and 1-phenylpyrrole with n- Butyllithium", J. Org. Chem 20:225-31.
Sianesi, et al., 1971, "2.4-dihydro-1H-2.1-, 3.4-Dihydro-2H-1.2-und. 3.4-Dihydro-1H-2.3-benzothiazin-S.S-dioxid", Chem. Ber. 104:1880-91.
Silverman, The Organic Chemistry of Drug Design and Drug Interaction, 1992, pp. 15-22.
Skinner, et al., 1995, "Benzoylcyanamide from ethyl benzoylitioncarbomate", J. Am. Chem. Soc 77:5440-42.
Slim et al., Ezetimibe-related myopathy: A systematic review, Journal of Clinical Lipidology 2(5): 328-334 (2008).
Smith, et al., 1957, "Nitrogen Compounds of the phosphoric and Phosphonic Acids, III, Preparation and Properties of Amides of Phenylphosphonic and Phenylphosphonothiolic Acids", J. Org. Chem. 22:265-267.
Song, et al., 1999, "Practical asymmetric synthesis of an endothelin receptor antagonist", J. Org. Chem. 64:9658-67.
Soutar et al., "Mechanisms of Disease: genetic causes of familial hypercholesterolemia," Nature Clinical Practice Cardiovascular Medicine, 4(4), 214-225.
Staels and Auwerx, 1998, "Regulation of apo A-I gene expression by fibrates", Atherosclerosis 137 Suppl:S19-23.
Statistical Principles for Clinical Trials (Ich E9): An Introductory Note on an International Guideline. Stat Med. 18(15): 1903-42 (1999).
Stein et al., Efficacy and tolerability of fluvastatin XL 80 mg alone, Ezetimibe alone, and the combination of fluvastatin XL 80 mg with Ezetimibe in patients with a history of muscle-related side effects with other statins, Am J Cardiol, 101: 490-6 (2008).
Steven A. Hardinger (1995) "A Simple Demonstration of the Effect of Impurities on Melting Point" J of Chemical Education 72:250.
Stevens, et al., 1982, "Further studies on the utility of sodium hypochlorite in organic synthesis Selective oxidation of diols and direct conversion of aldehydes to esters," Tetrahedron Lett. 23:4647-4650.
Stone et al., ACC/AHA Guideline on the Treatment of Blood Cholesterol to Reduce Atherosclerotic Cardiovascular Risk in Adults, J Am Coll Cardiol. 63(25): 2889-2934 (2014).
Stowell, et al., 1995, "A new method for the phosphorylation of alcohols and phenols", Tetrahedron Lett. 36(11): 1825-26.
Stroes et al., GAUSS-2 Investigators. Anti-PCSK9 antibody effectively lowers cholesterol in patients with statin intolerance: the GAUSS-2 randomized, placebo-controlled phase 3 clinical trial of evolocumab, J Am Coll Cardiol, 63(23): 2541-2548 (2014).
Stroes et al., Statin-associated muscle symptoms: impact on statin therapy-European Atherosclerosis Society Consensus Panel Statement on Assessment, Aetiology and Management Eur Heart J. 36: 1012-1022 (2015).
Sundararaman, et al., 1978, "One step conversion of aldehydes to esters", Tetrahedron Lett. 19:1627-1628.
Suresh, et al., Sample size estimation and power analysis for clinical research studies, Journal of Human Reproductive Sciences 5(1): 7-13 (2012).
Sweeney, 1995, "Comprehensive Organic Functional Group Transformations", Oxford, vol. 2, pp. 104-109.
T. Laird, Development and Scale-up of Processes for the Manufacture of New Pharmaceuticals, in Comprehensive Medicinal Chemistry 321-359 (Corwin Hansch et al. eds., 1990).
Tandon et al. (2003) "p-Toluenesulfonylmethyl Isocyanide: A Versatile Synthon in Organic Chemistry," Sulfur Reports 24(3):307-385.
Taravel, et al., 1988, "Interglycosidic 13C-1H Coupling Constants", Tetrahedron Lett. 29:199-200.
Target Molecule Corp. (TargetMol), ETC1002 (Bempedoic acid), 3 pages, retrieved on Mar. 10, 2021 from <https://www.targetmol.com/compound/ETC1002>.
Teramoto et al. (2013) "Familial Hypercholesterolemia," Journal of Atherosclerosis and Thrombosis 21(1):6-10.
Thompson et al., "Treatment with ETC-1002 along in in combination with ezetimibe lowers LDL cholesterol in hypercholesterolemic patients with or without statin intolerance," 2016, National Lipid Association, Journal of Clinical Lipidology, vol. 10, pp. 556-567.
Thompson et al., Use of ETC-1002 to treat hypercholesterolemia in patients with statin intolerance, J Clin Lipidol 9(3): 295-304 (2015).
Thums et al., "Epoxidation - a Consequence of Cell Damage," Chemical Monthly, 128 (4), 1997, pp. 411-420.
Tontonoz, et al., 1994, "Adipocyte-specific transcription factor ARF6 is a heterodimeric complex of two nuclear hormone receptors, PPAR gamma and RXR alpha", Nucleic Acids Res. 22(5):5628-34.
Toronto Research Chemicals - Bempedoic acid, 5 pages, retrieved on Jul. 13, 2021 from <https://www.trc-canada.com/product-detail/?B119700>.
Torres et al., Tolvaptan in Patients with Autosomal Dominant Polycystic Kidney Disease, N. Engl. J. Med. 367: 2407-2418 (2012).
Toth et al. (2010), A., Tomassini, J. E., & Tershakovec, A. M. (2010). "Update on the efficacy and safety of combination ezetimibe plus statin therapy," Clinical Lipidology, 5(5), 655-684.
Uhlmann, et al., 1986, "Chemical 5'-phosphorylation of oligonucleotides valuable in automated DNA synthesis", Tetrahedron Lett. 27: 1023-26.
Ulrich, et al., 1995, "Cultured hepatocytes as investigational models for hepatic toxicity: practical applications in drug discovery and development", Toxicol Lett. 82/83:107-15.
United States Securities and Exchange Commission Form 10-Q, Esperion Therapeutics, Inc., Filed Nov. 6, 13 for the Period Ending Sep. 30, 13, 54 pages.
United States Securities and Exchange Commission Form 10-Q, Esperion Therapeutics, Inc., Filed Nov. 10, 14 for the Period Ending Sep. 30, 14, 24 pages.
Urata, et al., 1991, "Transition metal complex catalyzed carbonylation of organic halides in the presence of molecular sieves instead of base," Tetrahedron Lett. 32:36, 4733-36.
Vamecq and Draye, 1989, "Pathophysiology of peroxisomal beta-oxidation", Essays Biochem 24:115-225.
Van der Graaf et al. (2008) "Efficacy and safety of coadministration of ezetimibe and simvastatin in adolescents with heterozygous familial hypercholesterolemia," Journal of the American College of Cardiology 52(17): 1421-1429.
van Leusen (1985) "On the synthesis of 1,n-diketones using mono-substituted derivatives of tosylmethyl isocyanide," Recl. Trav. Chim. Pays-Bas 104:50-53.
van Leusen et al. (2001) "Synthetic Uses of Tosylmethyl Isocyanide (TosMIC)" Organic Reactions 417-679.
Varghese Mithun: "Familial hypercholesterolemia: A review", Annals of Pediatric Cardiology, Jan. 1, 2014 (Jan. 1, 2014), XP55795426.
Vippagunta, S. et al., "Crystalline Solids," Advanced Drug Delivery Reviews (2001) vol. 48, pp. 2-26. (abstract only).
Vishwanath et al. (2014) "Familial Hypercholesterolemia and Estimation of US Patients Eligible for Low-Density Lipoprotein Apheresis after Maximally Tolerated Lipid-Lowering Therapy," Journal of Clinical Lipidology 8:18-28.
Vogtle, et al., 1987, "Doubly Clamped Cope Systems", J. Org. Chem. 52:5560-5564.
Vytorin (ezetimibe/simvastatin) label, Febraury 2004.

(56) References Cited

OTHER PUBLICATIONS

Wierzbicki et al., Efficacy of ezetimibe in patients with statin-resistant and statin-intolerant familial hyperlipidaemias, Current Medical Research and Opinion, vol. 21(3): 333-338 (2005).
Williams, et al., 1988, "Bromine as an oxidant for direct conversion of aldehydes to esters", Tetrahedron Lett. 29:5087-90.
Wilson, et al., 1982, "A novel, nonoxidative method for the conversion of aldehydes to esters", J. Org. Chem. 47:1360-61.
Wroblewski and Ladue, 1995, "Lactic dehydrogenase activity in blood", Proc. Soc. Exp. Biol. Med. 90:210-213.
Wu et al., Mechanisms of tolvaptan-induced toxicity in HepG2 cells, Biochem. Pharmacol., 95: 324-336 (2015).
Xu, et al., 1989, "The retinoblastoma susceptibility gene product: a characteristic pattern in normal cells and abnormal expression in malignant cells", Oncogene 4: 807-812.
Yamamoto, "Asymmetric synthesis of 5-and 6-membered lactones from cyclic substrates bearing a C2-chiral auxiliary", J. Org. Chem., 1991, pp. 1112-1119, vol. 35, No. 21.
Yanagisawa, et al., 1994, "Allylbarium Reagents: Unprecedented regio- and stereoselective allylation reactions of carbonyl compounds", J. Am. Chem. Soc 116:6130-6141.
Yang et al. (2004) "Kilogram-Scale Synthesis of Bis(6-hydroxy-5,5-dimethylhexyl)ether (ESP24232), a Novel Lipid Lowering Agent" The New Journal for Organic Synthesis 36(6):587- 596.
Yao Yuan Pharma & Biotech Weekly, vol. 2, Issue No. 10, Oct. 2014.
Yu, et al., 1988, "A novel reagent for the synthesis of myo-inositol phosphates: N,N-diisopropyl dibenzyl phosphoramidite", Tetrahedron Lett. 29:979-82.
Yunker, et al., 1978, "Alpha-oxygenated fatty acids occurring as amides of 2-methylene beta- alanine in a marine sponge", Tetrahedron Lett. 47:4651-52.

* cited by examiner

COMPOSITIONS CONTAINING AND THERAPIES USING BEMPEDOIC ACID AND TOLVAPTAN

CROSS-REFERENCE TO RELATED APPLICATIONS

This application is a U.S. national stage patent application of International Application No. PCT/US2022/031729, filed on Jun. 1, 2022, which claims the benefit of, and priority to, U.S. Patent Application No. 63/195,843, filed on Jun. 2, 2021, and U.S. Patent Application No. 63/275,077, filed on Nov. 3, 2021, the entire contents of each of which are incorporated by reference herein in their entirety.

BACKGROUND

Autosomal dominant polycystic kidney disease (ADPKD) is a serious genetic disorder characterized by growth of cysts in the kidneys and subsequent loss of kidney function. Worldwide, approximately 4 to 7 million individuals are affected by ADPKD, representing a serious health concern (Akoh; *Current management of autosomal dominant polycystic kidney disease*; World J. Nephrol.; 2015; 4(4); 468-79). It is the most common genetic cause of end-stage kidney disease, with a prevalence of 1:500 to 1:1000 and 600,000 patients in the U.S. alone (Gabow; *Autosomal dominant polycystic kidney disease*; The New England Journal of Medicine; 1993; 329; 332-342). Progression of the disease is characterized by enlarging cystic lesions in the kidney and often in the liver and leads to a progressive decline in kidney function, with an associated increase in morbidity and mortality of ADPKD patients (Gabow). Most ADPKD patients have loss-of-function mutations in the polarity protein polycystin-1 (PKD1), and the therapeutic options are limited (Torres et al.; *Tolvaptan in patients with autosomal dominant polycystic kidney disease*; N. Engl. J. Med.; 2012; 367; 2407-2418). As such, the development of new treatment options for ADPKD patients represents an important area of study.

Tolvaptan is the only drug approved by the FDA for treatment of hyponatremia and ADPKD. It functions in the kidneys as an antagonist of vasopressin receptor 2 and causes aquaresis (e.g., excretion of water without significant loss of electrolytes) (Torres). Although tolvaptan is effective at ameliorating the symptoms and slowing the progression of ADPKD, it has a non-ideal safety profile. Specifically, tolvaptan therapy has the dose-dependent side effect of risk of hepatotoxicity, which includes acute liver failure requiring transplantation and fatal liver injury, and therefore requires monthly testing of liver function (Wu et al.; *Mechanisms of tolvaptan-induced toxicity in HepG2 cells*; Biochem. Pharmacol.; 2015; 95; 324-336). The status of tolvaptan as the only FDA-approved drug for the treatment of ADPKD indicates a need for new therapeutics to treat this condition.

Despite the success of tolvaptan, there remains an unmet need for safe and effective treatment options for patients with ADPKD.

SUMMARY

The present disclosure provides combination drug therapies comprising an ATP citrate lyase (ACL) inhibitor (e.g., bempedoic acid) and a vasopressin 2 receptor antagonist (e.g., tolvaptan). The present disclosure also provides methods of using the combination drug therapies described herein, including, for example, for the treatment of autosomal dominant polycystic kidney disease (ADPKD) in a subject in need thereof. The disclosure additionally provides methods of using bempedoic acid as a single agent for the treatment of conditions including ADPKD.

In one aspect, the disclosure provides a fixed-dose combination comprising bempedoic acid and tolvaptan.

In various embodiments of the disclosure, the fixed-dose combination comprises about 30 mg to about 240 mg bempedoic acid. In various embodiments of the disclosure, the fixed-dose combination comprises about 5 mg to about 120 mg tolvaptan; or about 5 mg to about 90 mg tolvaptan.

In some embodiments, the disclosure provides a fixed-dose combination comprising about 30 mg to about 240 mg bempedoic acid and about 5 mg to about 90 mg tolvaptan; and a fixed-dose combination comprising about 30 mg to about 240 mg bempedoic acid and about 5 mg to about 60 mg tolvaptan.

In various embodiments of the disclosure, the fixed-dose combination comprises about 90 mg, about 60 mg, about 45 mg, about 30 mg, about 15 mg, about 10 mg, or about 5 mg tolvaptan. In certain embodiments of the disclosure, the fixed-dose combination comprises about 180 mg bempedoic acid.

In certain embodiments, the disclosure provides a fixed-dose combination comprising about 180 mg bempedoic acid and about 5 mg tolvaptan; a fixed-dose combination comprising about 180 mg bempedoic acid and about 10 mg tolvaptan; a fixed-dose combination comprising about 180 mg bempedoic acid and about 15 mg tolvaptan; a fixed-dose combination comprising about 180 mg bempedoic acid and about 30 mg tolvaptan; a fixed-dose combination comprising about 180 mg bempedoic acid and about 45 mg tolvaptan; a fixed-dose combination comprising about 180 mg bempedoic acid and about 60 mg tolvaptan; and a fixed-dose combination comprising about 180 mg bempedoic acid and about 90 mg tolvaptan.

In various embodiments of the disclosure, the fixed-dose combination is formulated for oral delivery. In certain embodiments of the disclosure, the fixed-dose combination is formulated as an oral solid dosage form selected from the group consisting of a tablet, a capsule, a softgel capsule, a pill, a solution, and a suspension.

In another aspect, the disclosure provides a pharmaceutical composition comprising bempedoic acid, tolvaptan, and one or more pharmaceutically acceptable excipients.

In various embodiments of the disclosure, the pharmaceutical composition comprises about 30 mg to about 240 mg bempedoic acid. In various embodiments, the pharmaceutical composition comprises about 5 mg to about 120 mg tolvaptan; or about 5 mg to about 90 mg tolvaptan.

In some embodiments, the disclosure provides a pharmaceutical composition comprising about 30 mg to about 240 mg bempedoic acid, about 5 mg to about 90 mg tolvaptan, and one or more pharmaceutically acceptable excipients; and a pharmaceutical composition comprising about 30 mg to about 240 mg bempedoic acid, about 5 mg to about 60 mg tolvaptan, and one or more pharmaceutically acceptable excipients.

In various embodiments of the disclosure, the pharmaceutical composition comprises about 90 mg, about 60 mg, about 45 mg, about 30 mg, about 15 mg, about 10 mg, or about 5 mg tolvaptan. In certain embodiments of the disclosure, the pharmaceutical composition comprises about 180 mg bempedoic acid.

In particular embodiments, the disclosure provides a pharmaceutical composition comprising about 180 mg bempedoic acid, about 5 mg tolvaptan, and one or more pharmaceutically acceptable excipients; a pharmaceutical composition comprising about 180 mg bempedoic acid, about 10 mg tolvaptan, and one or more pharmaceutically acceptable excipients; a pharmaceutical composition comprising about 180 mg bempedoic acid, about 15 mg tolvaptan, and one or more pharmaceutically acceptable excipients; a pharmaceutical composition comprising about 180 mg bempedoic acid, about 30 mg tolvaptan, and one or more pharmaceutically acceptable excipients; a pharmaceutical composition comprising about 180 mg bempedoic acid, about 45 mg tolvaptan, and one or more pharmaceutically acceptable excipients; a pharmaceutical composition comprising about 180 mg bempedoic acid, about 60 mg tolvaptan, and one or more pharmaceutically acceptable excipients; and a pharmaceutical composition comprising about 180 mg bempedoic acid, about 90 mg tolvaptan, and one or more pharmaceutically acceptable excipients.

In various embodiments of the disclosure, the pharmaceutical composition is formulated for oral delivery. In certain embodiments of the disclosure, the pharmaceutical composition is formulated as an oral solid dosage form selected from the group consisting of a tablet, a capsule, a softgel capsule, a pill, a solution, and a suspension.

In certain embodiments of the disclosure, the pharmaceutical composition provides immediate release of bempedoic acid. In other embodiments of the disclosure, the pharmaceutical composition provides sustained release of bempedoic acid.

In another aspect, the disclosure provides a method of treating ADPKD in a subject receiving tolvaptan therapy, the method comprising administering to the subject an effective amount of bempedoic acid. In another aspect, the disclosure provides a method of slowing the progression of ADPKD in a subject receiving tolvaptan therapy, the method comprising administering to the subject an effective amount of bempedoic acid. In another aspect, the disclosure provides a method of preventing kidney failure in a subject with ADPKD receiving tolvaptan therapy, the method comprising administering to the subject an effective amount of bempedoic acid.

In various embodiments of the disclosure, the effective amount of bempedoic acid is about 30 mg to about 240 mg. In certain embodiments of the disclosure, the effective amount of bempedoic acid is about 180 mg.

In various embodiments of the disclosure, the subject receiving the effective amount of bempedoic acid and tolvaptan therapy has a lower yearly decrease in estimated glomerular filtration rate than a subject not receiving the effective amount of bempedoic acid and tolvaptan therapy, or receiving only the effective amount of bempedoic acid, or receiving only tolvaptan therapy. In various embodiments of the disclosure, the subject receiving the effective amount of bempedoic acid and tolvaptan therapy has a lower yearly increase in total kidney volume than a subject not receiving the effective amount of bempedoic acid and tolvaptan therapy, or receiving only the effective amount of bempedoic acid, or receiving only tolvaptan therapy. In various embodiments of the disclosure, the subject receiving the effective amount of bempedoic acid and tolvaptan therapy has a lower composite incidence of clinical endpoints selected from worsening kidney function, kidney pain, hypertension, and albuminuria than a subject not receiving the effective amount of bempedoic acid and tolvaptan therapy, or receiving only the effective amount of bempedoic acid, or receiving only tolvaptan therapy.

In various embodiments of the disclosure, the subject receiving the effective amount of bempedoic acid and tolvaptan therapy has higher liver AMPK activity than a subject not receiving the effective amount of bempedoic acid and tolvaptan therapy, or receiving only tolvaptan therapy. In various embodiments of the disclosure, the subject receiving the effective amount of bempedoic acid and tolvaptan therapy has a higher degree of liver acetyl-coenzyme A carboxylase (ACC) phosphorylation than a subject not receiving the effective amount of bempedoic acid and tolvaptan therapy, or receiving only tolvaptan therapy. In various embodiments of the disclosure, the subject receiving the effective amount of bempedoic acid and tolvaptan therapy has a higher degree of peroxisome proliferator-activated receptor gamma coactivator 1-α (PGC1a) activity than a subject receiving only tolvaptan therapy.

In various embodiments of the disclosure, the effective amount of bempedoic acid is delivered orally.

In another aspect, the disclosure provides a method of treating ADPKD in a subject in need thereof, the method comprising administering to the subject a fixed-dose combination of bempedoic acid and tolvaptan, wherein the fixed-dose combination comprises about 30 mg to about 240 mg bempedoic acid and about 5 mg to about 90 mg tolvaptan. In another aspect, the disclosure provides a method of slowing the progression of ADPKD in a subject in need thereof, the method comprising administering to the subject a fixed-dose combination of bempedoic acid and tolvaptan, wherein the fixed-dose combination comprises about 30 mg to about 240 mg bempedoic acid and about 5 mg to about 90 mg tolvaptan. In another aspect, the disclosure provides a method of preventing kidney failure in a subject with ADPKD, the method comprising administering to the subject a fixed-dose combination of bempedoic acid and tolvaptan, wherein the fixed-dose combination comprises about 30 mg to about 240 mg bempedoic acid and about 5 mg to about 90 mg tolvaptan.

In various embodiments of the disclosure, the subject receiving the fixed-dose combination has a lower yearly decrease in estimated glomerular filtration rate than a subject not receiving the fixed-dose combination, or receiving only about 30 mg to about 240 mg bempedoic acid, or receiving only about 5 mg to about 90 mg tolvaptan. In various embodiments of the disclosure, the subject receiving the fixed-dose combination has a lower yearly increase in total kidney volume than a subject not receiving the fixed-dose combination, or receiving only about 30 mg to about 240 mg bempedoic acid, or receiving only about 5 mg to about 90 mg tolvaptan. In various embodiments of the disclosure, the subject receiving the fixed-dose combination has a lower composite incidence of clinical endpoints selected from worsening kidney function, kidney pain, hypertension, and albuminuria than a subject not receiving the fixed-dose combination, or receiving only about 30 mg to about 240 mg bempedoic acid, or receiving only about 5 mg to about 90 mg tolvaptan.

In various embodiments of the disclosure, the subject receiving the fixed-dose combination has higher liver AMPK activity than a subject not receiving the fixed-dose combination, or receiving only about 5 mg to about 90 mg tolvaptan. In various embodiments of the disclosure, the subject receiving the fixed-dose combination has a higher degree of liver ACC phosphorylation than a subject not receiving the fixed-dose combination, or receiving only about 5 mg to about 90 mg tolvaptan. In various embodiments of the disclosure, the subject receiving the fixed-dose combination has a higher degree of peroxisome proliferator-activated receptor gamma coactivator 1-α (PGC1α) activity than a subject receiving only about 5 mg to about 90 mg tolvaptan.

In various embodiments of the disclosure, the fixed-dose combination is delivered orally.

In various embodiments of the disclosure, the fixed-dose combination comprises about 180 mg bempedoic acid. In certain embodiment of the disclosure, the fixed-dose combination comprises about 5 mg, about 10 mg, about 15 mg, about 30 mg, about 45 mg, about 60 mg, or about 90 mg tolvaptan.

In another aspect, the disclosure provides a method of treating ADPKD in a subject in need thereof, the method comprising administering to the subject an effective amount of bempedoic acid and tolvaptan. In another aspect, the disclosure provides a method of slowing the progression of ADPKD in a subject in need thereof, the method comprising administering to the subject an effective amount of bempedoic acid and tolvaptan. In another aspect, the disclosure provides a method of preventing kidney failure in a subject with ADPKD in need thereof, the method comprising administering to the subject an effective amount of bempedoic acid and tolvaptan.

In various embodiments of the disclosure, the effective amount of bempedoic acid and tolvaptan comprises about 30 mg to about 240 mg bempedoic acid. In various embodiments of the disclosure, the effective amount of bempedoic acid and tolvaptan comprises about 180 mg bempedoic acid. In various embodiments of the disclosure, the effective amount of bempedoic acid and tolvaptan comprises about 5 mg, about 10 mg, about 15 mg, about 30 mg, about 45 mg, about 60 mg, or about 90 mg tolvaptan.

In various embodiments of the disclosure, the subject receiving the effective amount of bempedoic acid and tolvaptan has a lower yearly decrease in estimated glomerular filtration rate than a subject receiving a placebo, or receiving only bempedoic acid, or receiving only tolvaptan. In various embodiments of the disclosure, the subject receiving the effective amount of bempedoic acid and tolvaptan has a lower yearly increase in total kidney volume than a subject receiving a placebo, or receiving only bempedoic acid, or receiving only tolvaptan. In various embodiments of the disclosure, the subject receiving the effective amount of bempedoic acid and tolvaptan has a lower composite incidence of clinical endpoints selected from worsening kidney function, kidney pain, hypertension, and albuminuria than a subject receiving a placebo, or receiving only bempedoic acid, or receiving only tolvaptan.

In various embodiments of the disclosure, the subject receiving the effective amount of bempedoic acid and tolvaptan has higher liver AMPK activity than a subject receiving a placebo, or receiving only tolvaptan. In various embodiments of the disclosure, the subject receiving the effective amount of bempedoic acid and tolvaptan has a higher degree of liver ACC phosphorylation than a subject receiving a placebo, or receiving only tolvaptan. In various embodiments of the disclosure, the subject receiving the effective amount of bempedoic acid and tolvaptan has a higher degree of peroxisome proliferator-activated receptor gamma coactivator 1-α (PGC1α) activity than a subject receiving only tolvaptan.

In another aspect, the disclosure provides a method of treating ADPKD in a subject in need thereof, the method comprising administering to the subject an effective amount of bempedoic acid. In another aspect, the disclosure provides a method of slowing the progression of ADPKD in a subject in need thereof, the method comprising administering to the subject an effective amount of bempedoic acid. In another aspect, the disclosure provides a method of preventing kidney failure in a subject with ADPKD, the method comprising administering to the subject an effective amount of bempedoic acid.

In various embodiments of the disclosure, the effective amount bempedoic acid is about 30 mg to about 240 mg. In certain embodiments of the disclosure, the effective amount of bempedoic acid is about 180 mg.

In various embodiments of the disclosure, the subject receiving the effective amount of bempedoic acid has a lower yearly decrease in estimated glomerular filtration rate than a subject receiving a placebo, or has an equivalent or a lower yearly decrease in estimated glomerular filtration rate than a subject receiving tolvaptan therapy. In various embodiments, the subject receiving the effective amount of bempedoic acid has a lower yearly increase in total kidney volume than a subject receiving a placebo, or has an equivalent or a lower yearly increase in total kidney volume than a subject receiving tolvaptan therapy. In various embodiments of the disclosure, the subject receiving the effective amount of bempedoic acid has a lower composite incidence of clinical endpoints selected from worsening kidney function, kidney pain, hypertension, and albuminuria than a subject receiving a placebo, or has an equivalent or a lower composite incidence of clinical endpoints selected from worsening kidney function, kidney pain, hypertension, and albuminuria than a subject receiving tolvaptan therapy. In various embodiments of the disclosure, the effective amount of bempedoic acid is delivered orally.

In various embodiments of the disclosure, the subject is a human.

DETAILED DESCRIPTION

Definitions

Figure 1A:
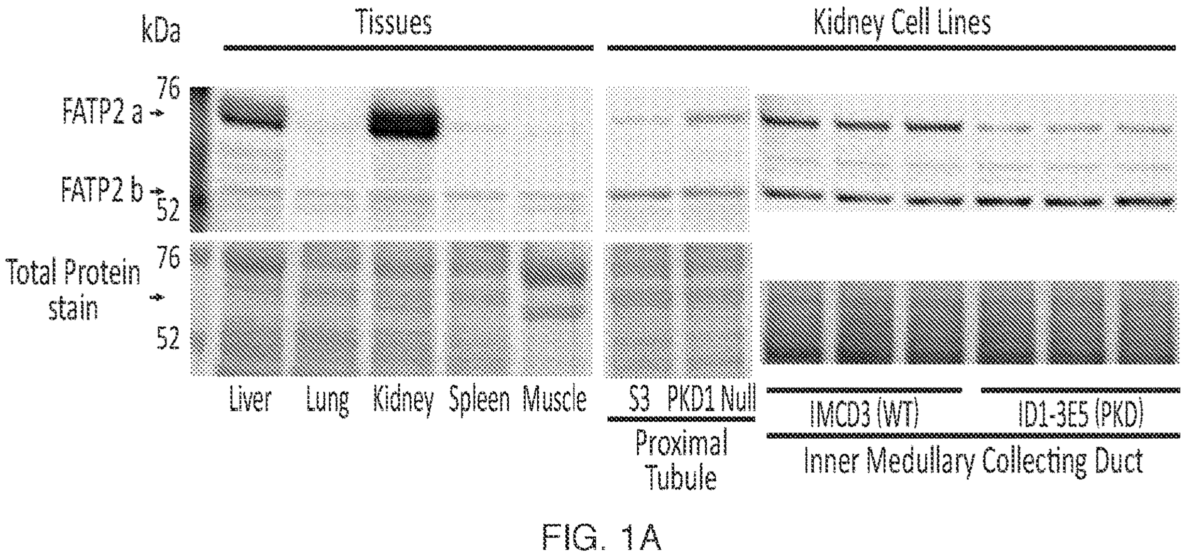
FIG. 1A is an immunoblot assay showing the fatty acid transport protein 2 (FATP2, also known as very long-chain acyl-CoA synthetase (ACSVL1) and/or the gene SLC27A2) protein expression in homogenates of different mouse tissues (liver, lung, kidney, spleen, and muscle), proximal tubule (PT)-derived kidney cell lines (S3, PKD1 Null), and inner medullary collecting duct (IMCD)-derived kidney cell lines (IMCD3 [WT] and ID1-3E5 [PKD]).

To facilitate an understanding of the present disclosure, a number of terms and phrases are defined below.

Unless defined otherwise, all technical and scientific terms used herein have the same meaning as commonly understood by one of ordinary skill in the art to which this disclosure belongs. The abbreviations used herein have their conventional meaning within the chemical and biological arts. The chemical structures and formulae set forth herein are constructed according to the standard rules of chemical valency known in the chemical arts.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments may be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" refers to one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a ±10% variation from the nominal value unless otherwise indicated or inferred from the context.

It should be understood that the order of steps or order for performing certain actions is immaterial so long as the present disclosure remains operable. Moreover, two or more steps or actions may be conducted simultaneously.

At various places in the present specification, variables or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

As a general matter, compositions specifying a percentage are by weight unless otherwise specified. Further, if a variable is not accompanied by a definition, then the previous definition of the variable controls.

As used herein, "pharmaceutical composition" or "pharmaceutical formulation" refers to the combination of an active agent with a carrier, inert or active, making the composition especially suitable for diagnostic or therapeutic use in vivo or ex vivo.

The phrases "pharmaceutically acceptable" and "pharmacologically acceptable," as used herein, refer to compounds, molecular entities, compositions, materials, and/or dosage forms that do not produce an adverse, allergic or other untoward reaction when administered to an animal, or a human, as appropriate. For human administration, preparations should meet sterility, pyrogenicity, and general safety and purity standards as required by regulatory agencies that evaluate the safety and efficacy of pharmaceuticals and drug products, e.g., the U.S. Food and Drug Administration. "Pharmaceutically acceptable" and "pharmacologically acceptable" can mean approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "pharmaceutically acceptable salt" refers to any salt of an acidic or a basic group that may be present in a compound of the present disclosure (e.g., bempedoic acid), which salt is compatible with pharmaceutical administration. For example, one or both of the carboxylic acid groups of bempedoic acid can be transformed to pharmaceutically acceptable salt(s).

As is known to those of skill in the art, "salts" of compounds may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds described herein and their pharmaceutically acceptable acid addition salts.

Examples of bases include, but are not limited to, alkali metal (e.g., sodium and potassium) hydroxides, alkaline earth metal (e.g., magnesium and calcium) hydroxides, ammonia, and compounds of formula $NW_4^+$, wherein W is $C_{1-4}$ alkyl, and the like.

Examples of salts include, but are not limited, to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as $Na^+$, $K^+$, $Ca^{2+}$, $NH_4^+$, and $NW_4^+$ (where W can be a $C_{1-4}$ alkyl group), and the like.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

As used herein, "carrier" refers to a material, composition or vehicle, such as a liquid or solid filler, diluent, excipient, solvent or encapsulating material, involved in carrying or transporting a pharmaceutical agent such as bempedoic acid, or a pharmaceutically acceptable salt thereof, from one organ, or portion of the body, to another organ, or portion of the body.

As used herein, "pharmaceutically acceptable excipient" refers to a substance that aids the administration of an active agent to and/or absorption by a subject and can be included in the compositions of the present disclosure without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's solution, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxypropylmethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. For examples of excipients, see Martin, Remington's Pharmaceutical Sciences, 15th Ed., Mack Publ. Co., Easton, PA (1975).

As used herein, "treat," "treating" or "treatment" includes an action that occurs while a subject is suffering from a specified disease, disorder or condition, which reduces the severity of the disease, disorder or condition, or retards or slows the progression of the disease, disorder or condition (e.g., lessening, reducing, modulating, ameliorating or eliminating, that results in the improvement of the condition, disease, disorder, and the like), or lessens, reduces, modulates, ameliorates or eliminates a symptom thereof. Treating can be curing, improving, or at least partially ameliorating the disorder. In certain embodiments, treating is curing the disease.

As used herein, "reducing" or "reduction" of a symptom or symptoms (and grammatical equivalents of this phrase) refers to decreasing of the severity or frequency of the symptom(s), or elimination of the symptom(s). For example, "reducing" or "reduction" of polycystic kidney disease may refer to a decrease in the rate of kidney cyst growth or a decrease in the rate of loss of kidney function.

As used herein, "reducing" or "reduction" of an elevated laboratory biomarker/parameter or vital sign associated with a disease disclosed herein may refer a decrease in the elevated laboratory biomarker/parameter or vital sign, for example, to a predetermined clinically relevant endpoint (e.g., a clinically normal level).

As used herein, "subject" and "patient" are used interchangeably and refer to an organism to be treated by the methods and compositions of the present disclosure. Such organisms are preferably a mammal (e.g., human, mouse, rat, guinea pig, dog, cat, horse, cow, pig, or non-human primate, such as a monkey, chimpanzee, baboon, and rhesus), and more preferably, a human.

As used herein, "solid dosage form" refers to a pharmaceutical dose(s) in solid form, e.g., tablets, capsules, granules, powders, sachets, reconstitutable powders, dry powder inhalers and chewables.

As used herein, "immediate release" refers to a dosage form that has not been engineered to modify or control the release of the active ingredient.

As used herein, "sustained release" refers to a dosage form designed to release a drug at a predetermined (but not necessarily constant) rate in order to maintain a desired range of drug concentration over a specific period of time, e.g., 8 hours, 12 hours, 16 hours, 20 hours, 24 hours, etc., with minimum side effects. This can be achieved through a variety of formulations, as exemplified by the bempedoic acid sustained release formulations as described in international publication WO 2019/161307A1.

As used herein, "fixed-dose combination" refers to a form in which the active ingredients (e.g., bempedoic acid and tolvaptan) are both administered to a patient simultaneously in the form of a single entity or dosage.

As used herein, "administering" refers to oral administration, administration as a suppository, topical contact, intravenous administration, parenteral administration, intraperitoneal administration, intramuscular administration, intralesional administration, intrathecal administration, intracranial administration, intranasal administration or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., bempedoic acid and tolvaptan). Tolvaptan, or a pharmaceutically acceptable salt thereof, can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

As used herein, "disease," "disorder," "condition," or "illness," which can be used interchangeably herein unless otherwise understood from the context, refers to a state of being or health status of a patient or subject capable of being treated with a compound, pharmaceutical material, pharmaceutical composition, or method provided herein.

As used herein, "effective amount" or "therapeutically-effective amount" refers to the amount of a compound (e.g., bempedoic acid or tolvaptan), a combination of compounds (e.g., bempedoic acid and tolvaptan), a pharmaceutical composition (e.g., a pharmaceutical composition of the present disclosure), or a fixed-dose combination (e.g., a fixed-dose combination of the present disclosure) sufficient to effect beneficial or desired results. An effective amount can be administered in one or more administrations, applications or dosages and is not intended to be limited to a particular formulation or administration route.

Abbreviations:

ADPKD autosomal dominant polycystic kidney disease
PKD polycystic kidney disease
ACL/pACLY ATP citrate lyase/phosphorylated ATP citrate lyase
ACLY ATP citrate lyase
FATP2 fatty acid transport protein 2
ACSVL1 very long-chain acyl-CoA synthetase
BUN blood urea nitrogen
TKV total kidney volume
eGFR estimated glomerular filtration rate
KIM-1 kidney injury molecule-1
AMPK AMP-activated protein kinase
$Thr^{172}/pThr^{172}$ phosphorylated AMPK a
P70S6K/pP70S6K ribosomal protein S6 kinase beta-1/phosphorylated ribosomal protein
S6 kinase beta-1
ERK/pERK extracellular signal-regulated kinase/phosphorylated extracellular
signal-regulated kinase
PKD1 polycystin 1
PT proximal tubule
IMCD inner medullary collecting duct
BA bempedoic acid
HDL-C high-density lipoprotein cholesterol
CRP C-reactive protein
LDL-C low-density lipoprotein-cholesterol
VLDL very-low-density lipoprotein
Alc/hbAlc glycated hemoglobin
hsCRP high-sensitivity C-reactive protein
apo B apolipoprotein B
apo A1 apolipoprotein A1

Bempedoic Acid

Bempedoic acid is a non-statin drug indicated as an adjunct to diet and maximally tolerated statin therapy for the treatment of adults with heterozygous familial hypercholesterolemia or established atherosclerotic cardiovascular disease who require additional lowering of LDL-C. It functions through inhibition of adenosine triphosphate-citrate lyase (ACL). It behaves as a prodrug in vivo, where it is converted to the active species bempedoic acid-CoA by endogenous liver acyl-Coenzyme (CoA) synthetase (ACS) activity. A specific ACS isozyme, very long-chain acyl-CoA synthetase (ACSVL1), is required to form the active species. Bempedoic acid can also activate the metabolic sensor AMPK.

Bempedoic acid is represented by the structure of Formula (I):

(I)

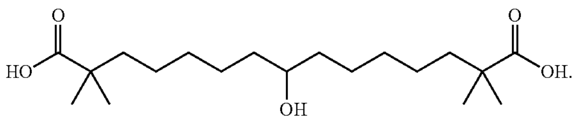

Bempedoic acid and a process for synthesizing it are disclosed in the U.S. Pat. No. 7,335,799 and International Publication No. WO 2020/257571 A1, each of which is herein incorporated by reference. Bempedoic acid may also be referred to as ETC-1002, ESP-55016, or under the tradenames Nexletol®, and Nilemdo® (the latter of which is a fixed-dose combination of bempedoic acid and ezetimibe).

In various embodiments, bempedoic acid, or a pharmaceutically acceptable salt thereof, may be used for the treatment and/or prevention of a variety of diseases and disorders described herein. The methods of treating a disease or disorder generally comprise administering to a patient, in need thereof, a therapeutically effective amount of bempedoic acid, or a pharmaceutically acceptable salt thereof, to treat the disease or disorder.

Examples of diseases and disorders include, but are not limited to, cardiovascular disease, atrial fibrillation, blood clotting, coronary heart disease, hypercoagulable states, ischemia, myocardial infarction, myopathy, myositis, pulmonary embolism, stroke, peripheral vascular disease, dyslipidemia, dyslipoproteinemia, a disorder of glucose metabolism, Alzheimer's disease, Parkinson's disease, diabetic nephropathy, diabetic retinopathy, insulin resistance, metabolic syndrome disorders (e.g., Syndrome X), galactosemia, HIV infection, a peroxisome proliferator activated receptor-associated disorder, septicemia, a thrombotic disorder, obesity, pancreatitis, hypertension, renal disease, cancer, inflammation (e.g., liver inflammation), inflammatory muscle diseases (e.g., polymyalgia rheumatica, polymyositis, and fibrositis), impotence, gastrointestinal disease, irritable bowel syndrome, inflammatory bowel disease, inflammatory disorders (e.g., asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis), arthritis (e.g., rheumatoid arthritis, juvenile rheumatoid arthritis, and osteoarthritis), osteoporosis, soft tissue rheumatism (e.g., tendonitis), bursitis, autoimmune disease (e.g., systemic lupus and erythematosus), scleroderma, ankylosing spondylitis, gout, pseudogout, non-insulin dependent diabetes mellitus, diabetes (e.g., type 2), polycystic ovarian disease, hyperlipidemias (e.g., primary hyperlipidemia, familial hypercholesterolemia (FH), Hypercholesterolemia Frederickson Type IIa, Hypercholesterolemia Frederickson Type IIb, familial combined hyperlipidemia (FCH)), lipoprotein lipase deficiencies (e.g., hypertriglyceridemia, hypoalphalipoproteinemia, and hypercholesterolemia), lipoprotein abnormalities associated with diabetes, lipoprotein abnormalities associated with obesity, and lipoprotein abnormalities associated with Alzheimer's disease. In particular embodiments, the methods include treating and/or preventing hyperlipidemia such as primary hyperlipidemia. In some embodiments, the methods include treating and/or preventing cardiovascular disease.

In certain embodiments, bempedoic acid, or a pharmaceutically acceptable salt thereof, may be used for the treatment or prevention of one or more of high levels of low density lipoprotein cholesterol (LDL-C), high levels of apolipoprotein B (apo B), high levels of lipoprotein(a) (Lp(a)), high levels of very low density lipoprotein (VLDL), high levels of non-high density lipid cholesterol (non-HDL-C), high levels of total serum cholesterol (TC), high levels of high sensitivity c-reactive protein (hsCRP), high levels of fibrinogen, high levels of insulin, high levels of glucose, and low levels of high density lipoprotein cholesterol (HDL-C). In other words, methods of the disclosure can include lowering LDL-C, lowering apo B, lowering Lp(a), lowering VLDL, lowering non-HDL-C, lowering TC, and/or lowering hsCRP. Methods of the disclosure can include inhibiting adenosine triphosphate citrate lyase (ACL), inhibiting cholesterol synthesis, and/or suppressing fatty acid biosynthesis. In some embodiments, bempedoic acid, or a pharmaceutically acceptable salt thereof, may be used for the treatment of non-insulin dependent diabetes mellitus without increasing weight gain.

In certain embodiments, bempedoic acid, or a pharmaceutically acceptable salt thereof, may be used for the treatment or prevention of a variety of diseases and conditions, which include, but are not limited to, aging, Alzheimer's disease, cancer, cardiovascular disease, diabetic nephropathy, diabetic retinopathy, a disorder of glucose metabolism, dyslipidemia, dyslipoproteinemia, enhancing bile production, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, rhabdomyolysis, septicemia, sleep apnea, Syndrome X, and a thrombotic disorder.

In certain embodiments, the disorder is selected from the group consisting of lipodystrophy, lysosomal acid lipase deficiency, and a glycogen storage disease. In some embodiments, the patient is an adult human.

In certain embodiments, bempedoic acid, or a pharmaceutically acceptable salt thereof, may be used for the treatment or prevention of ADPKD.

In certain embodiments, the fixed-dose combinations and pharmaceutical compositions disclosed herein comprise bempedoic acid in its free-acid form.

In certain embodiments, the fixed-dose combinations and pharmaceutical compositions disclosed herein comprise a crystalline form of bempedoic acid.

In certain embodiments, the fixed-dose combinations and pharmaceutical compositions disclosed herein comprise a high purity crystalline form of bempedoic acid.

In certain embodiments, the fixed-dose combinations and pharmaceutical compositions disclosed herein comprise a pharmaceutical material comprising bempedoic acid.

In various embodiments, a pharmaceutical material generally comprises a crystalline form of the compound of formula (I), or a pharmaceutically acceptable salt thereof, wherein the pharmaceutical material comprises the compound of formula (I), or a pharmaceutically acceptable salt thereof, in an amount greater than 99.0% by weight based on the total weight of the pharmaceutical material. In some embodiments, the amount of the compound of formula (I) in the pharmaceutical material is greater than about 99.1%, greater than about 99.2%, greater than about 99.3%, greater than about 99.4%, greater than about 99.5%, greater than about 99.6%, greater than about 99.7%, greater than about 99.8%, greater than about 99.85%, greater than about 99.9%, greater than about 99.95%, or greater than about 99.98% by weight of the total weight of the pharmaceutical material. In some embodiments, the pharmaceutical material comprises the compound of formula (I) in an amount greater than 99.5% by weight based on the total weight of the pharmaceutical material. In some embodiments, the pharmaceutical material comprises the compound of formula (I) in an amount greater than 99.7% by weight based on the total weight of the pharmaceutical material. In some embodiments, the pharmaceutical material comprises the compound of formula (I) in an amount greater than 99.9% by weight based on the total weight of the pharmaceutical material.

In certain embodiments, the pharmaceutical material comprises the compound of formula (I) in an amount of from about 98% to about 102% by weight based on the total weight of the pharmaceutical material (anhydrous, solvent-free basis), as determined by a high-performance liquid chromatography (HPLC) assay.

In certain embodiments, the HPLC assay comprises one or more of.

(i) a Waters XBridge BEH C18 column (4.6 mm i.d. ×150 mm, 2.5 pm);
(ii) a column temperature of about 40° C.;
(iii) a mobile phase comprising about 0.05% phosphoric acid in water/acetonitrile (about 50:50);
(iv) isocratic elution;
(v) a flow rate of about 1.2 mL/minute;
(vi) a sample temperature of ambient temperature;
(vii) detection at 215 nm; and
(viii) the retention time of the compound of formula (I) is about 4.6 minutes. In some embodiments, the HPLC assay comprises each of the above, i.e., (i)-(viii).

In certain embodiments, the crystalline form of the compound of formula (I) may be a crystalline form of the compound of formula (I) as characterized in International Publication Nos. WO2020/257571A1 and WO2020/257573A1, each of which is herein incorporated by reference. A crystalline form of the compound of formula (I) may be characterized, for example, by an X-ray powder diffraction pattern or peak(s), and/or other characteristic properties such as melting point and hygroscopicity. Crystalline forms of bempedoic acid may include, but are not limited to, cocrystals (e.g., an aspartame cocrystal and a palmitic acid cocrystal), crystalline salts (e.g., an ammonium salt, a sodium salt, a potassium salt, a calcium salt, a lysine salt, a diethylamine salt, an ethylenediamine salt, a piperazine salt, a betaine salt, a tromethamine salt, and an isonicotinamide salt).

Tolvaptan

Tolvaptan is a vasopressin receptor 2 antagonist indicated for the treatment of patients with hypervolemic and euvolemic hyponatremia, as well as patients at risk of ADPKD. It aids in hyponatremia by promoting aquaresis, without significant sodium loss, thereby increasing sodium levels in the blood (Dubois et al; Tolvaptan; British J. of Clin. Pharmacol.; 2012; 73(1); 9-11). In ADPKD patients, tolvaptan may slow an increase in kidney volume associated with disease progression, as well as reduce pain and decline in kidney function (Sans-Atxer et al.; *Tolvaptan in the treatment of autosomal dominant polycystic kidney disease; patient selection and special considerations*; J. Nephrol. Renovasc. Dis.; 2018; 11: 41-51).

Tolvaptan may be used in the fixed-dose combinations, pharmaceutical compositions, and methods of treatment described herein. In various embodiments, the fixed-dose combinations and pharmaceutical compositions provided herein comprises tolvaptan, or a pharmaceutically acceptable salt thereof. Tolvaptan is represented by the structure of Formula (II):

(II)

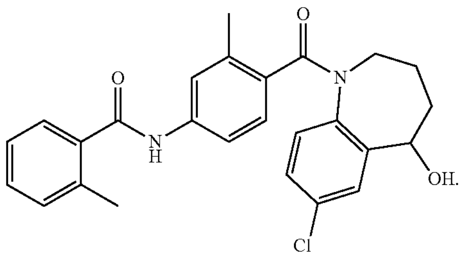

Tolvaptan and its process of manufacture are disclosed in, for example, U.S. Pat. Nos. 8,501,730 and 10,905,694, which are incorporated herein by reference. Tolvaptan may be administered as an oral dosage form. Tolvaptan may also be referred to under the names of OPC-41061, Jynarque® and Samsca®.

In various embodiments, tolvaptan, or a pharmaceutically acceptable salt thereof, may be used for the treatment or prevention of a variety of diseases and disorders described herein. The methods of preventing or treating a disease or disorder generally comprise administering to a patient in need thereof, a therapeutically effective amount of tolvaptan, or a pharmaceutically acceptable salt thereof, to prevent or treat the disease or disorder.

Examples of diseases and disorders include, but are not limited to, hyponatremia and ADPKD.

In certain embodiments, the fixed-dose combinations and pharmaceutical compositions disclosed herein comprise tolvaptan in its free-acid/free-base form.

Fixed-Dose Combinations

Disclosed herein are fixed-dose combinations generally comprising bempedoic acid and tolvaptan.

In some embodiments, the fixed-dose combination comprises about 30 mg to about 300 mg, about 60 mg to about 300 mg, about 90 mg to about 300 mg, about 120 mg to about 300 mg, about 150 mg to about 300 mg, about 180 mg to about 300 mg, about 210 mg to about 300 mg, about 240 mg to about 300 mg, about 270 mg to about 300 mg, about 30 mg to about 270 mg, about 60 mg to about 270 mg, about 90 mg to about 270 mg, about 120 mg to about 270 mg, about 150 mg to about 270 mg, about 180 mg to about 270 mg, about 210 mg to about 270 mg, about 240 mg to about 270 mg, about 30 mg to about 240 mg, about 60 mg to about 240 mg, about 90 mg to about 240 mg, about 120 mg to about 240 mg, about 150 mg to about 240 mg, about 180 mg to about 240 mg, about 210 mg to about 240 mg, about 30 mg to about 210 mg, about 60 mg to about 210 mg, about 90 mg to about 210 mg, about 120 mg to about 210 mg, about 150 mg to about 210 mg, about 180 mg to about 210 mg, about 30 mg to about 180 mg, about 60 mg to about 180 mg, about 90 mg to about 180 mg, about 120 mg to about 180 mg, about 150 mg to about 180 mg, about 30 mg to about 150 mg, about 60 mg to about 150 mg, about 90 mg to about 150 mg, about 120 mg to about 150 mg, about 30 mg to about 120 mg, about 60 mg to about 120 mg, about 90 mg to about 120 mg, about 30 mg to about 90 mg, about 60 mg to about 90 mg, or about 30 mg to about 60 mg bempedoic acid. In some embodiments, the fixed-dose combination comprises about 30 mg to about 240 mg. In some embodiments, the fixed-dose combination comprises about 120 mg to about 240 mg bempedoic acid.

In some embodiments, the fixed-dose combination comprises about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg bempedoic acid.

In some embodiments, the fixed-dose combination comprises about 5 mg to about 120 mg, about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 20 mg, about 5 mg to about 10 mg, about 15 mg to about 90 mg, about 15 mg to about 80 mg, about 15 mg to about 70 mg, about 15 mg to about 60 mg, about 15 mg to about 50 mg, about 15 mg to about 40 mg, about 15 mg to about 30 mg, about 15 mg to about 20 mg, about 25 mg to about 90 mg, about 35 mg to about 90 mg, about 45 mg to about 90 mg, about 55 mg to about 90 mg, about 65 mg to about 90 mg, about 75 mg to about 90 mg, about 85 mg to about 90 mg, about 10 mg to about 110 mg, about 15 mg to about 105 mg, about 20 mg to about 100 mg, about 25 mg to about 95 mg, about 30 mg to about 90 mg, about 35 mg to about 85 mg, about 40 mg to about 80 mg, about 45 mg to about 75 mg, about 50 mg to about 70 mg, or about 55 mg to about 65 mg tolvaptan. In some embodiments, the fixed-dose combination comprises about 5 mg to about 120 mg tolvaptan. In some embodiments, the fixed-dose combination comprises about 5 to about 90 mg tolvaptan.

In some embodiments, the fixed-dose combination comprises about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, or about 120 mg tolvaptan.

In certain embodiments, the fixed-dose combination comprises about 30 mg to about 240 mg bempedoic acid and about 5 mg to about 90 mg tolvaptan. In certain embodiments, the fixed-dose combination comprises about 120 mg to about 240 mg bempedoic acid and about 5 mg to about 90 mg tolvaptan. In certain embodiments, the fixed-dose combination comprises about 30 mg to about 240 mg bempedoic acid and about 5 mg to about 60 mg tolvaptan. In certain embodiments, the fixed-dose combination comprises about 120 mg to about 240 mg bempedoic acid and about 5 mg to about 60 mg tolvaptan.

In some embodiments, the fixed-dose combination comprises about 90 mg, about 60 mg, about 45 mg, about 30 mg, about 15 mg, about 10 mg, or about 5 mg tolvaptan. In certain embodiments, the fixed-dose combination comprises about 180 mg bempedoic acid.

In particular embodiments, the fixed-dose combination comprises about 180 mg bempedoic acid and about 5 mg tolvaptan; about 180 mg bempedoic acid and about 10 mg tolvaptan; about 180 mg bempedoic acid and about 15 mg tolvaptan; about 180 mg bempedoic acid and about 30 mg tolvaptan; about 180 mg bempedoic acid and about 45 mg tolvaptan; about 180 mg bempedoic acid and about 60 mg tolvaptan; or about 180 mg bempedoic acid and about 90 mg tolvaptan.

In some embodiments, the fixed-dose combinations disclosed herein are formulated for oral delivery. In some embodiments, the fixed-dose combinations disclosed herein are formulated as an oral dosage form. Examples of oral dosage forms include, but are not limited to, a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the fixed-dose combination is formulated as a tablet.

In certain embodiments, a liquid dosage form of the fixed-dose combinations described herein comprises one of the following: an inert diluent, a solubilizing agent, and an emulsifier. In certain embodiments, oral suspensions of a pharmaceutical composition of the disclosure comprise one or more suspending agents including, but not limited to, an ethoxylated isostearyl alcohol, a polyoxyethylene sorbitol and sorbitan ester, a microcrystalline cellulose, an aluminum metahydroxide, bentonite, agar-agar and tragacanth, and mixtures thereof.

In certain embodiments, the fixed-dose combinations provided herein can be used for the treatment of a disease, disorder, or condition described herein.

Pharmaceutical Compositions

Also disclosed herein are pharmaceutical compositions generally comprising bempedoic acid and/or tolvaptan, and one or more pharmaceutically acceptable excipients.

In certain embodiments, the pharmaceutical compositions described herein may be administered in a unit dosage form and may be prepared by any method well known in the art of pharmacy. The amounts of the compounds of bempedoic acid and tolvaptan, or pharmaceutically acceptable salts thereof, present in a single dosage form may vary depending upon the patient being treated and/or the particular mode of administration.

In certain embodiments, tolvaptan and bempedoic acid can be combined in a single pharmaceutical composition for simultaneous administration. In certain embodiments, tolvaptan and bempedoic acid can be formulated as individual pharmaceutical compositions for separate administration.

In certain embodiments, the amount of bempedoic acid and tolvaptan, or pharmaceutically acceptable salts thereof, that can be combined with a pharmaceutically acceptable carrier to produce a single dosage form will generally be an amount of the compound of bempedoic acid and tolvaptan, or pharmaceutically acceptable salts thereof, that produces a therapeutic effect.

In some embodiments, the pharmaceutical composition comprises about 30 mg to about 300 mg, about 60 mg to about 300 mg, about 90 mg to about 300 mg, about 120 mg to about 300 mg, about 150 mg to about 300 mg, about 180 mg to about 300 mg, about 210 mg to about 300 mg, about 240 mg to about 300 mg, about 270 mg to about 300 mg, about 30 mg to about 270 mg, about 60 mg to about 270 mg, about 90 mg to about 270 mg, about 120 mg to about 270 mg, about 150 mg to about 270 mg, about 180 mg to about 270 mg, about 210 mg to about 270 mg, about 240 mg to about 270 mg, about 30 mg to about 240 mg, about 60 mg to about 240 mg, about 90 mg to about 240 mg, about 120 mg to about 240 mg, about 150 mg to about 240 mg, about 180 mg to about 240 mg, about 210 mg to about 240 mg, about 30 mg to about 210 mg, about 60 mg to about 210 mg, about 90 mg to about 210 mg, about 120 mg to about 210 mg, about 150 mg to about 210 mg, about 180 mg to about 210 mg, about 30 mg to about 180 mg, about 60 mg to about 180 mg, about 90 mg to about 180 mg, about 120 mg to about 180 mg, about 150 mg to about 180 mg, about 30 mg to about 150 mg, about 60 mg to about 150 mg, about 90 mg to about 150 mg, about 120 mg to about 150 mg, about 30 mg to about 120 mg, about 60 mg to about 120 mg, about 90 mg to about 120 mg, about 30 mg to about 90 mg, about 60 mg to about 90 mg, or about 30 mg to about 60 mg bempedoic acid. In some embodiments, the pharmaceutical composition comprises about 30 mg to about 240 mg bempedoic acid. In some embodiments, the pharmaceutical composition comprises about 120 mg to about 240 mg bempedoic acid.

In some embodiments, the pharmaceutical composition comprises about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg bempedoic acid.

In some embodiments, the pharmaceutical composition comprises about 5 mg to about 120 mg, about 5 mg to about 110 mg, about 5 mg to about 100 mg, about 5 mg to about 90 mg, about 5 mg to about 80 mg, about 5 mg to about 70 mg, about 5 mg to about 60 mg, about 5 mg to about 50 mg, about 5 mg to about 40 mg, about 5 mg to about 30 mg, about 5 mg to about 20 mg, about 5 mg to about 10 mg, about 15 mg to about 90 mg, about 15 mg to about 80 mg, about 15 mg to about 70 mg, about 15 mg to about 60 mg, about 15 mg to about 50 mg, about 15 mg to about 40 mg, about 15 mg to about 30 mg, about 15 mg to about 20 mg, about 25 mg to about 90 mg, about 35 mg to about 90 mg, about 45 mg to about 90 mg, about 55 mg to about 90 mg, about 65 mg to about 90 mg, about 75 mg to about 90 mg, about 85 mg to about 90 mg, about 10 mg to about 110 mg, about 15 mg to about 105 mg, about 20 mg to about 100 mg, about 25 mg to about 95 mg, about 30 mg to about 90 mg, about 35 mg to about 85 mg, about 40 mg to about 80 mg, about 45 mg to about 75 mg, about 50 mg to about 70 mg, or about 55 mg to about 65 mg tolvaptan. In some embodiments, the pharmaceutical composition comprises about 5 mg to about 120 mg tolvaptan. In some embodiments, the pharmaceutical composition comprises about 5 to about 90 mg tolvaptan.

In some embodiments, the pharmaceutical composition comprises about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, or about 120 mg tolvaptan.

In certain embodiments, the pharmaceutical composition comprises about 30 mg to about 240 mg bempedoic acid, about 5 mg to about 90 mg tolvaptan, and one or more pharmaceutically acceptable excipients. In certain embodiments, the pharmaceutical composition comprises about 120 mg to about 240 mg bempedoic acid, about 5 mg to about 90 mg tolvaptan, and one or more pharmaceutically acceptable excipients. In certain embodiments, the pharmaceutical composition comprises about 30 mg to about 240 mg bempedoic acid, about 5 mg to about 60 mg tolvaptan, and one or more pharmaceutically acceptable excipients. In certain embodiments, the pharmaceutical composition comprises about 120 mg to about 240 mg bempedoic acid, about 5 mg to about 60 mg tolvaptan, and one or more pharmaceutically acceptable excipients.

In some embodiments, the pharmaceutical composition comprises about 90 mg, about 60 mg, about 45 mg, about 30 mg, about 15 mg, about 10 mg, or about 5 mg tolvaptan. In certain embodiments, the pharmaceutical composition comprises about 180 mg bempedoic acid.

In particular embodiments, the pharmaceutical composition comprises about 180 mg bempedoic acid, about 5 mg tolvaptan, and one or more pharmaceutically acceptable excipients; about 180 mg bempedoic acid, about 10 mg tolvaptan, and one or more pharmaceutically acceptable excipients; about 180 mg bempedoic acid, about 15 mg tolvaptan, and one or more pharmaceutically acceptable excipients; about 180 mg bempedoic acid, about 30 mg tolvaptan, and one or more pharmaceutically acceptable excipients; about 180 mg bempedoic acid, about 45 mg tolvaptan, and one or more pharmaceutically acceptable excipients; about 180 mg bempedoic acid, about 60 mg tolvaptan, and one or more pharmaceutically acceptable excipients; or about 180 mg bempedoic acid, about 90 mg tolvaptan, and one or more pharmaceutically acceptable excipients.

In certain embodiments, a pharmaceutical composition generally comprises a fixed-dose combination described herein and one or more pharmaceutically acceptable excipients.

In certain embodiments, the solid dosage forms described herein to be used for oral administration are prepared by mixing a pharmaceutical material with one or more pharmaceutically acceptable excipients. Pharmaceutical excipients can be selected from the group consisting of a filler or extender, a sweetening agent, a binder, a humectant, a disintegrating agent, a preservative, a perfuming agent, a flavoring agent, an antioxidant, a solution retarding agent, an absorption accelerator, a wetting agent, an absorbent, a lubricant, a coloring agent, and a controlled release agent. In some embodiments, when the solid dosage form is a capsule, a tablet or a pill, the pharmaceutical compositions described herein may also comprise a buffering agent. In some embodiments, when the solid dosage form is a gelatin capsule, the pharmaceutical composition may further comprise one or more excipients selected from lactose, a milk sugar, a high molecular weight polyethylene glycol and combinations thereof.

In certain embodiments, a pharmaceutical composition of the disclosure may comprise one or more excipients selected from the group consisting of a cyclodextrin, a cellulose, a liposome, a micelle forming agent, and a polymeric carrier. In some embodiments, the pharmaceutical compositions of the present disclosure comprise an antibacterial agent, an antifungal agent, or combinations thereof. Examples of antibacterial and antifungal agents include, but are not limited to, paraben, chlorobutanol, phenol and sorbic acid. In some embodiments, the pharmaceutical compositions of the present disclosure comprise an isotonic agent.

In some embodiments, the pharmaceutical compositions disclosed herein are formulated for oral delivery. In some embodiments, the pharmaceutical compositions disclosed herein are formulated as an oral dosage form. Examples of oral dosage forms include, but are not limited to a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical composition is formulated as a tablet.

In certain embodiments, a liquid dosage form of the pharmaceutical compositions described herein comprises one of the following: an inert diluent, a solubilizing agent, and an emulsifier. In certain embodiments, oral suspensions of a pharmaceutical composition of the disclosure comprise one or more suspending agents including an ethoxylated isostearyl alcohol, a polyoxyethylene sorbitol and sorbitan ester, a microcrystalline cellulose, an aluminum metahydroxide, bentonite, agar-agar and tragacanth, and mixtures thereof.

In some embodiments, the pharmaceutical compositions disclosed herein provide immediate release of bempedoic acid. In some embodiments, the pharmaceutical compositions disclosed herein provide sustained release of bempedoic acid.

In certain embodiments, a pharmaceutical composition described herein can be used for the treatment of a disease, disorder, or condition described herein.

Methods of Use and Treatments

Provided herein are methods of treating ADPKD in a subject receiving tolvaptan therapy, the methods comprising administering to the subject an effective amount of bempedoic acid. Also provided herein are methods of slowing the progression of ADPKD in a subject receiving tolvaptan therapy, the methods comprising administering to the subject an effective amount of bempedoic acid. Also provided herein are methods of preventing kidney failure, reducing total kidney volume, and/or slowing the progression of kidney dysfunction in a subject with ADPKD receiving tolvaptan therapy, the methods comprising administering to the subject an effective amount of bempedoic acid.

In some embodiments, the effective amount of bempedoic acid is about 30 mg to about 240 mg. In some embodiments, the effective amount of bempedoic acid is about 120 mg to about 240 mg. In certain embodiments, the effective amount of bempedoic acid is about 180 mg.

In some embodiments, the subject receiving the effective amount of bempedoic acid and tolvaptan therapy has a lower total kidney weight to body weight ratio than a subject not receiving the effective amount of bempedoic acid and tolvaptan therapy, or receiving only the effective amount of bempedoic acid, or receiving only tolvaptan therapy. In some embodiments, the subject receiving the effective amount of bempedoic acid and tolvaptan therapy has a lower blood urea nitrogen level than a subject not receiving the effective amount of bempedoic acid and tolvaptan therapy, or receiving only the effective amount of bempedoic acid, or receiving only tolvaptan therapy.

In some embodiments, the subject receiving the effective amount of bempedoic acid and tolvaptan therapy has a total kidney weight to body weight ratio about 10 to about 140 percent, about 20 to about 140 percent, about 30 to about 140 percent, about 40 to about 140 percent, about 50 to about 140 percent, about 60 to about 140 percent, about 70 to about 140 percent, about 80 to about 140 percent, about 90 to about 140 percent, about 100 to about 140 percent, about 110 to about 140 percent, about 120 to about 140 percent, about 130 to about 140 percent, about 10 to about 80 percent, about 10 to about 70 percent, about 10 to about 60 percent, about 10 to about 50 percent, about 10 to about 40 percent, about 10 to about 30 percent, about 10 to about 20 percent, about 30 to about 70 percent, about 40 to about 70 percent, about 50 to about 70 percent, about 60 to about 70 percent, about 40 to about 60 percent, about 40 to about 50 percent, about 10 to about 20 percent, about 20 to about 30 percent, about 30 to about 40 percent, about 40 to about 50 percent, about 50 percent to about 60 percent, about 60 percent to about 70 percent, about 70 percent to about 80 percent, about 80 percent to about 90 percent, about 90 to about 100 percent, about 100 to about 110 percent, about 110 to about 120 percent, about 120 to about 130 percent, or about 130 percent to about 140 percent lower than the total kidney weight to body weight ratio of a subject not receiving the effective amount of bempedoic acid and tolvaptan therapy, or receiving only the effective amount of bempedoic acid, or receiving only tolvaptan therapy.

In some embodiments, the subject receiving the effective amount of bempedoic acid and tolvaptan therapy has a blood urea nitrogen (BUN) level about 2 to about 15 mg/dL, about 3 to about 15 mg/dL, about 4 to about 15 mg/dL, about 5 to about 15 mg/dL, about 6 to about 15 mg/dL, about 7 to about 15 mg/dL, about 8 to about 15 mg/dL, about 9 to about 15 mg/dL, about 10 to about 15 mg/dL, about 11 to about 15 mg/dL, about 12 to about 15 mg/dL, about 13 to about 15 mg/dL, about 14 to about 15 mg/dL, about 2 to about 14 mg/dL, about 2 to about 13 mg/dL, about 2 to about 12 mg/dL, about 2 to about 11 mg/dL, about 2 to about 10 mg/dL, about 2 to about 9 mg/dL, about 2 to about 8 mg/dL, about 2 to about 7 mg/dL, about 2 to about 6 mg/dL, about 2 to about 5 mg/dL, about 2 to about 4 mg/dL, about 2 to about 3 mg/dL, about 3 to about 9 mg/dL, about 4 to about 9 mg/dL, about 5 to about 9 mg/dL, about 6 to about 9 mg/dL, about 7 to about 9 mg/dL, about 8 to about 9 mg/dL, about 3 to about 8 mg/dL, about 3 to about 7 mg/dL, about 3 to about 6 mg/dL, about 3 to about 5 mg/dL, or about 3 to about 4 mg/dL lower than the BUN of a subject not receiving the effective amount of bempedoic acid and tolvaptan therapy, or receiving only the effective amount of bempedoic acid, or receiving only tolvaptan therapy.

In some embodiments, the subject receiving the effective amount of bempedoic acid and tolvaptan therapy has a decrease in estimated glomerular filtration rate (eGFR) of about 0.5 to about 5 mL/min/1.73 $m^2$/year, about 1 to about 5 mL/min/1.73 $m^2$/year, about 1.5 to about 5 mL/min/1.73 $m^2$/year, about 2 to about 5 mL/min/1.73 $m^2$/year, about 2.5 to about 5 mL/min/1.73 $m^2$/year, about 3 to about 5 mL/min/1.73 $m^2$/year, about 3.5 to about 5 mL/min/1.73 $m^2$/year, about 4 to about 5 mL/min/1.73 $m^2$/year, about 4.5 to about 5 mL/min/1.73 $m^2$/year, about 0.5 to about 4.5 mL/min/1.73 $m^2$/year, about 0.5 to about 4 mL/min/1.73 $m^2$/year, about 0.5 to about 3.5 mL/min/1.73 $m^2$/year, about 0.5 to about 3 mL/min/1.73 $m^2$/year, about 0.5 to about 2.5 mL/min/1.73 $m^2$/year, about 0.5 to about 2 mL/min/1.73 $m^2$/year, about 0.5 to about 1.5 mL/min/1.73 $m^2$/year, about 0.5 to about 1 mL/min/1.73 $m^2$/year, about 1.7 to about 3.4 mL/min/1.73 $m^2$/year, about 1.9 to about 3.4 mL/min/1.73 $m^2$/year, about 2.1 to about 3.4 mL/min/1.73 $m^2$/year, about 2.3 to about 3.4 mL/min/1.73 $m^2$/year, about 2.5 to about 3.4 mL/min/1.73 $m^2$/year, about 2.7 to about 3.4 mL/min/1.73 $m^2$/year, about 2.9 to about 3.4 mL/min/1.73 $m^2$/year, about 3.1 to about 3.4 mL/min/1.73 $m^2$/year, about 3.3 to about 3.4 mL/min/1.73 $m^2$/year, about 1.7 to about 1.9 mL/min/1.73 $m^2$/year, about 1.9 to about 2.1 mL/min/1.73 $m^2$/year, about 2.1 to about 2.3 mL/min/1.73 $m^2$/year, about 2.3 to about 2.5 mL/min/1.73 $m^2$/year, about 2.5 to about 2.7 mL/min/1.73 $m^2$/year, about 2.7 to about 2.9 mL/min/1.73 $m^2$/year, about 2.9 to about 3.1 mL/min/1.73 $m^2$/year, about 3.1 to about 3.3 mL/min/1.73 $m^2$/year, or about 3.3 to about 3.4 mL/min/1.73 $m^2$/year lower than the decrease in eGFR per year of a subject not receiving the effective amount of bempedoic acid and tolvaptan therapy, or receiving only the effective amount of bempedoic acid, or receiving only tolvaptan therapy.

In some embodiments, the subject receiving the effective amount of bempedoic acid and tolvaptan therapy has an increase in total kidney volume of about 0 to about 7 percent/year, about 0.5 to about 7 percent/year, about 1 to about 7 percent/year, about 1.5 to about 7 percent/year, about 2 to about 7 percent/year, about 2.5 to about 7 percent/year, about 3 to about 7 percent/year, about 3.5 to about 7 percent/year, about 4 to about 7 percent/year, about 4.5 to about 7 percent/year, about 5 to about 7 percent/year, about 5.5 to about 7 percent/year, about 6 to about 7 percent/year, about 6.5 to about 7 percent/year, about 0 to about 6.5 percent/year, about 0 to about 6 percent/year, about 0 to about 5.5 percent/year, about 0 to about 5 percent/year, about 0 to about 4.5 percent/year, about 0 to about 4 percent/year, about 0 to about 3.5 percent/year, about 0 to about 3 percent/year, about 0 to about 2.5 percent/year, about 0 to about 2 percent/year, about 0 to about 1.5 percent/year, about 0 to about 1 percent/year, about 0 to about 0.5 percent/year, about 1 to about 5 percent/year, about 1.5 to about 5 percent/year, about 2 to about 5 percent/year, about 2.5 to about 5 percent/year, about 3 to about 5 percent/year, about 3.5 to about 5 percent/year, about 4 to about 5 percent/year, about 4.5 to about 5 percent/year, about 1 to about 1.5 percent/year, about 1.5 to about 2 percent/year, about 2 to about 2.5 percent/year, about 2.5 to about 3 percent/year, about 3 to about 3.5 percent/year, about 3.5 to about 4 percent/year, about 4 to about 4.5 percent/year, or about 4.5 to about 5 percent/year lower than the percent/year increase in total kidney volume of a subject not receiving the effective amount of bempedoic acid and tolvaptan therapy, or receiving only the effective amount of bempedoic acid, or receiving only tolvaptan therapy.

In some embodiments, the subject receiving the effective amount of bempedoic acid and tolvaptan therapy has a composite incidence of clinical endpoints selected from worsening kidney function, kidney pain, hypertension, and albuminuria of about 5 to about 50 percent, about 10 to about 50 percent, about 15 to about 50 percent, about 20 to about 50 percent, about 25 to about 50 percent, about 30 to about 50 percent, about 35 to about 50 percent, about 40 to about 50 percent, about 45 to about 50 percent, about 5 to about 45 percent, about 5 to about 40 percent, about 5 to about 35 percent, about 5 to about 30 percent, about 5 to about 25 percent, about 5 to about 20 percent, about 5 to about 15 percent, about 5 to about 10 percent, about 15 to about 40 percent, about 20 to about 40 percent, about 25 to about 40 percent, about 30 to about 40 percent, about 35 to about 40 percent, about 15 to about 20 percent, about 20 to about 25 percent, about 25 to about 30 percent, about 30 to about 35 percent, or about 35 to about 40 percent lower than the composite incidence of clinical endpoints of a subject not receiving the effective amount of bempedoic acid and tolvaptan therapy, or receiving only the effective amount of bempedoic acid, or receiving only tolvaptan therapy.

In some embodiments, the subject receiving the effective amount of bempedoic acid and tolvaptan therapy has higher liver AMPK activity than a subject not receiving the effective amount of bempedoic acid, or receiving only tolvaptan therapy. In some embodiments, the subject receiving the effective amount of bempedoic acid and tolvaptan therapy has a higher degree of liver acetyl-coenzyme A carboxylase (ACC) phosphorylation than a subject not receiving the effective amount of bempedoic acid, or receiving only tolvaptan therapy. In some embodiments, the subject receiving the effective amount of bempedoic acid and tolvaptan therapy has a higher degree of peroxisome proliferator-activated receptor gamma coactivator 1-α (PGC1α) activity than a subject receiving only tolvaptan therapy.

In some embodiments, the effective amount of bempedoic acid is delivered orally. Examples of oral dosage forms include, but are not limited to a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical composition is formulated as a tablet.

Also provided herein are methods of treating ADPKD in a subject in need thereof, the methods comprising administering to the subject a fixed-dose combination of bempedoic acid and tolvaptan, wherein the fixed-dose combination comprises about 30 mg to about 240 mg bempedoic acid and about 5 mg to about 90 mg tolvaptan. Also provided herein are methods of treating ADPKD in a subject in need thereof, the methods comprising administering to the subject a fixed-dose combination of bempedoic acid and tolvaptan, wherein the fixed-dose combination comprises about 120 mg to about 240 mg bempedoic acid and about 5 mg to about 90 mg tolvaptan. Also provided herein are methods of slowing the progression of ADPKD in a subject in need thereof, the methods comprising administering to the subject a fixed-dose combination of bempedoic acid and tolvaptan, wherein the fixed-dose combination comprises about 30 mg to about 240 mg bempedoic acid and about 5 mg to about 90 mg tolvaptan. Also provided herein are methods of slowing the progression of ADPKD in a subject in need thereof, the methods comprising administering to the subject a fixed-dose combination of bempedoic acid and tolvaptan, wherein the fixed-dose combination comprises about 120 mg to about 240 mg bempedoic acid and about 5 mg to about 90 mg tolvaptan. Also provided herein are methods of preventing kidney failure, reducing total kidney volume, and/or slowing the progression of kidney dysfunction in a subject with ADPKD, the methods comprising administering to the subject a fixed-dose combination of bempedoic acid and tolvaptan, wherein the fixed-dose combination comprises about 30 mg to about 240 mg bempedoic acid and about 5 mg to about 90 mg tolvaptan. Also provided herein are methods of preventing kidney failure, reducing total kidney volume, and/or slowing the progression of kidney dysfunction in a subject with ADPKD, the methods comprising administering to the subject a fixed-dose combination of bempedoic acid and tolvaptan, wherein the fixed-dose combination comprises about 120 mg to about 240 mg bempedoic acid and about 5 mg to about 90 mg tolvaptan.

In some embodiments, the subject receiving the fixed-dose combination has a lower total kidney weight to body weight ratio than a subject not receiving the fixed-dose combination, or receiving only about 30 mg to about 240 mg bempedoic acid, or receiving only about 5 mg to about 90 mg tolvaptan. In some embodiments, the subject receiving the fixed-dose combination has a lower total kidney weight to body weight ratio than a subject not receiving the fixed-dose combination, or receiving only about 120 mg to about 240 mg bempedoic acid, or receiving only about 5 mg to about 90 mg tolvaptan. In some embodiments, the subject receiving the fixed-dose combination has a lower blood urea nitrogen level than a subject not receiving the fixed-dose combination, or receiving only about 30 mg to about 240 mg bempedoic acid, or receiving only about 5 mg to about 90 mg tolvaptan. In some embodiments, the subject receiving the fixed-dose combination has a lower blood urea nitrogen level than a subject not receiving the fixed-dose combination, or receiving only about 120 mg to about 240 mg bempedoic acid, or receiving only about 5 mg to about 90 mg tolvaptan.

In some embodiments, the subject receiving the fixed-dose combination has a total kidney weight to body weight ratio about 10 to about 140 percent, about 20 to about 140 percent, about 30 to about 140 percent, about 40 to about 140 percent, about 50 to about 140 percent, about 60 to about 140 percent, about 70 to about 140 percent, about 80 to about 140 percent, about 90 to about 140 percent, about 100 to about 140 percent, about 110 to about 140 percent, about 120 to about 140 percent, about 130 to about 140 percent, about 10 to about 80 percent, about 10 to about 70 percent, about 10 to about 60 percent, about 10 to about 50 percent, about 10 to about 40 percent, about 10 to about 30 percent, about 10 to about 20 percent, about 30 to about 70 percent, about 40 to about 70 percent, about 50 to about 70 percent, about 60 to about 70 percent, about 40 to about 60 percent, about 40 to about 50 percent, about 10 to about 20 percent, about 20 to about 30 percent, about 30 to about 40 percent, about 40 to about 50 percent, about 50 percent to about 60 percent, about 60 percent to about 70 percent, about 70 percent to about 80 percent, about 80 percent to about 90 percent, about 90 to about 100 percent, about 100 to about 110 percent, about 110 to about 120 percent, about 120 to about 130 percent, or about 130 percent to about 140 percent lower than the total kidney weight to body weight ratio of a subject not receiving the fixed-dose combination, or receiving only about 30 mg to about 240 mg bempedoic acid, or receiving only about 5 mg to about 90 mg tolvaptan.

In some embodiments, the subject receiving the fixed-dose combination has a total kidney weight to body weight ratio about 10 to about 140 percent, about 20 to about 140 percent, about 30 to about 140 percent, about 40 to about 140 percent, about 50 to about 140 percent, about 60 to about 140 percent, about 70 to about 140 percent, about 80 to about 140 percent, about 90 to about 140 percent, about 100 to about 140 percent, about 110 to about 140 percent, about 120 to about 140 percent, about 130 to about 140 percent, about 10 to about 80 percent, about 10 to about 70 percent, about 10 to about 60 percent, about 10 to about 50 percent, about 10 to about 40 percent, about 10 to about 30 percent, about 10 to about 20 percent, about 30 to about 70 percent, about 40 to about 70 percent, about 50 to about 70 percent, about 60 to about 70 percent, about 40 to about 60 percent, about 40 to about 50 percent, about 10 to about 20 percent, about 20 to about 30 percent, about 30 to about 40 percent, about 40 to about 50 percent, about 50 percent to about 60 percent, about 60 percent to about 70 percent, about 70 percent to about 80 percent, about 80 percent to about 90 percent, about 90 to about 100 percent, about 100 to about 110 percent, about 110 to about 120 percent, about 120 to about 130 percent, or about 130 percent to about 140 percent lower than the total kidney weight to body weight ratio of a subject not receiving the fixed-dose combination, or receiving only about 120 mg to about 240 mg bempedoic acid, or receiving only about 5 mg to about 90 mg tolvaptan.

In some embodiments, the subject receiving the fixed-dose combination has a BUN level about 2 to about 15 mg/dL, about 3 to about 15 mg/dL, about 4 to about 15 mg/dL, about 5 to about 15 mg/dL, about 6 to about 15 mg/dL, about 7 to about 15 mg/dL, about 8 to about 15 mg/dL, about 9 to about 15 mg/dL, about 10 to about 15 mg/dL, about 11 to about 15 mg/dL, about 12 to about 15 mg/dL, about 13 to about 15 mg/dL, about 14 to about 15 mg/dL, about 2 to about 14 mg/dL, about 2 to about 13 mg/dL, about 2 to about 12 mg/dL, about 2 to about 11 mg/dL, about 2 to about 10 mg/dL, about 2 to about 9 mg/dL, about 2 to about 8 mg/dL, about 2 to about 7 mg/dL, about 2 to about 6 mg/dL, about 2 to about 5 mg/dL, about 2 to about 4 mg/dL, about 2 to about 3 mg/dL, about 3 to about 9 mg/dL, about 4 to about 9 mg/dL, about 5 to about 9 mg/dL, about 6 to about 9 mg/dL, about 7 to about 9 mg/dL, about 8 to about 9 mg/dL, about 3 to about 8 mg/dL, about 3 to about 7 mg/dL, about 3 to about 6 mg/dL, about 3 to about 5 mg/dL, or about 3 to about 4 mg/dL lower than the BUN of a subject not receiving the fixed-dose combination, or receiving only about 30 mg to about 240 mg bempedoic acid, or receiving only about 5 mg to about 90 mg tolvaptan.

In some embodiments, the subject receiving the fixed-dose combination has a BUN level about 2 to about 15 mg/dL, about 3 to about 15 mg/dL, about 4 to about 15 mg/dL, about 5 to about 15 mg/dL, about 6 to about 15 mg/dL, about 7 to about 15 mg/dL, about 8 to about 15 mg/dL, about 9 to about 15 mg/dL, about 10 to about 15 mg/dL, about 11 to about 15 mg/dL, about 12 to about 15 mg/dL, about 13 to about 15 mg/dL, about 14 to about 15 mg/dL, about 2 to about 14 mg/dL, about 2 to about 13 mg/dL, about 2 to about 12 mg/dL, about 2 to about 11 mg/dL, about 2 to about 10 mg/dL, about 2 to about 9 mg/dL, about 2 to about 8 mg/dL, about 2 to about 7 mg/dL, about 2 to about 6 mg/dL, about 2 to about 5 mg/dL, about 2 to about 4 mg/dL, about 2 to about 3 mg/dL, about 3 to about 9 mg/dL, about 4 to about 9 mg/dL, about 5 to about 9 mg/dL, about 6 to about 9 mg/dL, about 7 to about 9 mg/dL, about 8 to about 9 mg/dL, about 3 to about 8 mg/dL, about 3 to about 7 mg/dL, about 3 to about 6 mg/dL, about 3 to about 5 mg/dL, or about 3 to about 4 mg/dL lower than the BUN of a subject not receiving the fixed-dose combination, or receiving only about 120 mg to about 240 mg bempedoic acid, or receiving only about 5 mg to about 90 mg tolvaptan.

In some embodiments, the subject receiving the fixed-dose combination has a decrease in eGFR of about 0.5 to about 5 mL/min/1.73 $m^2$/year, about 1 to about 5 mL/min/1.73 $m^2$/year, about 1.5 to about 5 mL/min/1.73 $m^2$/year, about 2 to about 5 mL/min/1.73 $m^2$/year, about 2.5 to about 5 mL/min/1.73 $m^2$/year, about 3 to about 5 mL/min/1.73 $m^2$/year, about 3.5 to about 5 mL/min/1.73 $m^2$/year, about 4 to about 5 mL/min/1.73 $m^2$/year, about 4.5 to about 5 mL/min/1.73 $m^2$/year, about 0.5 to about 4.5 mL/min/1.73 $m^2$/year, about 0.5 to about 4 mL/min/1.73 $m^2$/year, about 0.5 to about 3.5 mL/min/1.73 $m^2$/year, about 0.5 to about 3 mL/min/1.73 $m^2$/year, about 0.5 to about 2.5 mL/min/1.73 $m^2$/year, about 0.5 to about 2 mL/min/1.73 $m^2$/year, about 0.5 to about 1.5 mL/min/1.73 $m^2$/year, about 0.5 to about 1 mL/min/1.73 $m^2$/year, about 1.7 to about 3.4 mL/min/1.73 $m^2$/year, about 1.9 to about 3.4 mL/min/1.73 $m^2$/year, about 2.1 to about 3.4 mL/min/1.73 $m^2$/year, about 2.3 to about 3.4 mL/min/1.73 $m^2$/year, about 2.5 to about 3.4 mL/min/1.73 $m^2$/year, about 2.7 to about 3.4 mL/min/1.73 $m^2$/year, about 2.9 to about 3.4 mL/min/1.73 $m^2$/year, about 3.1 to about 3.4 mL/min/1.73 $m^2$/year, about 3.3 to about 3.4 mL/min/1.73 $m^2$/year, about 1.7 to about 1.9 mL/min/1.73 $m^2$/year, about 1.9 to about 2.1 mL/min/1.73 $m^2$/year, about 2.1 to about 2.3 mL/min/1.73 $m^2$/year, about 2.3 to about 2.5 mL/min/1.73 $m^2$/year, about 2.5 to about 2.7 mL/min/1.73 $m^2$/year, about 2.7 to about 2.9 mL/min/1.73 $m^2$/year, about 2.9 to about 3.1 mL/min/1.73 $m^2$/year, about 3.1 to about 3.3 mL/min/1.73 $m^2$/year, or about 3.3 to about 3.4 mL/min/1.73 $m^2$/year lower than the decrease in eGFR per year of a subject not receiving the fixed-dose combination, or receiving only about 30 mg to about 240 mg bempedoic acid, or receiving only about 5 mg to about 90 mg tolvaptan.

In some embodiments, the subject receiving the fixed-dose combination has a decrease in eGFR of about 0.5 to about 5 mL/min/1.73 $m^2$/year, about 1 to about 5 mL/min/1.73 $m^2$/year, about 1.5 to about 5 mL/min/1.73 $m^2$/year, about 2 to about 5 mL/min/1.73 $m^2$/year, about 2.5 to about 5 mL/min/1.73 $m^2$/year, about 3 to about 5 mL/min/1.73 $m^2$/year, about 3.5 to about 5 mL/min/1.73 $m^2$/year, about 4 to about 5 mL/min/1.73 $m^2$/year, about 4.5 to about 5 mL/min/1.73 $m^2$/year, about 0.5 to about 4.5 mL/min/1.73 $m^2$/year, about 0.5 to about 4 mL/min/1.73 $m^2$/year, about 0.5 to about 3.5 mL/min/1.73 $m^2$/year, about 0.5 to about 3 mL/min/1.73 $m^2$/year, about 0.5 to about 2.5 mL/min/1.73 $m^2$/year, about 0.5 to about 2 mL/min/1.73 $m^2$/year, about 0.5 to about 1.5 mL/min/1.73 $m^2$/year, about 0.5 to about 1 mL/min/1.73 $m^2$/year, about 1.7 to about 3.4 mL/min/1.73 $m^2$/year, about 1.9 to about 3.4 mL/min/1.73 $m^2$/year, about 2.1 to about 3.4 mL/min/1.73 $m^2$/year, about 2.3 to about 3.4 mL/min/1.73 $m^2$/year, about 2.5 to about 3.4 mL/min/1.73 $m^2$/year, about 2.7 to about 3.4 mL/min/1.73 $m^2$/year, about 2.9 to about 3.4 mL/min/1.73 $m^2$/year, about 3.1 to about 3.4 mL/min/1.73 $m^2$/year, about 3.3 to about 3.4 mL/min/1.73 $m^2$/year, about 1.7 to about 1.9 mL/min/1.73 $m^2$/year, about 1.9 to about 2.1 mL/min/1.73 $m^2$/year, about 2.1 to about 2.3 mL/min/1.73 $m^2$/year, about 2.3 to about 2.5 mL/min/1.73 $m^2$/year, about 2.5 to about 2.7 mL/min/1.73 $m^2$/year, about 2.7 to about 2.9 mL/min/1.73 $m^2$/year, about 2.9 to about 3.1 mL/min/1.73 $m^2$/year, about 3.1 to about 3.3 mL/min/1.73 $m^2$/year, or about 3.3 to about 3.4 mL/min/1.73 $m^2$/year lower than the decrease in eGFR per year of a subject not receiving the fixed-dose combination, or receiving only about 120 mg to about 240 mg bempedoic acid, or receiving only about 5 mg to about 90 mg tolvaptan.

In some embodiments, the subject receiving the fixed-dose combination has an increase in total kidney volume of about 0 to about 7 percent/year, about 0.5 to about 7 percent/year, about 1 to about 7 percent/year, about 1.5 to about 7 percent/year, about 2 to about 7 percent/year, about 2.5 to about 7 percent/year, about 3 to about 7 percent/year, about 3.5 to about 7 percent/year, about 4 to about 7 percent/year, about 4.5 to about 7 percent/year, about 5 to about 7 percent/year, about 5.5 to about 7 percent/year, about 6 to about 7 percent/year, about 6.5 to about 7 percent/year, about 0 to about 6.5 percent/year, about 0 to about 6 percent/year, about 0 to about 5.5 percent/year, about 0 to about 5 percent/year, about 0 to about 4.5 percent/year, about 0 to about 4 percent/year, about 0 to about 3.5 percent/year, about 0 to about 3 percent/year, about 0 to about 2.5 percent/year, about 0 to about 2 percent/year, about 0 to about 1.5 percent/year, about 0 to about 1 percent/year, about 0 to about 0.5 percent/year, about 1 to about 5 percent/year, about 1.5 to about 5 percent/year, about 2 to about 5 percent/year, about 2.5 to about 5 percent/year, about 3 to about 5 percent/year, about 3.5 to about 5 percent/year, about 4 to about 5 percent/year, about 4.5 to about 5 percent/year, about 1 to about 1.5 percent/year, about 1.5 to about 2 percent/year, about 2 to about 2.5 percent/year, about 2.5 to about 3 percent/year, about 3 to about 3.5 percent/year, about 3.5 to about 4 percent/year, about 4 to about 4.5 percent/year, or about 4.5 to about 5 percent/year lower than the percent/year increase in total kidney volume of a subject not receiving the fixed-dose combination, or receiving only about 30 mg to about 240 mg bempedoic acid, or receiving only about 5 mg to about 90 mg tolvaptan.

In some embodiments, the subject receiving the fixed-dose combination has an increase in total kidney volume of about 0 to about 7 percent/year, about 0.5 to about 7 percent/year, about 1 to about 7 percent/year, about 1.5 to about 7 percent/year, about 2 to about 7 percent/year, about 2.5 to about 7 percent/year, about 3 to about 7 percent/year, about 3.5 to about 7 percent/year, about 4 to about 7 percent/year, about 4.5 to about 7 percent/year, about 5 to about 7 percent/year, about 5.5 to about 7 percent/year, about 6 to about 7 percent/year, about 6.5 to about 7 percent/year, about 0 to about 6.5 percent/year, about 0 to about 6 percent/year, about 0 to about 5.5 percent/year, about 0 to about 5 percent/year, about 0 to about 4.5 percent/year, about 0 to about 4 percent/year, about 0 to about 3.5 percent/year, about 0 to about 3 percent/year, about 0 to about 2.5 percent/year, about 0 to about 2 percent/year, about 0 to about 1.5 percent/year, about 0 to about 1 percent/year, about 0 to about 0.5 percent/year, about 1 to about 5 percent/year, about 1.5 to about 5 percent/year, about 2 to about 5 percent/year, about 2.5 to about 5 percent/year, about 3 to about 5 percent/year, about 3.5 to about 5 percent/year, about 4 to about 5 percent/year, about 4.5 to about 5 percent/year, about 1 to about 1.5 percent/year, about 1.5 to about 2 percent/year, about 2 to about 2.5 percent/year, about 2.5 to about 3 percent/year, about 3 to about 3.5 percent/year, about 3.5 to about 4 percent/year, about 4 to about 4.5 percent/year, or about 4.5 to about 5 percent/year lower than the percent/year increase in total kidney volume of a subject not receiving the fixed-dose combination, or receiving only about 120 mg to about 240 mg bempedoic acid, or receiving only about 5 mg to about 90 mg tolvaptan.

In some embodiments, the subject receiving the fixed-dose combination has a composite incidence of clinical endpoints selected from worsening kidney function, kidney pain, hypertension, and albuminuria of about 5 to about 50 percent, about 10 to about 50 percent, about 15 to about 50 percent, about 20 to about 50 percent, about 25 to about 50 percent, about 30 to about 50 percent, about 35 to about 50 percent, about 40 to about 50 percent, about 45 to about 50 percent, about 5 to about 45 percent, about 5 to about 40 percent, about 5 to about 35 percent, about 5 to about 30 percent, about 5 to about 25 percent, about 5 to about 20 percent, about 5 to about 15 percent, about 5 to about 10 percent, about 15 to about 40 percent, about 20 to about 40 percent, about 25 to about 40 percent, about 30 to about 40 percent, about 35 to about 40 percent, about 15 to about 20 percent, about 20 to about 25 percent, about 25 to about 30 percent, about 30 to about 35 percent, or about 35 to about 40 percent lower than the composite incidence of clinical endpoints of a subject not receiving the fixed-dose combination, or receiving only about 30 mg to about 240 mg bempedoic acid, or receiving only about 5 mg to about 90 mg tolvaptan.

In some embodiments, the subject receiving the fixed-dose combination has a composite incidence of clinical endpoints selected from worsening kidney function, kidney pain, hypertension, and albuminuria of about 5 to about 50 percent, about 10 to about 50 percent, about 15 to about 50 percent, about 20 to about 50 percent, about 25 to about 50 percent, about 30 to about 50 percent, about 35 to about 50 percent, about 40 to about 50 percent, about 45 to about 50 percent, about 5 to about 45 percent, about 5 to about 40 percent, about 5 to about 35 percent, about 5 to about 30 percent, about 5 to about 25 percent, about 5 to about 20 percent, about 5 to about 15 percent, about 5 to about 10 percent, about 15 to about 40 percent, about 20 to about 40 percent, about 25 to about 40 percent, about 30 to about 40 percent, about 35 to about 40 percent, about 15 to about 20 percent, about 20 to about 25 percent, about 25 to about 30 percent, about 30 to about 35 percent, or about 35 to about 40 percent lower than the composite incidence of clinical endpoints of a subject not receiving the fixed-dose combination, or receiving only about 120 mg to about 240 mg bempedoic acid, or receiving only about 5 mg to about 90 mg tolvaptan.

In some embodiments, the subject receiving the fixed-dose combination has higher liver AMPK activity than a subject not receiving the fixed-dose combination, or receiving only about 5 mg to about 90 mg tolvaptan. In some embodiments, the subject receiving the fixed-dose combination has a higher degree of liver ACC phosphorylation than a subject not receiving the fixed-dose combination, or receiving only about 5 mg to about 90 mg tolvaptan. In some embodiments, the subject receiving the fixed-dose combination has a higher degree of peroxisome proliferator-activated receptor gamma coactivator 1-α (PGC1α) activity than a subject receiving only about 5 mg to about 90 mg tolvaptan.

In some embodiments, the fixed-dose combination is delivered orally. Examples of oral dosage forms include, but are not limited to a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical composition is formulated as a tablet.

In some embodiments, the fixed-dose combination comprises about 180 mg bempedoic acid. In some embodiments, the fixed-dose combination comprises about 5 mg, about 10 mg, about 15 mg, about 30 mg, about 45 mg, about 60 mg, or about 90 mg tolvaptan.

Also provided herein are methods of treating ADPKD in a subject in need thereof, the methods comprising administering to the subject an effective amount of bempedoic acid and tolvaptan. Also provided herein are methods of slowing the progression of ADPKD in a subject in need thereof, the methods comprising administering to the subject an effective amount of bempedoic acid and tolvaptan. Also provided herein are methods of preventing kidney failure, reducing total kidney volume, and/or slowing the progression of kidney dysfunction in a subject with ADPKD in need thereof, the methods comprising administering to the subject an effective amount of bempedoic acid and tolvaptan.

In some embodiments, the effective amount of bempedoic acid and tolvaptan comprises about 30 mg to about 240 mg bempedoic acid. In some embodiments, the effective amount of bempedoic acid and tolvaptan comprises about 120 mg to about 240 mg bempedoic acid. In certain embodiments, the effective amount of bempedoic acid and tolvaptan comprises about 180 mg bempedoic acid. In some embodiments, the effective amount of bempedoic acid and tolvaptan comprises about 5 mg, about 10 mg, about 15 mg, about 30 mg, about 45 mg, about 60 mg, or about 90 mg tolvaptan.

In some embodiments, the subject receiving the effective amount of bempedoic acid and tolvaptan has a lower total kidney weight to body weight ratio than a subject receiving a placebo, or receiving only bempedoic acid, or receiving only tolvaptan. In some embodiments, the subject receiving the effective amount of bempedoic acid and tolvaptan has a lower blood urea nitrogen level than a subject receiving a placebo, or receiving only bempedoic acid, or receiving only tolvaptan.

In some embodiments, the subject receiving the effective amount of bempedoic acid and tolvaptan has a total kidney weight to body weight ratio about 10 to about 140 percent, about 20 to about 140 percent, about 30 to about 140 percent, about 40 to about 140 percent, about 50 to about 140 percent, about 60 to about 140 percent, about 70 to about 140 percent, about 80 to about 140 percent, about 90 to about 140 percent, about 100 to about 140 percent, about 110 to about 140 percent, about 120 to about 140 percent, about 130 to about 140 percent, about 10 to about 80 percent, about 10 to about 70 percent, about 10 to about 60 percent, about 10 to about 50 percent, about 10 to about 40 percent, about 10 to about 30 percent, about 10 to about 20 percent, about 30 to about 70 percent, about 40 to about 70 percent, about 50 to about 70 percent, about 60 to about 70 percent, about 40 to about 60 percent, about 40 to about 50 percent, about 10 to about 20 percent, about 20 to about 30 percent, about 30 to about 40 percent, about 40 to about 50 percent, about 50 percent to about 60 percent, about 60 percent to about 70 percent, about 70 percent to about 80 percent, about 80 percent to about 90 percent, about 90 to about 100 percent, about 100 to about 110 percent, about 110 to about 120 percent, about 120 to about 130 percent, or about 130 percent to about 140 percent lower than the total kidney weight to body weight ratio of a subject receiving a placebo, or receiving only bempedoic acid, or receiving only tolvaptan.

In some embodiments, the subject receiving the effective amount of bempedoic acid and tolvaptan has a BUN level about 2 to about 15 mg/dL, about 3 to about 15 mg/dL, about 4 to about 15 mg/dL, about 5 to about 15 mg/dL, about 6 to about 15 mg/dL, about 7 to about 15 mg/dL, about 8 to about 15 mg/dL, about 9 to about 15 mg/dL, about 10 to about 15 mg/dL, about 11 to about 15 mg/dL, about 12 to about 15 mg/dL, about 13 to about 15 mg/dL, about 14 to about 15 mg/dL, about 2 to about 14 mg/dL, about 2 to about 13 mg/dL, about 2 to about 12 mg/dL, about 2 to about 11 mg/dL, about 2 to about 10 mg/dL, about 2 to about 9 mg/dL, about 2 to about 8 mg/dL, about 2 to about 7 mg/dL, about 2 to about 6 mg/dL, about 2 to about 5 mg/dL, about 2 to about 4 mg/dL, about 2 to about 3 mg/dL, about 3 to about 9 mg/dL, about 4 to about 9 mg/dL, about 5 to about 9 mg/dL, about 6 to about 9 mg/dL, about 7 to about 9 mg/dL, about 8 to about 9 mg/dL, about 3 to about 8 mg/dL, about 3 to about 7 mg/dL, about 3 to about 6 mg/dL, about 3 to about 5 mg/dL, or about 3 to about 4 mg/dL lower than the BUN of a subject receiving a placebo, or receiving only bempedoic acid, or receiving only tolvaptan.

In some embodiments, the subject receiving the effective amount of bempedoic acid and tolvaptan has a decrease in eGFR of about 0.5 to about 5 mL/min/1.73 $m^2$/year, about 1 to about 5 mL/min/1.73 $m^2$/year, about 1.5 to about 5 mL/min/1.73 $m^2$/year, about 2 to about 5 mL/min/1.73 $m^2$/year, about 2.5 to about 5 mL/min/1.73 $m^2$/year, about 3 to about 5 mL/min/1.73 $m^2$/year, about 3.5 to about 5 mL/min/1.73 $m^2$/year, about 4 to about 5 mL/min/1.73 $m^2$/year, about 4.5 to about 5 mL/min/1.73 $m^2$/year, about 0.5 to about 4.5 mL/min/1.73 $m^2$/year, about 0.5 to about 4 mL/min/1.73 $m^2$/year, about 0.5 to about 3.5 mL/min/1.73 $m^2$/year, about 0.5 to about 3 mL/min/1.73 $m^2$/year, about 0.5 to about 2.5 mL/min/1.73 $m^2$/year, about 0.5 to about 2 mL/min/1.73 $m^2$/year, about 0.5 to about 1.5 mL/min/1.73 $m^2$/year, about 0.5 to about 1 mL/min/1.73 $m^2$/year, about 1.7 to about 3.4 mL/min/1.73 $m^2$/year, about 1.9 to about 3.4 mL/min/1.73 $m^2$/year, about 2.1 to about 3.4 mL/min/1.73 $m^2$/year, about 2.3 to about 3.4 mL/min/1.73 $m^2$/year, about 2.5 to about 3.4 mL/min/1.73 $m^2$/year, about 2.7 to about 3.4 mL/min/1.73 $m^2$/year, about 2.9 to about 3.4 mL/min/1.73 $m^2$/year, about 3.1 to about 3.4 mL/min/1.73 $m^2$/year, about 3.3 to about 3.4 mL/min/1.73 $m^2$/year, about 1.7 to about 1.9 mL/min/1.73 $m^2$/year, about 1.9 to about 2.1 mL/min/1.73 $m^2$/year, about 2.1 to about 2.3 mL/min/1.73 $m^2$/year, about 2.3 to about 2.5 mL/min/1.73 $m^2$/year, about 2.5 to about 2.7 mL/min/1.73 $m^2$/year, about 2.7 to about 2.9 mL/min/1.73 $m^2$/year, about 2.9 to about 3.1 mL/min/1.73 $m^2$/year, about 3.1 to about 3.3 mL/min/1.73 $m^2$/year, or about 3.3 to about 3.4 mL/min/1.73 $m^2$/year lower than the decrease in eGFR per year of a subject receiving a placebo, or receiving only bempedoic acid, or receiving only tolvaptan.

In some embodiments, the subject receiving the effective amount of bempedoic acid and tolvaptan has an increase in total kidney volume of about 0 to about 7 percent/year, about 0.5 to about 7 percent/year, about 1 to about 7 percent/year, about 1.5 to about 7 percent/year, about 2 to about 7 percent/year, about 2.5 to about 7 percent/year, about 3 to about 7 percent/year, about 3.5 to about 7 percent/year, about 4 to about 7 percent/year, about 4.5 to about 7 percent/year, about 5 to about 7 percent/year, about 5.5 to about 7 percent/year, about 6 to about 7 percent/year, about 6.5 to about 7 percent/year, about 0 to about 6.5 percent/year, about 0 to about 6 percent/year, about 0 to about 5.5 percent/year, about 0 to about 5 percent/year, about 0 to about 4.5 percent/year, about 0 to about 4 percent/year, about 0 to about 3.5 percent/year, about 0 to about 3 percent/year, about 0 to about 2.5 percent/year, about 0 to about 2 percent/year, about 0 to about 1.5 percent/year, about 0 to about 1 percent/year, about 0 to about 0.5 percent/year, about 1 to about 5 percent/year, about 1.5 to about 5 percent/year, about 2 to about 5 percent/year, about 2.5 to about 5 percent/year, about 3 to about 5 percent/year, about 3.5 to about 5 percent/year, about 4 to about 5 percent/year, about 4.5 to about 5 percent/year, about 1 to about 1.5 percent/year, about 1.5 to about 2 percent/year, about 2 to about 2.5 percent/year, about 2.5 to about 3 percent/year, about 3 to about 3.5 percent/year, about 3.5 to about 4 percent/year, about 4 to about 4.5 percent/year, or about 4.5 to about 5 percent/year lower than the percent/year increase in total kidney volume of a subject receiving a placebo, or receiving only bempedoic acid, or receiving only tolvaptan.

In some embodiments, the subject receiving the effective amount of bempedoic acid and tolvaptan has a composite incidence of clinical endpoints selected from worsening kidney function, kidney pain, hypertension, and albuminuria of about 5 to about 50 percent, about 10 to about 50 percent, about 15 to about 50 percent, about 20 to about 50 percent, about 25 to about 50 percent, about 30 to about 50 percent, about 35 to about 50 percent, about 40 to about 50 percent, about 45 to about 50 percent, about 5 to about 45 percent, about 5 to about 40 percent, about 5 to about 35 percent, about 5 to about 30 percent, about 5 to about 25 percent, about 5 to about 20 percent, about 5 to about 15 percent, about 5 to about 10 percent, about 15 to about 40 percent, about 20 to about 40 percent, about 25 to about 40 percent, about 30 to about 40 percent, about 35 to about 40 percent, about 15 to about 20 percent, about 20 to about 25 percent, about 25 to about 30 percent, about 30 to about 35 percent, or about 35 to about 40 percent lower than the composite incidence of clinical endpoints of a subject receiving a placebo, or receiving only bempedoic acid, or receiving only tolvaptan.

In some embodiments, the subject receiving the effective amount of bempedoic acid and tolvaptan has higher liver AMPK activity than a subject receiving a placebo, or receiving only tolvaptan. In some embodiments, the subject receiving the effective amount of bempedoic acid and tolvaptan has a higher degree of liver ACC phosphorylation than a subject receiving a placebo, or receiving only tolvaptan. In some embodiments, the subject receiving the effective amount of bempedoic acid and tolvaptan has a higher degree of peroxisome proliferator-activated receptor gamma coactivator 1-α (PGC1α) activity than a subject receiving only tolvaptan.

In some embodiments, the effective amount of bempedoic acid and the effective amount of tolvaptan are delivered orally. Examples of oral dosage forms include, but are not limited to a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical composition is formulated as a tablet.

Also provided herein are methods of treating ADPKD in a subject in need thereof, the methods comprising administering to the subject an effective amount of bempedoic acid. Also provided herein are methods of slowing the progression of ADPKD in a subject in need thereof, the methods comprising administering to the subject an effective amount of bempedoic acid. Also provided herein are methods of preventing kidney failure, reducing total kidney volume, and/or slowing the progression of kidney dysfunction in a subject with ADPKD in need thereof, the methods comprising administering to the subject an effective amount of bempedoic acid.

In some embodiments, the effective amount of bempedoic acid is about 30 mg to about 240 mg. In some embodiments, the effective amount of bempedoic acid is about 120 mg to about 240 mg. In certain embodiments, the effective amount of bempedoic acid is about 180 mg.

In some embodiments, the subject receiving the effective amount of bempedoic acid has a lower total kidney weight to body weight ratio than a subject receiving a placebo, or has an equivalent or a lower total kidney weight to body weight ratio than a subject receiving tolvaptan therapy. In some embodiments, the subject receiving the effective amount of bempedoic acid has a lower blood urea nitrogen level than a subject receiving a placebo, or has an equivalent or a lower blood urea nitrogen level than a subject receiving tolvaptan therapy.

In some embodiments, the subject receiving the effective amount of bempedoic acid has a total kidney weight to body weight ratio about 10 to about 140 percent, about 20 to about 140 percent, about 30 to about 140 percent, about 40 to about 140 percent, about 50 to about 140 percent, about 60 to about 140 percent, about 70 to about 140 percent, about 80 to about 140 percent, about 90 to about 140 percent, about 100 to about 140 percent, about 110 to about 140 percent, about 120 to about 140 percent, about 130 to about 140 percent, about 10 to about 80 percent, about 10 to about 70 percent, about 10 to about 60 percent, about 10 to about 50 percent, about 10 to about 40 percent, about 10 to about 30 percent, about 10 to about 20 percent, about 30 to about 70 percent, about 40 to about 70 percent, about 50 to about 70 percent, about 60 to about 70 percent, about 40 to about 60 percent, about 40 to about 50 percent, about 10 to about 20 percent, about 20 to about 30 percent, about 30 to about 40 percent, about 40 to about 50 percent, about 50 percent to about 60 percent, about 60 percent to about 70 percent, about 70 percent to about 80 percent, about 80 percent to about 90 percent, about 90 to about 100 percent, about 100 to about 110 percent, about 110 to about 120 percent, about 120 to about 130 percent, or about 130 percent to about 140 percent lower than the total kidney weight to body weight ratio of a subject receiving a placebo, or has an equivalent or a lower total kidney weight to body weight ratio than the total kidney weight to body weight ratio of a subject receiving tolvaptan therapy.

In some embodiments, the subject receiving the effective amount of bempedoic acid has a BUN level about 2 to about 15 mg/dL, about 3 to about 15 mg/dL, about 4 to about 15 mg/dL, about 5 to about 15 mg/dL, about 6 to about 15 mg/dL, about 7 to about 15 mg/dL, about 8 to about 15 mg/dL, about 9 to about 15 mg/dL, about 10 to about 15 mg/dL, about 11 to about 15 mg/dL, about 12 to about 15 mg/dL, about 13 to about 15 mg/dL, about 14 to about 15 mg/dL, about 2 to about 14 mg/dL, about 2 to about 13 mg/dL, about 2 to about 12 mg/dL, about 2 to about 11 mg/dL, about 2 to about 10 mg/dL, about 2 to about 9 mg/dL, about 2 to about 8 mg/dL, about 2 to about 7 mg/dL, about 2 to about 6 mg/dL, about 2 to about 5 mg/dL, about 2 to about 4 mg/dL, about 2 to about 3 mg/dL, about 3 to about 9 mg/dL, about 4 to about 9 mg/dL, about 5 to about 9 mg/dL, about 6 to about 9 mg/dL, about 7 to about 9 mg/dL, about 8 to about 9 mg/dL, about 3 to about 8 mg/dL, about 3 to about 7 mg/dL, about 3 to about 6 mg/dL, about 3 to about 5 mg/dL, or about 3 to about 4 mg/dL lower than the BUN of a subject receiving a placebo, or has an equivalent or a lower BUN than the BUN of a subject receiving tolvaptan therapy.

In some embodiments, the subject receiving the effective amount of bempedoic acid has a decrease in eGFR of about 0.5 to about 5 mL/min/1.73 $m^2$/year, about 1 to about 5 mL/min/1.73 $m^2$/year, about 1.5 to about 5 mL/min/1.73 $m^2$/year, about 2 to about 5 mL/min/1.73 $m^2$/year, about 2.5 to about 5 mL/min/1.73 $m^2$/year, about 3 to about 5 mL/min/1.73 $m^2$/year, about 3.5 to about 5 mL/min/1.73 $m^2$/year, about 4 to about 5 mL/min/1.73 $m^2$/year, about 4.5 to about 5 mL/min/1.73 $m^2$/year, about 0.5 to about 4.5 mL/min/1.73 $m^2$/year, about 0.5 to about 4 mL/min/1.73 $m^2$/year, about 0.5 to about 3.5 mL/min/1.73 $m^2$/year, about 0.5 to about 3 mL/min/1.73 $m^2$/year, about 0.5 to about 2.5 mL/min/1.73 $m^2$/year, about 0.5 to about 2 mL/min/1.73 $m^2$/year, about 0.5 to about 1.5 mL/min/1.73 $m^2$/year, about 0.5 to about 1 mL/min/1.73 $m^2$/year, about 1.7 to about 3.4 mL/min/1.73 $m^2$/year, about 1.9 to about 3.4 mL/min/1.73 $m^2$/year, about 2.1 to about 3.4 mL/min/1.73 $m^2$/year, about 2.3 to about 3.4 mL/min/1.73 $m^2$/year, about 2.5 to about 3.4 mL/min/1.73 $m^2$/year, about 2.7 to about 3.4 mL/min/1.73 $m^2$/year, about 2.9 to about 3.4 mL/min/1.73 $m^2$/year, about 3.1 to about 3.4 mL/min/1.73 $m^2$/year, about 3.3 to about 3.4 mL/min/1.73 $m^2$/year, about 1.7 to about 1.9 mL/min/1.73 $m^2$/year, about 1.9 to about 2.1 mL/min/1.73 $m^2$/year, about 2.1 to about 2.3 mL/min/1.73 $m^2$/year, about 2.3 to about 2.5 mL/min/1.73 $m^2$/year, about 2.5 to about 2.7 mL/min/1.73 $m^2$/year, about 2.7 to about 2.9 mL/min/1.73 $m^2$/year, about 2.9 to about 3.1 mL/min/1.73 $m^2$/year, about 3.1 to about 3.3 mL/min/1.73 $m^2$/year, or about 3.3 to about 3.4 mL/min/1.73 $m^2$/year lower than the decrease in eGFR per year of a subject receiving a placebo, or has an equivalent or a lower decrease in eGFR per year than the decrease in eGFR per year of a subject receiving tolvaptan therapy.

In some embodiments, the subject receiving the effective amount of bempedoic acid has an increase in total kidney volume of about 0 to about 7 percent/year, about 0.5 to about 7 percent/year, about 1 to about 7 percent/year, about 1.5 to about 7 percent/year, about 2 to about 7 percent/year, about 2.5 to about 7 percent/year, about 3 to about 7 percent/year, about 3.5 to about 7 percent/year, about 4 to about 7 percent/year, about 4.5 to about 7 percent/year, about 5 to about 7 percent/year, about 5.5 to about 7 percent/year, about 6 to about 7 percent/year, about 6.5 to about 7 percent/year, about 0 to about 6.5 percent/year, about 0 to about 6 percent/year, about 0 to about 5.5 percent/year, about 0 to about 5 percent/year, about 0 to about 4.5 percent/year, about 0 to about 4 percent/year, about 0 to about 3.5 percent/year, about 0 to about 3 percent/year, about 0 to about 2.5 percent/year, about 0 to about 2 percent/year, about 0 to about 1.5 percent/year, about 0 to about 1 percent/year, about 0 to about 0.5 percent/year, about 1 to about 5 percent/year, about 1.5 to about 5 percent/year, about 2 to about 5 percent/year, about 2.5 to about 5 percent/year, about 3 to about 5 percent/year, about 3.5 to about 5 percent/year, about 4 to about 5 percent/year, about 4.5 to about 5 percent/year, about 1 to about 1.5 percent/year, about 1.5 to about 2 percent/year, about 2 to about 2.5 percent/year, about 2.5 to about 3 percent/year, about 3 to about 3.5 percent/year, about 3.5 to about 4 percent/year, about 4 to about 4.5 percent/year, or about 4.5 to about 5 percent/year lower than the percent/year increase in total kidney volume of a subject receiving a placebo, or has an equivalent or a lower percent/year increase in total kidney volume than the percent/year increase in total kidney volume of a subject receiving only tolvaptan.

In some embodiments, the subject receiving the effective amount of bempedoic acid has a composite incidence of clinical endpoints selected from worsening kidney function, kidney pain, hypertension, and albuminuria of about 5 to about 50 percent, about 10 to about 50 percent, about 15 to about 50 percent, about 20 to about 50 percent, about 25 to about 50 percent, about 30 to about 50 percent, about 35 to about 50 percent, about 40 to about 50 percent, about 45 to about 50 percent, about 5 to about 45 percent, about 5 to about 40 percent, about 5 to about 35 percent, about 5 to about 30 percent, about 5 to about 25 percent, about 5 to about 20 percent, about 5 to about 15 percent, about 5 to about 10 percent, about 15 to about 40 percent, about 20 to about 40 percent, about 25 to about 40 percent, about 30 to about 40 percent, about 35 to about 40 percent, about 15 to about 20 percent, about 20 to about 25 percent, about 25 to about 30 percent, about 30 to about 35 percent, or about 35 to about 40 percent lower than the composite incidence of clinical endpoints of a subject receiving a placebo, or has an equivalent or a lower incidence of clinical endpoints selected from worsening kidney function, kidney pain, hypertension, and albuminuria than a subject receiving tolvaptan therapy.

In some embodiments, the effective amount of bempedoic acid is delivered orally. Examples of oral dosage forms include, but are not limited to a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical composition is formulated as a tablet.

Also provided herein are methods of treating dyslipidemia in a subject in need thereof, the methods generally comprising administering to the subject an effective amount of tolvaptan and an effective amount of bempedoic acid. In some embodiments, the method lowers LDL-C in the blood or serum of a subject. In some embodiments, the method lowers systolic and/or diastolic blood pressure in a subject. In some embodiments, the method lowers hsCRP in the blood or serum of a subject. In some embodiments, the method lowers the body weight of the subject. In some embodiments, the method reduces the risk of atherosclerotic cardiovascular disease in a subject.

In some embodiments, tolvaptan is delivered orally. In some embodiments, the bempedoic acid and tolvaptan are formulated as an oral dosage form. Examples of oral dosage forms include, but are not limited to a drench, a tablet, a capsule, a softgel capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical composition is formulated as a tablet.

In some embodiments, the methods disclosed herein lower the level of apo B in blood or serum of the subject below that of a subject not receiving the tolvaptan and bempedoic acid combination. In some embodiments, the methods disclosed herein lower the level of non-high-density lipoprotein cholesterol in blood or serum of the subject below that of a subject not receiving the tolvaptan and bempedoic acid combination. In some embodiments, the methods disclosed herein lower the level of triglycerides in blood or serum of the subject below that of a subject not receiving the tolvaptan and bempedoic acid combination. In some embodiments, the methods disclosed herein lower the LDL particle number in blood or serum of the subject below that of a subject not receiving the tolvaptan and bempedoic acid combination. In some embodiments, the methods disclosed herein decrease the size of VLDL particles in blood or serum of the subject below that of a subject not receiving the tolvaptan and bempedoic acid combination. In some embodiments, the methods disclosed herein decrease the number of VLDL particles in blood or serum of the subject below that of a subject not receiving tolvaptan and bempedoic acid combination. In some embodiments, the methods disclosed herein increase the level of apo A1 in blood or serum of the subject above that of a subject not receiving the tolvaptan and bempedoic acid combination. In some embodiments, the methods disclosed herein do not change the level of apo A1 in blood or serum of the subject compared to that of a subject not receiving the tolvaptan and bempedoic acid combination. In some embodiments, the methods disclosed herein decrease the level of apo A1 in blood or serum of the subject below that of a subject not receiving the tolvaptan and bempedoic acid combination.

In certain embodiments, the methods disclosed herein comprise administering to a subject the combined therapeutic agents (e.g., bempedoic acid and tolvaptan) as a single dosage form. In certain embodiments, the methods disclosed herein comprise administering to a subject the therapeutic agents (e.g., bempedoic acid and a tolvaptan) as separate dosage forms.

In some embodiments, the subject is a human.

EXAMPLES

Below are examples of specific embodiments for carrying out the present disclosure. The examples are offered for illustrative purposes only, and are not intended to limit the scope of the present disclosure in any way.

Any terms not directly defined herein shall be understood to have the meanings commonly associated with them as understood within the art of the disclosure. Certain terms are discussed herein to provide additional guidance to the practitioner in describing the compositions, devices, methods and the like of aspects of the disclosure, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the disclosure herein.

Example 1—Immunoblot Assays of FATP2 and ACLY Protein Expression in Various Mouse Tissues and Kidney Cell Lines The example describes immunoblot assays to assess the FATP2 and ACLY protein expression in mouse liver, lung, kidney, spleen, and muscle tissues, as well as proximal tubule- and inner medullary collecting duct-derived mouse epithelial cells.

FATP2 (ACSVL1; SLC27A2) protein expression was observed in immunoblots of homogenates of different mouse tissues and kidney cell lines. Immunoblotting of various mouse tissues (FIG. 1A, left) revealed expression of two distinct FATP2 isoforms. The short splice variant (FATP2b at ~55 kDa), which lacks the protein domain required for conversion of bempedoic acid to its active metabolite bempedoic acid-CoA, was expressed in all tissues tested. However, the long form (FATP2a at ~70 kDa) had significant expression only in liver and kidney tissue, thus providing specificity of ETC-1002 pro-drug conversion to its active form only in these tissues. The FATP2a and FATP2b isoforms were expressed in immortalized mouse kidney epithelial cells that were derived from both proximal tubule and inner medullary collecting duct, both with or without knockout of the Pkd1 gene (FIG. 1A, right).

Figure 1B:
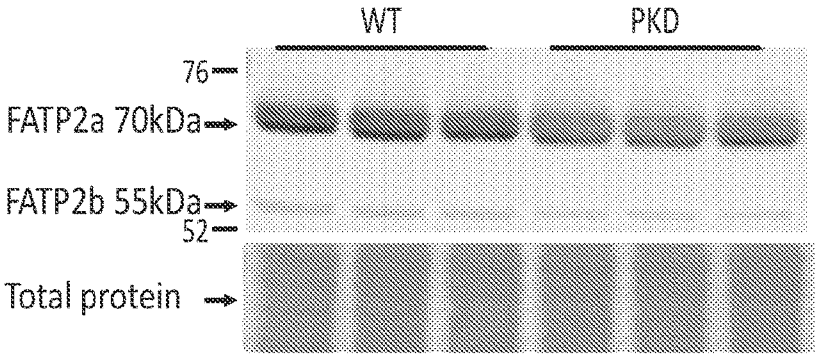
FIG. 1B is an immunoblot assay showing the FATP2a 70 kDa and FATP2b 55 kDa isoform expression in homogenates of wild type and ADPKD mutant (Pkd1RC/RC) mouse kidney tissue.

Similar protein expression levels of both isoforms of FATP2 were also found in both wild-type (WT) and ADPKD mutant (Pkd1RC/RC) mouse kidney tissue (FIG. 1B)).

ACLY protein correlated with disease severity in the hypomorphic $Pkd^{RC/RC}$ ADPKD mouse model. ACLY protein expression and activity was increased in Pkd1−/− kidney epithelial cells as compared to controls in vitro.

Figure 1C:
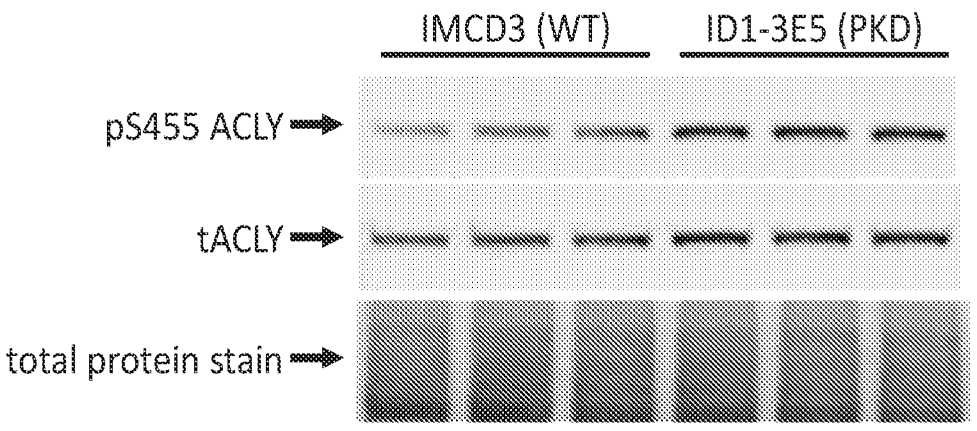
FIG. 1C is an immunoblot assay showing the ATP citrate lyase (ACLY) protein expression and activity in inner medullary collecting duct-derived Pkd1−/− mouse kidney epithelial cells compared to wild type.
Figure 1D:
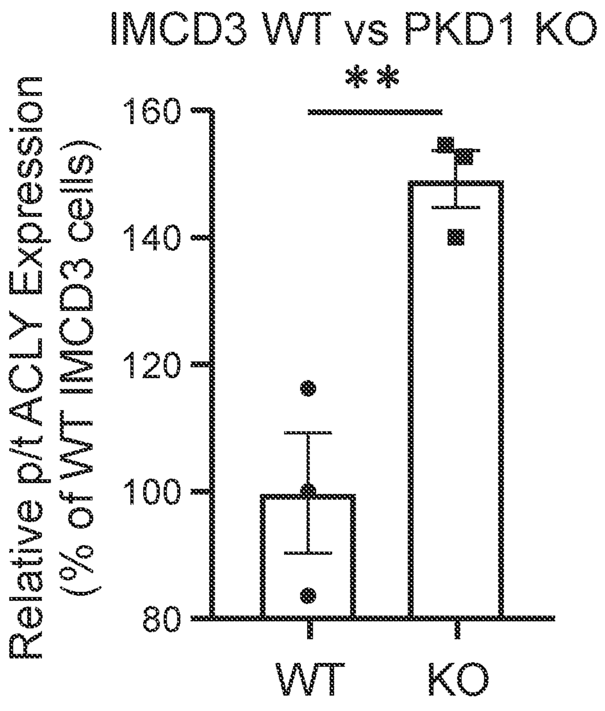
FIG. 1D is a histogram comparing the ratios of phosphorylated ACLY to total ACLY expression in IMCD-derived wild-type and PKD1 knockout cells.

Immunoblotting of inner medullary collecting duct (IMCD)-derived mouse epithelial cells for expression of t ACLY (total ACLY) and pS455 ACLY (FIG. 1C) showed increased expression of activated (pS455) ACLY relative to t ACLY in Pkd1-null (ID1-3E5) cells as compared with wild-type (WT) (IMCD3) cells (densitometric quantitation revealed a significant ~50% increase in the pS455-ACLY/t-ACLY ratio in the ID1-3E5 cells ($p<0.05$; unpaired t-test) (FIG. 1D)). A total protein stain shows comparable loading across the different lanes. Cells were pretreated with or without (+ or −, as indicated) a novel small molecule ACLY inhibitor prior to lysis and immunoblotting.

Figure 1E:
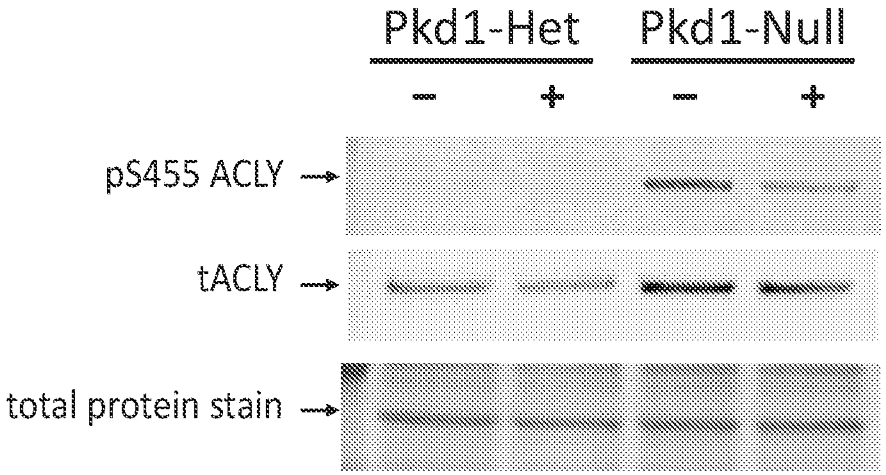
FIG. 1E is an immunoblot assay showing the ACLY protein expression and activity in proximal tubule (PT)-derived Pkd1-heterozygous and Pkd1-null mouse kidney epithelial cells compared to wild type.
Figure 1F:
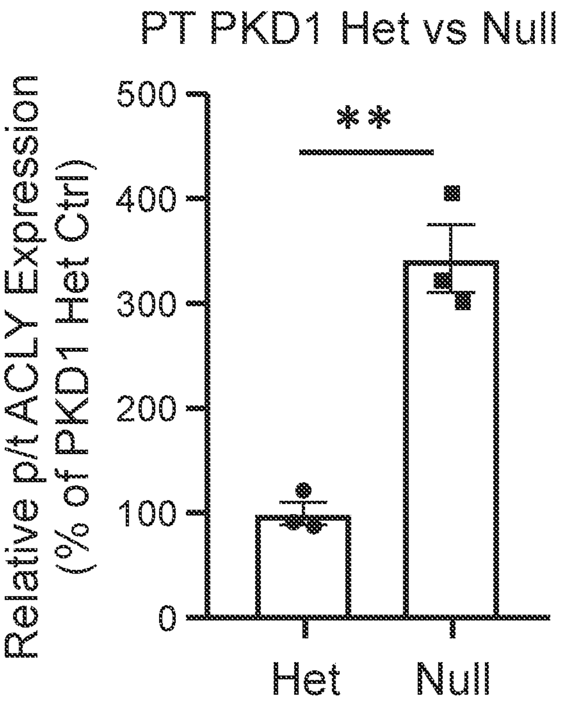
FIG. 1F is a histogram comparing the ratios of phosphorylated ACLY to total ACLY expression in PT-derived Pkd1-heterozygous and Pkd1-null cells.

Immunoblotting of proximal tubule (PT)-derived mouse epithelial cells shows greater protein expression of total ACLY (t ACLY) and activated ACLY (FIG. 1E), as detected using a phospho-specific antibody directed against Ser455, a known AKT phosphorylation and activating site (pS455 ACLY), in cells with Pkd1 expression knocked out at both alleles as compared with cells that are heterozygous for Pkd1 deletion (densitometric quantitation revealed a significant ~250% increase in the pS455-ACLY/t-ACLY ratio in the ID1-3E5 cells ($p<0.05$; unpaired t-test) (FIG. 1F).

Example 2—Growth Inhibition Studies of ACLY Inhibitors Bempedoic Acid (ETC-1002) and SB-204990 in Pkd1−/− Kidney Epithelial Cells in 3D Cultures The example describes cell growth inhibition studies in 3D cultures of kidney epithelial cells using either of ACLY inhibitors bempedoic acid or SB-204990. SB-204990 is represented by the structure of Formula (III):

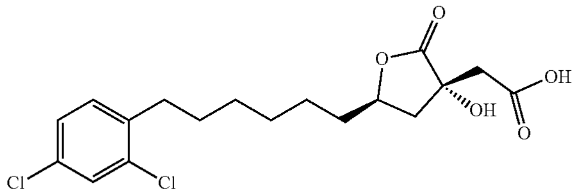 [SMILES: O=C(O)C[C@@]1(O)C[C@@H](CCCCCCc2ccc(Cl)cc2Cl)OC1=O]

Figure 2A:
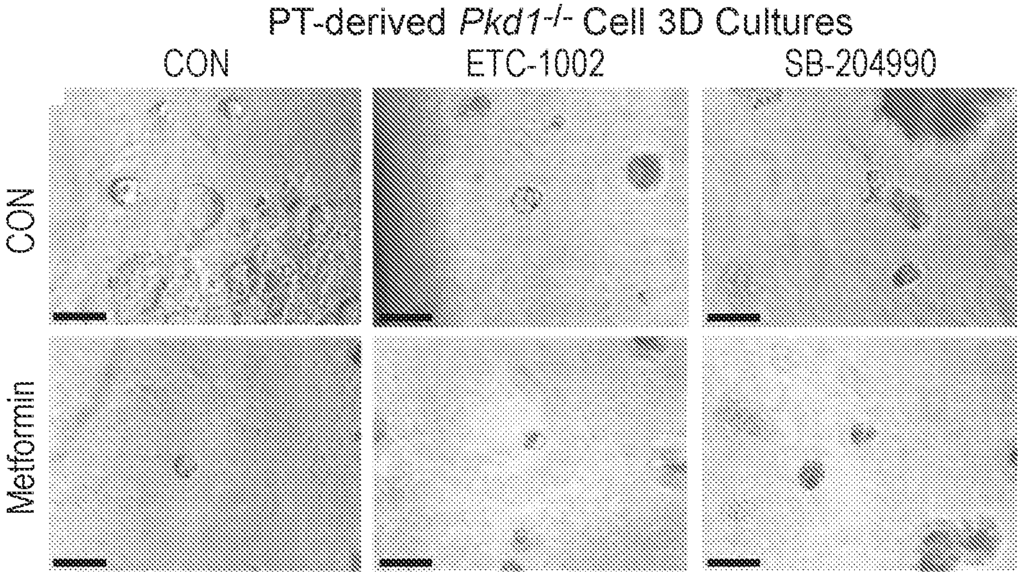
FIG. 2A shows photographs comparing cyst growth in PT-derived Pkd1−/− cell 3D cultures that are untreated, treated with ETC-1002, or treated with SB-204990, with and without metformin.
Figure 2B:
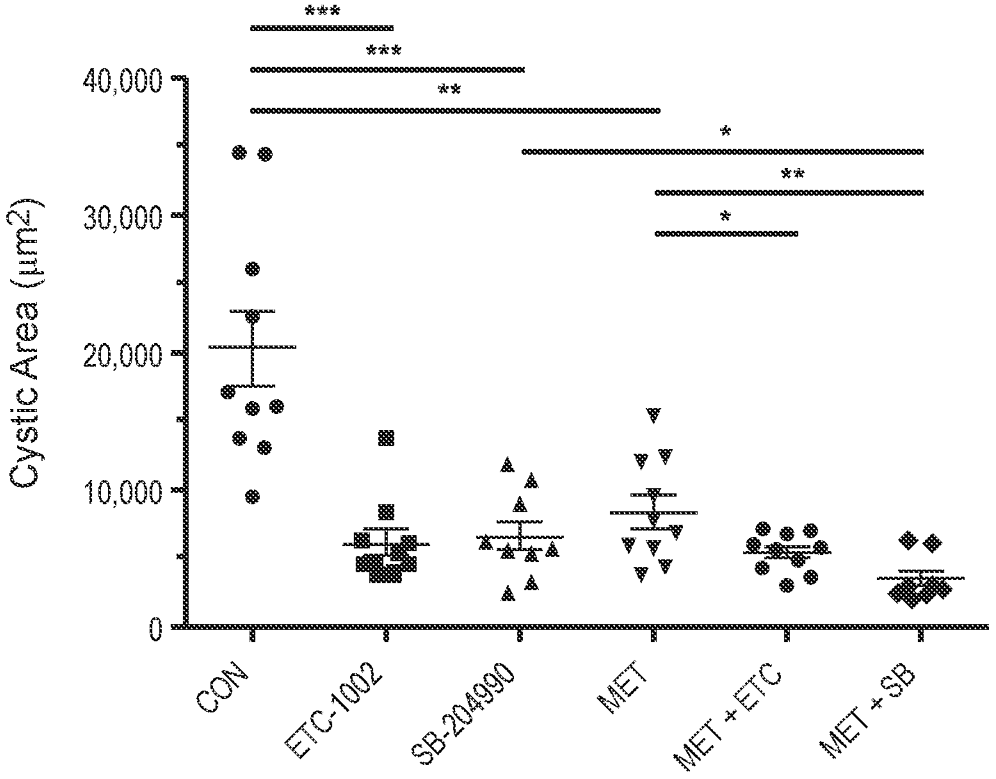
FIG. 2B is a plot comparing the cystic area of PT-derived Pkd1−/− cell 3D cultures that are untreated, treated with ETC-1002, or treated with SB-204990, with and without metformin.

ACLY inhibitors inhibited cyst growth of proximal tubule (PT)-derived Pkd1−/− kidney epithelial cells in 3D cultures both alone. Cells were grown in Matrigel 12 days and treated with 10 μM forskolin+100 μM IBMX for 11 days, and then treated with either vehicle (DMSO; CON), 500 μM metformin, 100 μM ETC-1002 (bempedoic acid) or 30 μM SB-204990 either alone or in combination as shown for the last 3 days (FIG. 2A). Summary data revealed that each of the treatments significantly reduced cyst area relative to control. Error bars indicate 95% confidence interval (CI) (*$P<0.05$, $P<0.01$, *$P<0.001$ for the indicated comparisons by one-way ANOVA and Tukey's multiple comparison test) (FIG. 2B).

Figure 2C:
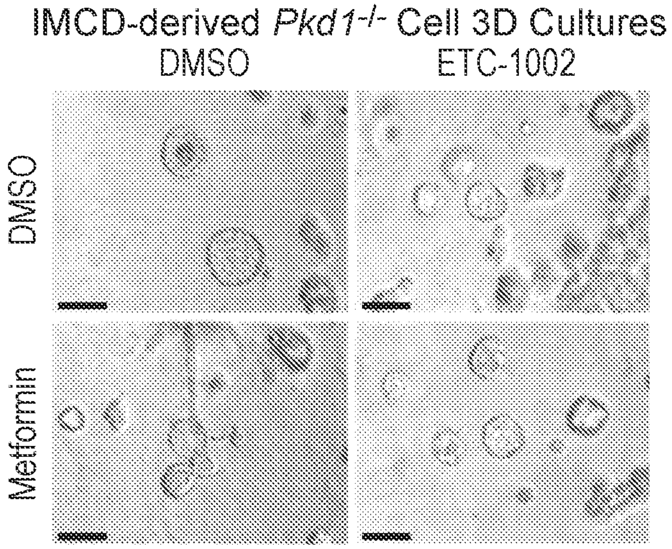
FIG. 2C shows photographs comparing cyst growth in IMCD-derived Pkd1−/− cell 3D cultures that are untreated or treated with ETC-1002, with and without metformin.
Figure 2D:
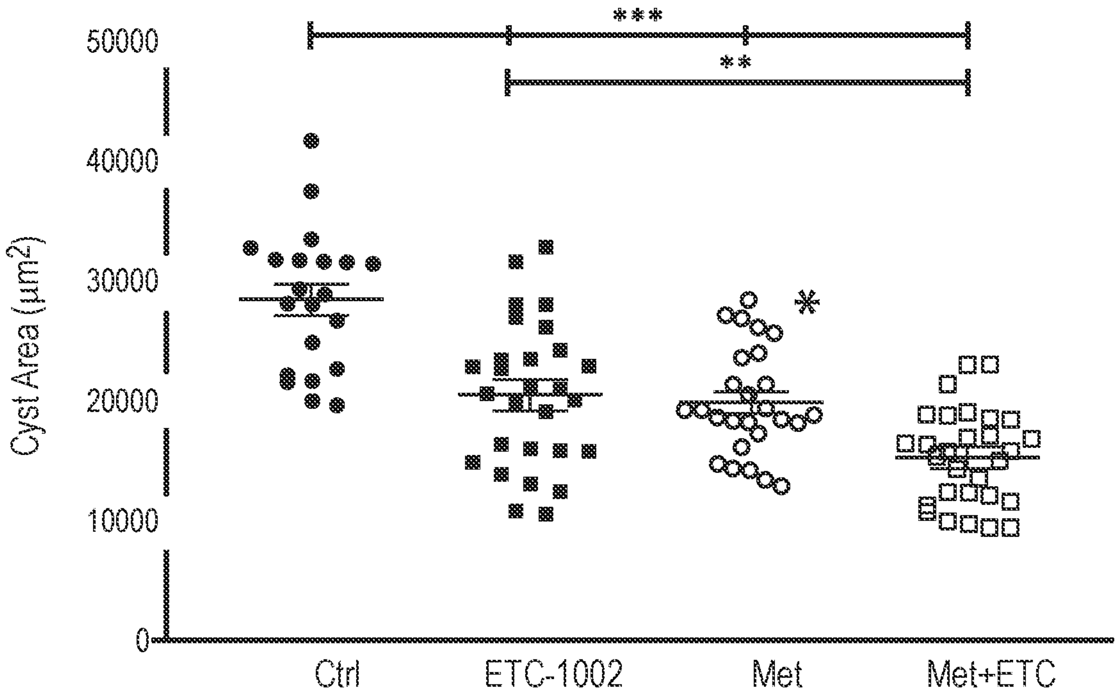
FIG. 2D is a plot comparing the cyst area of IMCD-derived Pkd1−/− cell 3D cultures that are untreated or treated with ETC-1002, with and without metformin.

ETC-1002 inhibited cyst growth of inner medullary collecting duct (IMCD)-derived Pkd1−/− kidney epithelial cells in 3D cultures. Cells were grown in Matrigel for 6 days and treated with 10 μM forskolin+100 μM IBMX±500 μM metformin and/or 100 μM of ETC-1002 (bempedoic acid) for the last 3 days alone or in combination as shown (FIG. 2C). Summary data revealed that each of the treatments alone significantly reduced cyst area relative to control. Error bars indicate 95% CI (*$P<0.05$, $P<0.01$, *$P<0.001$ for the indicated comparisons by one-way ANOVA and Tukey's multiple comparison test) (FIG. 2D).

Example 3—Studies Examining the Effects of Bempedoic Acid and Tolvaptan Alone and in Combination in a Rapidly Developing Early Onset ADPKD Mouse Model The example describes characterization of the early onset, rapidly developing ADPKD mouse model Pkd1fl/fl;Pax8-rtTA;Tet-O-Cre homozygous in the C57BL/6 background.

Figure 3A:
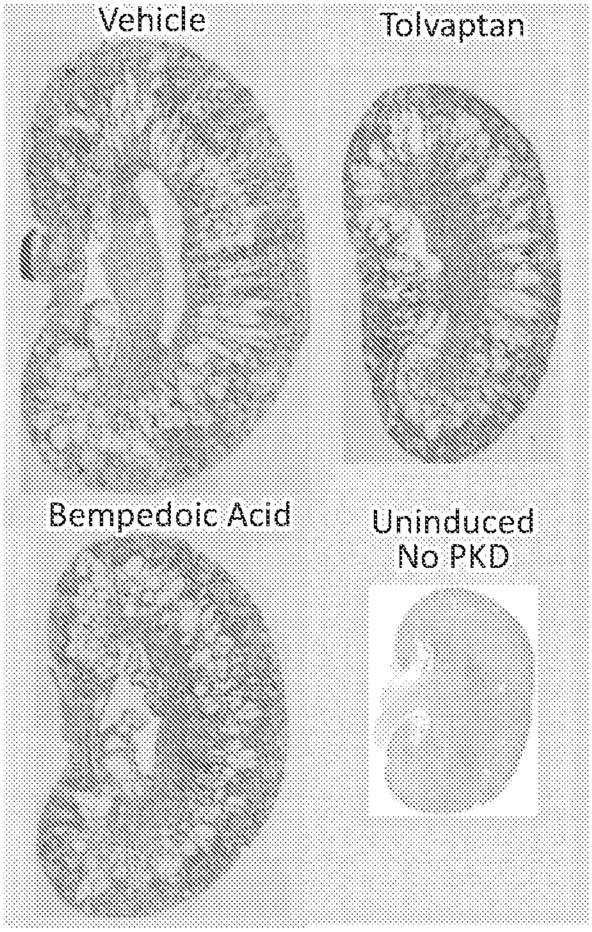
FIG. 3A shows images of H&E stains of kidney sections from Cre+ mice at postnatal day 22 treated with vehicle, bempedoic acid, or tolvaptan; as well as an image of a kidney section from an uninduced control mouse without PKD.

Doxycycline was administered intraperitoneally (50 mg/kg/day) on postnatal days 10 and 11 (P10 and P11) to induce Pkd1 deletion and rapidly progressive PKD in the Cre+ mice. Mice were treated with the various drugs and combinations or vehicle by oral gavage daily from P12-P21 and were then sacrificed at P22 of age to harvest kidneys for histology, weight measurements and blood urea nitrogen (BUN) measurements. Treatments were vehicle, tolvaptan 30 mg/kg/d, tolvaptan 100 mg/kg/d, bempedoic acid 30 mg/kg/d, tolvaptan 30 mg/kg/d+bempedoic acid 30 mg/kg/d, and tolvaptan 100 mg/kg/d+bempedoic acid 30 mg/kg/d;

also included was an uninduced, untreated group without PKD. Each treatment group consisted of 3-6 mice. Representative H&E (hematoxylin and eosin) stains of kidney sections from Cre+ mice at P22 demonstrate a rapid increase in kidney size over time (vehicle vs uninduced). Administration of tolvaptan or ETC-1002 (bempedoic acid) each showed a marked reduction in kidney size when compared to vehicle control (FIG. 3A).

Figure 3B:
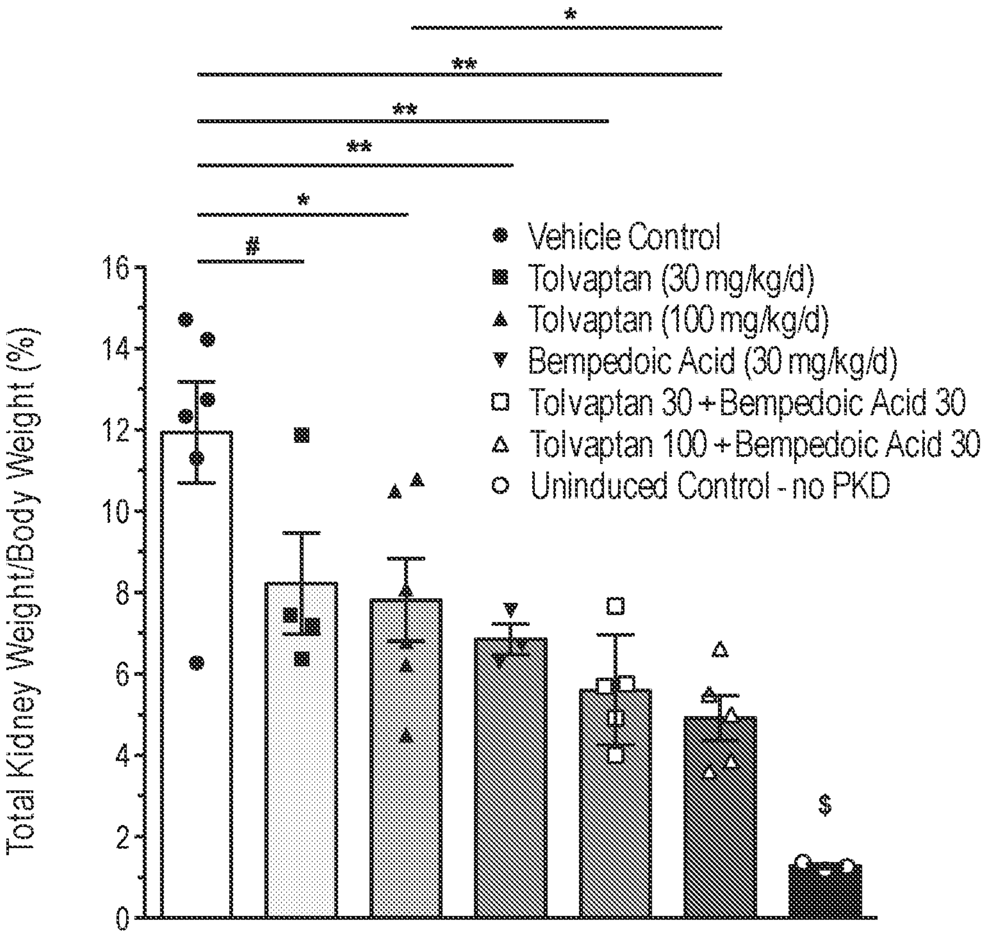
FIG. 3B is a histogram comparing the total kidney weight to body weight percent in an early onset, rapidly developing ADPKD mouse model, with groups treated with vehicle, tolvaptan 30 mg/kg/d, tolvaptan 100 mg/kg/d, bempedoic acid 30 mg/kg/d, tolvaptan 30 mg/kg/d+bempedoic acid 30 mg/kg/d, and tolvaptan 100 mg/kg/d+bempedoic acid 30 mg/kg/d; and in an uninduced, untreated control group without PKD.

The total kidney weight to body weight ratios were dramatically increased at the time of euthanasia in the Cre+ mice relative to Cre− control mice. Administration of tolvaptan (30 mg/kg/d) or (100 mg/kg/d) each reduced total kidney weight to body weight ratio. Bempedoic acid (30/mg/kg/d) also significantly reduced total kidney weight to body weight ratio to a similar level when administered alone. Total kidney weight to body weight was further reduced when combined with tolvaptan (30 or 100 mg/kg/d), such that the combination was lower than either treatment alone (FIG. 3B). Bempedoic acid (30 mg/kg/d) reduced total kidney weight to body weight ratio relative to vehicle (6.9±0.4% vs. 11.9±1.2%; P<0.01, n=3-6, unpaired t-test). Similarly, tolvaptan (100 mg/kg/d) reduced total kidney weight to body weight ratio relative to vehicle (7.8±1.0%; P<0.05, n=6). Addition of bempedoic acid to tolvaptan caused a further reduction in total kidney weight to body weight ratio relative to tolvaptan alone (4.9±0.6%; P<0.05).

Figure 3C:
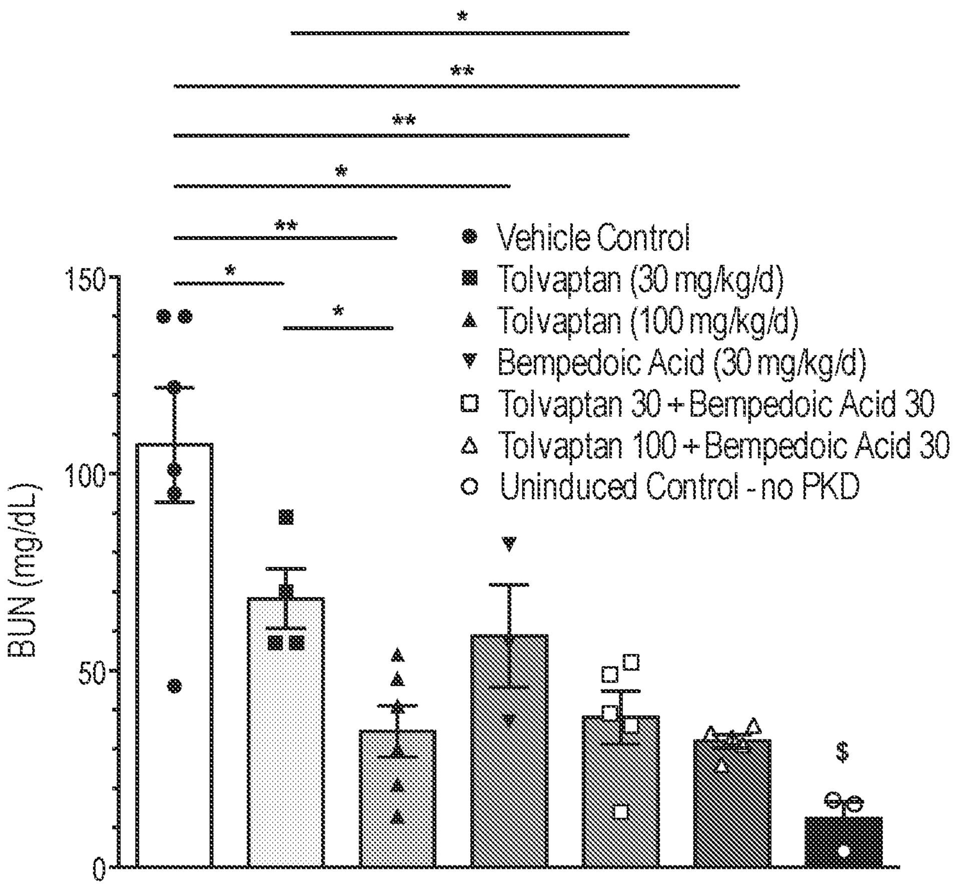
FIG. 3C is a histogram comparing the blood urea nitrogen (BUN) in an early onset, rapidly developing ADPKD mouse model, with groups treated with vehicle, tolvaptan 30 mg/kg/d, tolvaptan 100 mg/kg/d, bempedoic acid 30 mg/kg/d, tolvaptan 30 mg/kg/d+bempedoic acid 30 mg/kg/d, or tolvaptan 100 mg/kg/d+bempedoic acid 30 mg/kg/d; and in an uninduced, untreated control without PKD.

BUN was also dramatically increased at the time of euthanasia in the Cre+ mice relative to Cre−control mice. Administration of tolvaptan (30 mg/kg/d) or (100 mg/kg/d) each reduced BUN in a dose-dependent manner. Bempedoic acid (30 mg/kg/d) also significantly reduced BUN to a similar level as tolvaptan when administered alone, which was further reduced when combined with tolvaptan (30 or 100 mg/kg/d), such that the combination lowered BUN more than either treatment alone (FIG. 3C). Bempedoic acid (30 mg/kg/d) reduced BUN relative to vehicle (59±13 vs. 107±14 mg/dL; P<0.05). Tolvaptan treatment also dose-dependently decreased BUN relative to vehicle at 30 mg/kg/d (68±8; P<0.05) and 100 mg/kg/d (35±7; P<0.01). Addition of bempedoic to tolvaptan at 30 mg/kg/d caused a further significant reduction in BUN (38±7; P<0.05).

Figure 4A:
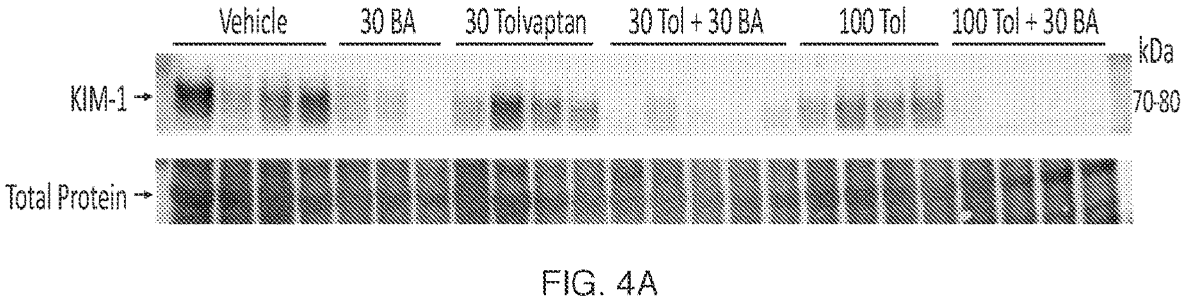
FIG. 4A is an immunoblot assay of kidney lysates from the treatment groups described in FIGS. 3B and 3C comparing the kidney injury molecule-1 (KIM-1) expression relative to total protein expression among the treatment groups.
Figure 4B:
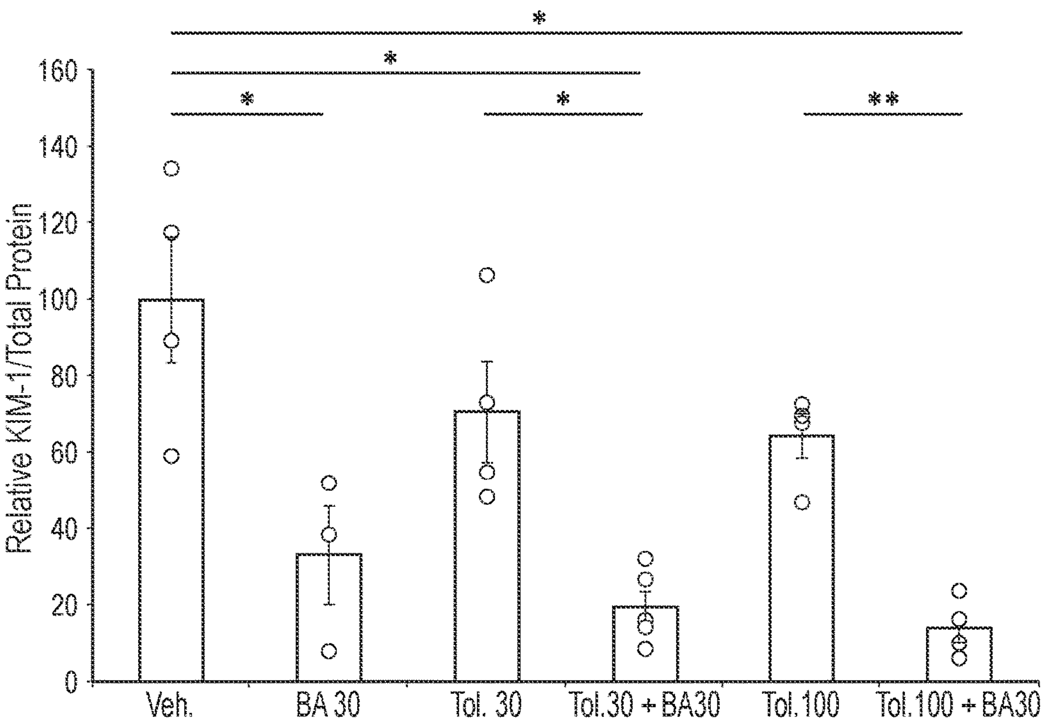
FIG. 4B is a histogram comparing the kidney lysate kidney injury molecule-1 (KIM-1) expression relative to total protein expression among the treatment groups described in FIGS. 3B and 3C.
Figure 5A:
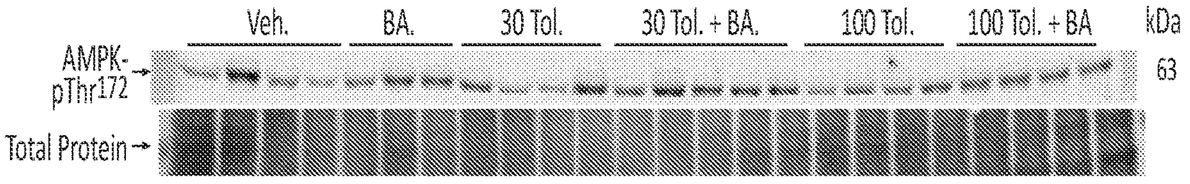
FIG. 5A is an immunoblot assay of kidney lysates from the treatment groups described in FIGS. 3B and 3C comparing the AMPK-pThr$^{172}$ expression relative to total protein expression among the treatment groups.
Figure 5B:
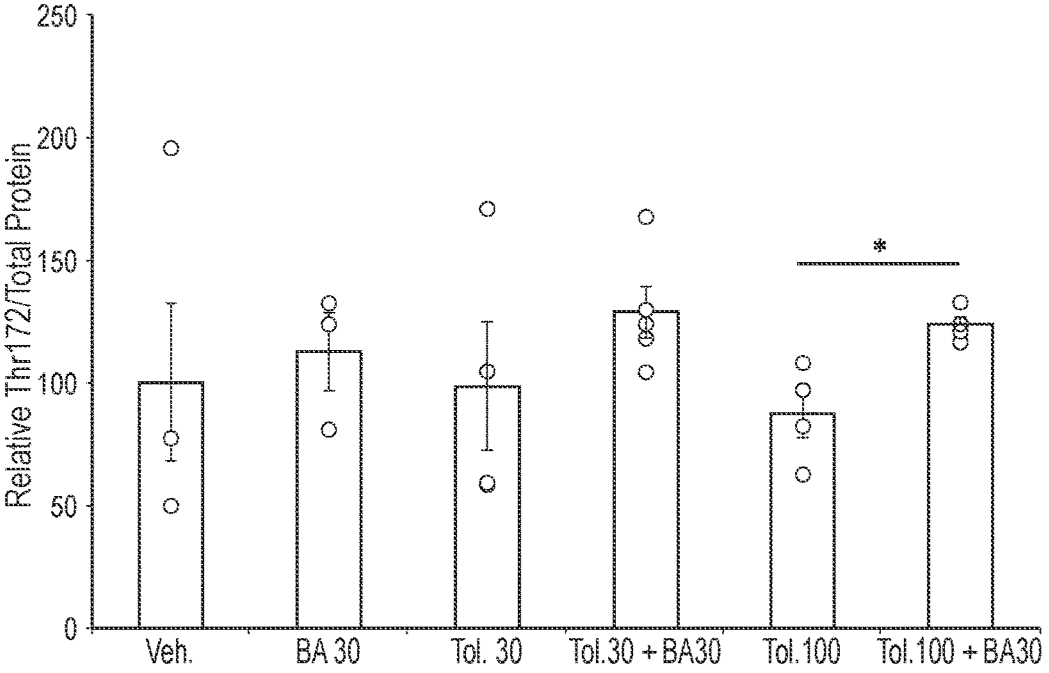
FIG. 5B is a histogram comparing the kidney lysate Thr$^{172}$ expression relative to total protein expression among the treatment groups described in FIGS. 3B and 3C.
Figure 6A:
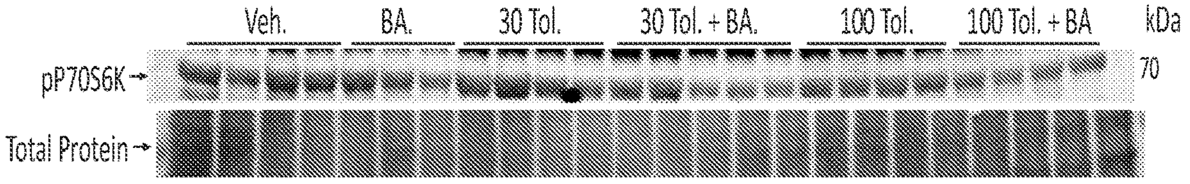
FIG. 6A is an immunoblot assay of kidney lysates from the treatment groups described in FIGS. 3B and 3C comparing the pP70S6K expression relative to total protein expression among the treatment groups.
Figure 6B:
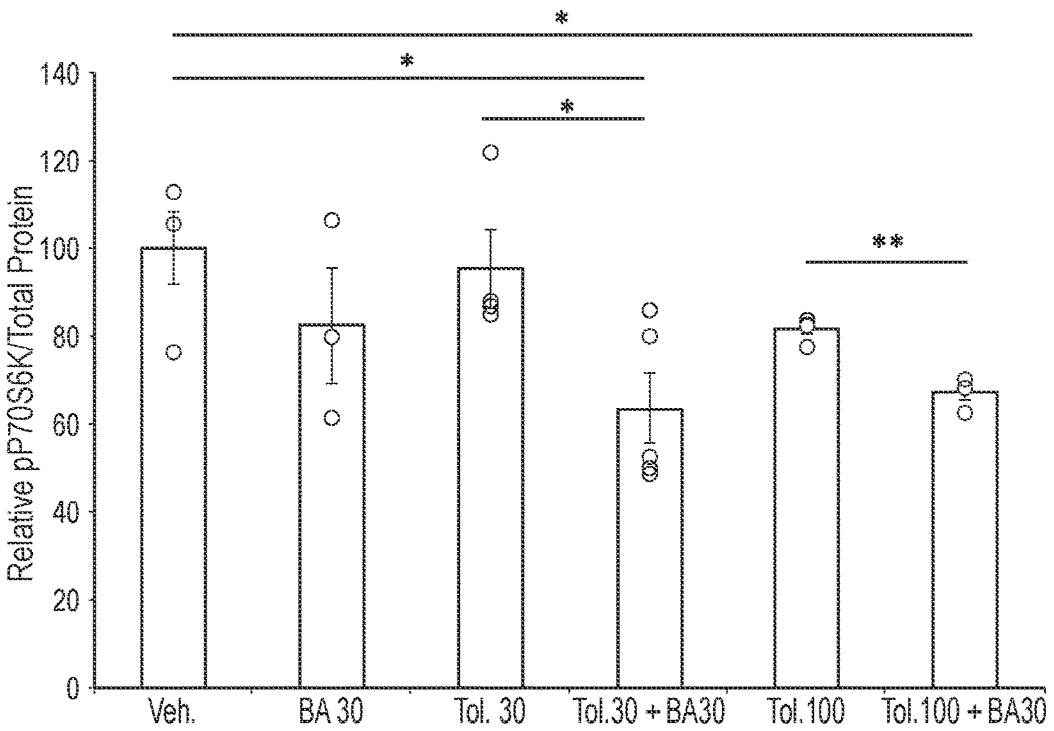
FIG. 6B is a histogram comparing the kidney lysate pP70S6K expression relative to total protein expression among the treatment groups described in FIGS. 3B and 3C.
Figure 7A:
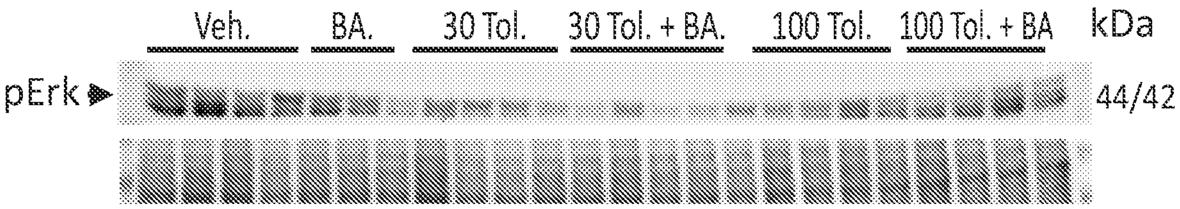
FIG. 7A is an immunoblot assay of kidney lysates from the treatment groups described in FIGS. 3B and 3C comparing the pERK expression relative to total protein expression among the treatment groups.
Figure 7B:
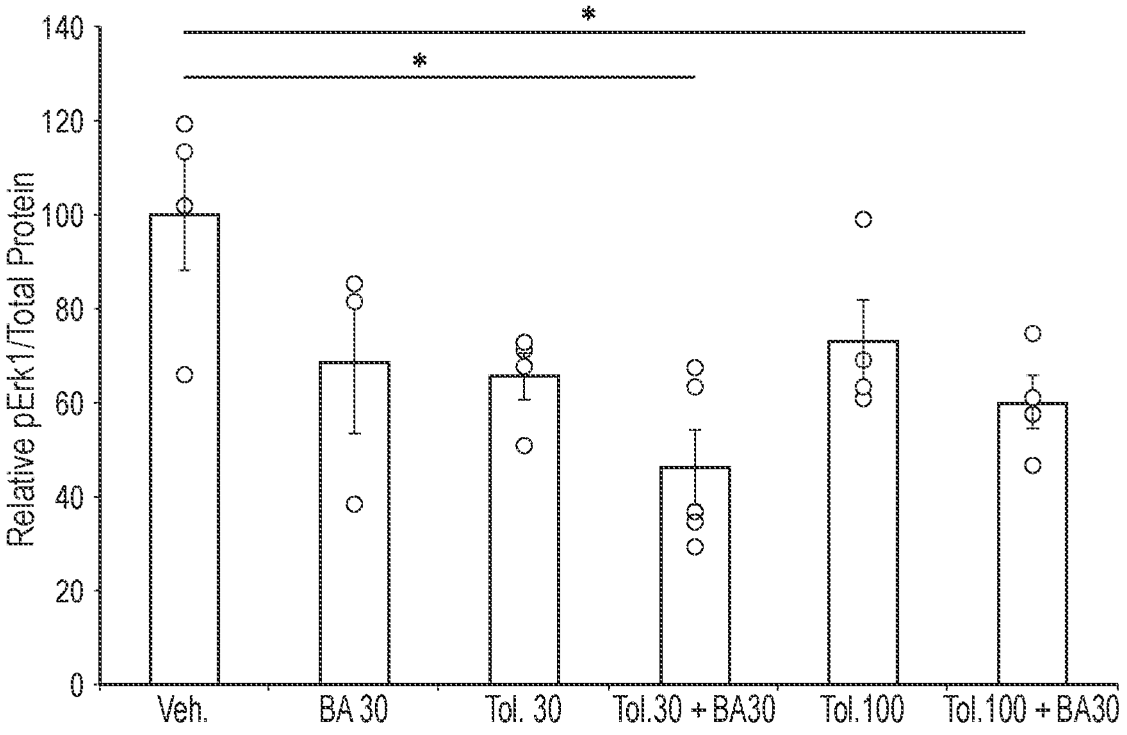
FIG. 7B is a histogram comparing the kidney lysate pERK expression relative to total protein expression among the treatment groups described in FIGS. 3B and 3C.
Figure 8A:
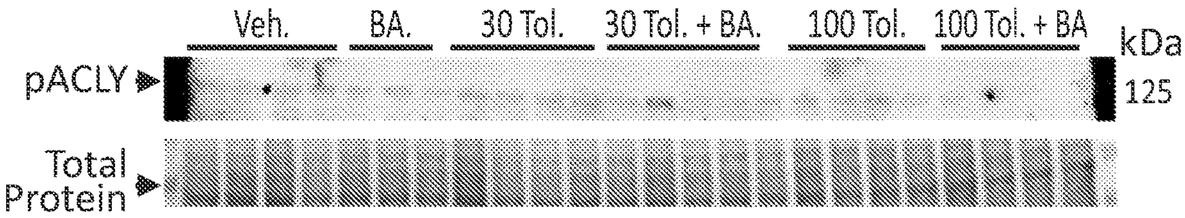
FIG. 8A is an immunoblot assay of kidney lysates from the treatment groups described in FIGS. 3B and 3C comparing the pACLY expression relative to total protein expression among the treatment groups.
Figure 8B:
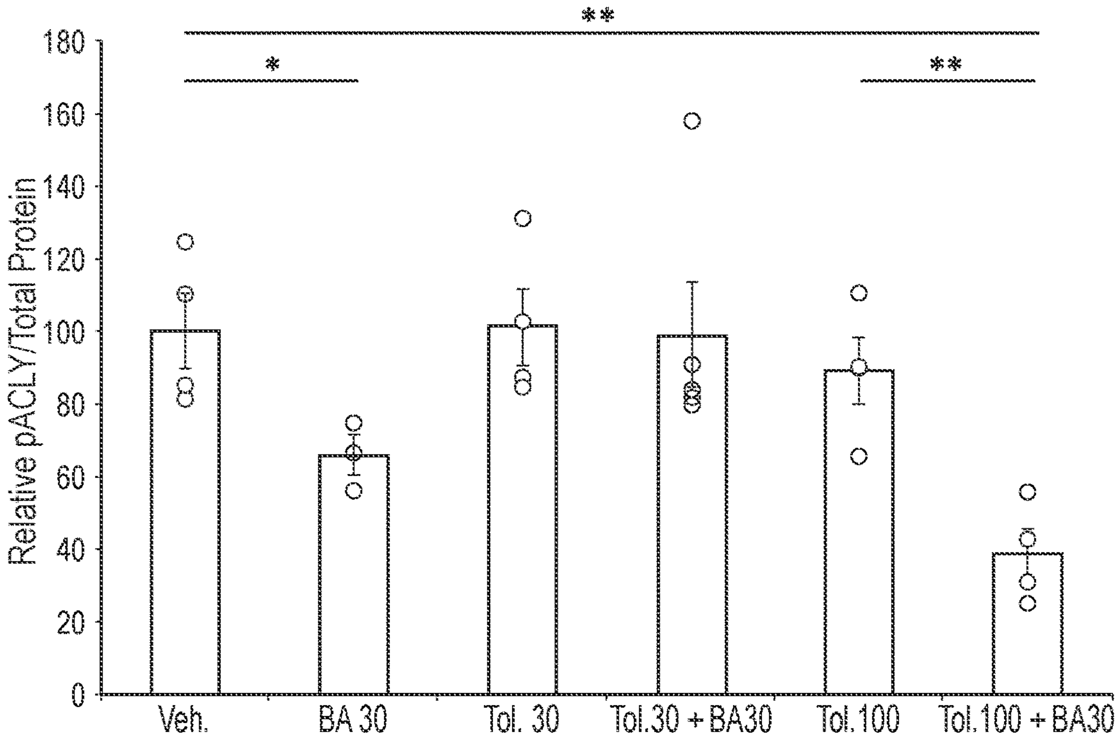
FIG. 8B is a histogram comparing the kidney lysate pACLY expression relative to total protein expression among the treatment groups described in FIGS. 3B and 3C.
Figure 9A:
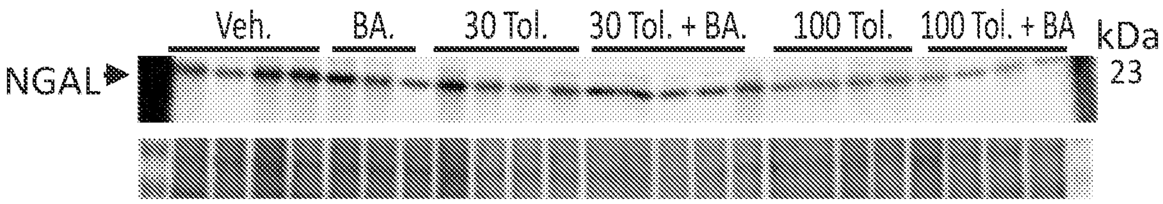
FIG. 9A is an immunoblot assay of kidney lysates from the treatment groups described in FIGS. 3B and 3C comparing the NGAL expression relative to total protein expression among the treatment groups.

At the end of the study, kidney sample lysates were prepared in buffer and separated using SDS-PAGE. Separated proteins were then electrophoretically transferred to membranes. Nonspecific binding was blocked, and membranes were probed with antibodies against phosphorylated (Thr172)-AMPK, phosphorylated P70S6K, phosphorylated ERK, phosphorylated ACLY, total KIM-1, and total neutrophil gelatinase-associated lipocalin (NGAL). Membranes were incubated with appropriate detection antibodies and relative signal intensity determined. Protein levels were normalized to total protein levels. Bempedoic acid treatment reduced ACLY (FIG. 8) and stimulated AMPK (FIG. 5A/5B) activity. Bempedoic acid also inhibited the mTOR (FIG. 6A/6B), ERK (FIG. 7), and NGAL (FIG. 9A/9B) signaling pathways, which are upregulated in ADPKD. Finally, bempedoic acid also dramatically reduced KIM-1 expression, a marker of kidney injury, by >70% (FIG. 4A/4B), and, to a lesser extent, neutrophil gelatinase-associate lipocalin (NGAL). These effects of bempedoic acid occurred both alone and in combination with tolvaptan therapy.

Figure 10A:
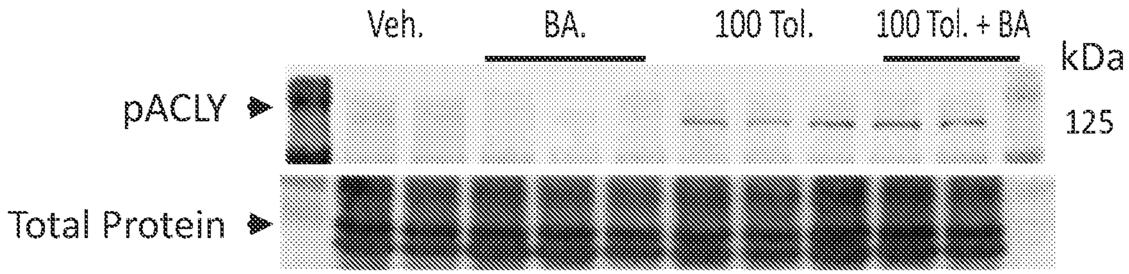
FIG. 10A is an immunoblot assay of liver lysates from the treatment groups described in FIGS. 3B and 3C receiving vehicle, bempedoic acid 30 mg/kg/d, tolvaptan 100 mg/kg/d, or tolvaptan 100 mg/kg/d+bempedoic acid 30 mg/kg/d, comparing the pACLY expression relative to total protein expression among the treatment groups.
Figure 10B:
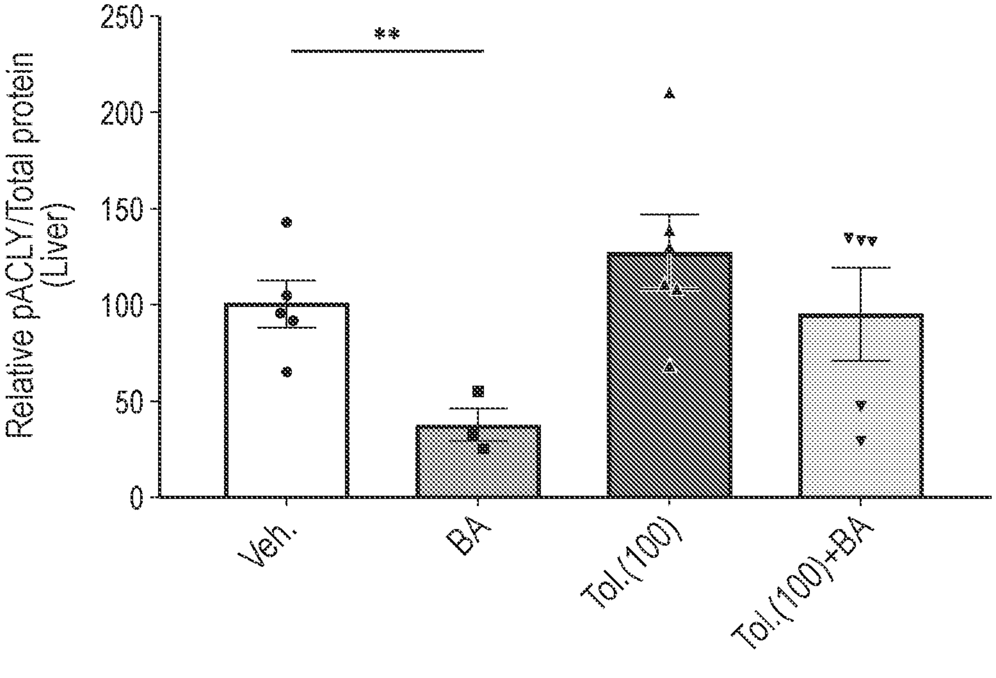
FIG. 10B is a histogram comparing the liver lysate pACLY expression relative to total protein expression among the treatment groups described in FIG. 10A.
Figure 11A:
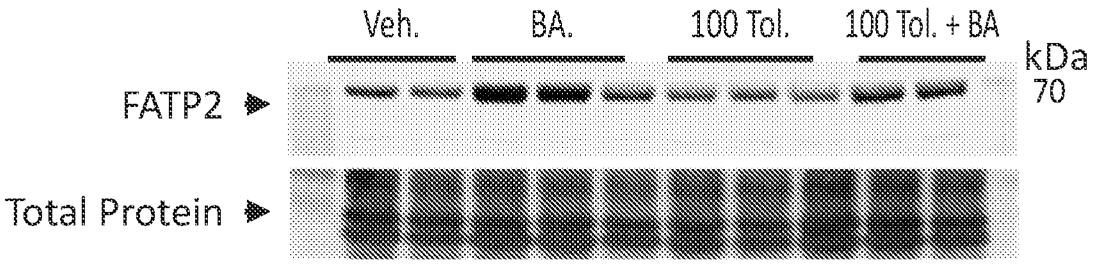
FIG. 11A is an immunoblot assay of liver lysates from the treatment groups described in FIGS. 3B and 3C receiving vehicle, bempedoic acid 30 mg/kg/d, tolvaptan 100 mg/kg/d, or tolvaptan 100 mg/kg/d+bempedoic acid 30 mg/kg/d, comparing the FATP2 expression relative to total protein expression among the treatment groups
Figure 11B:
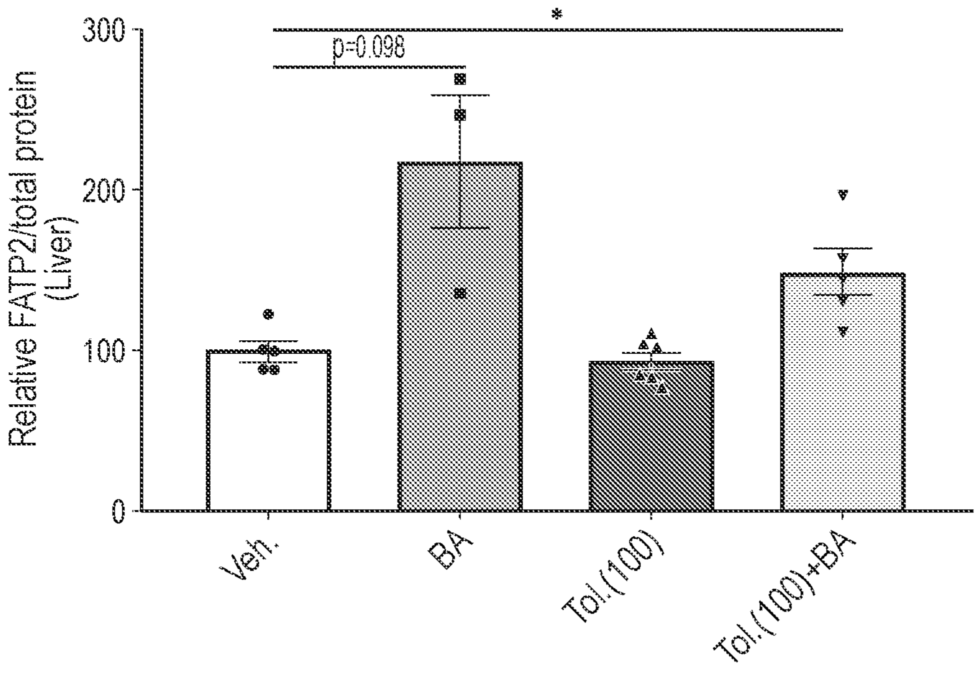
FIG. 11B is a histogram comparing the liver lysate FATP2 expression relative to total protein expression among the treatment groups described in FIG. 11A.
Figure 12A:
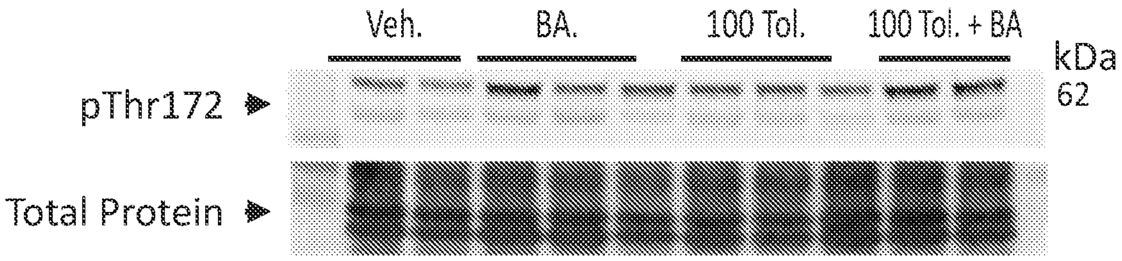
FIG. 12A is an immunoblot assay of liver lysates from the treatment groups described in FIGS. 3B and 3C receiving vehicle, bempedoic acid 30 mg/kg/d, tolvaptan 100 mg/kg/d, or tolvaptan 100 mg/kg/d+bempedoic acid 30 mg/kg/d, comparing the pThr172 expression relative to total protein expression among the treatment groups.
Figure 12B:
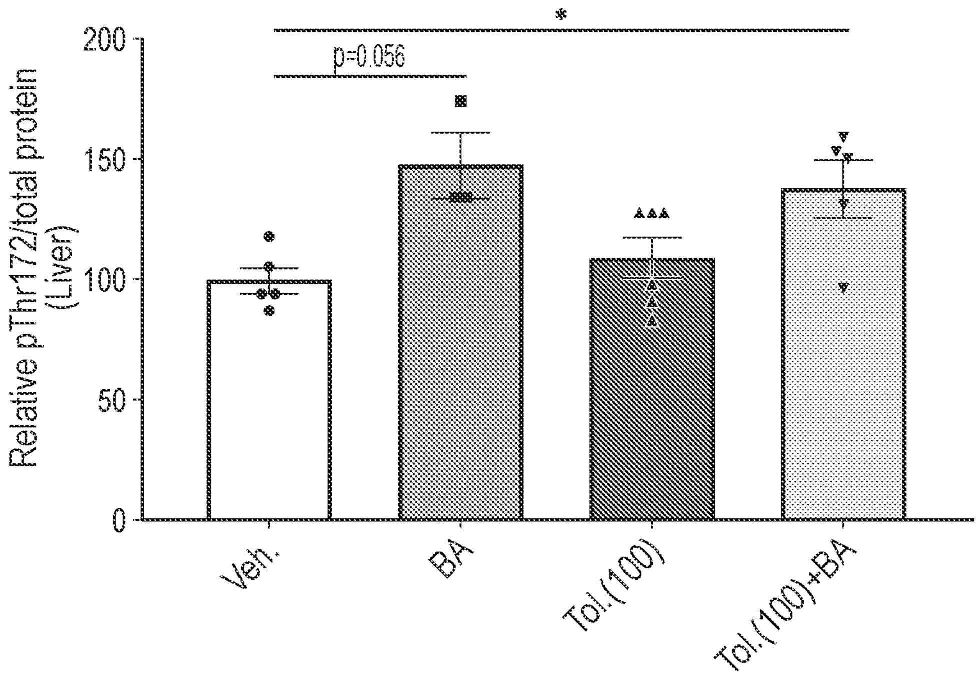
FIG. 12B is a histogram comparing the liver lysate pThr172 expression relative to total protein expression among the treatment groups described in FIG. 12A.
Figure 13A:
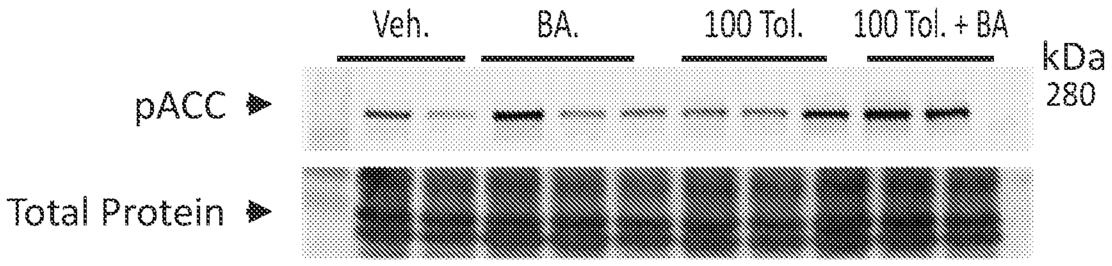
FIG. 13A is an immunoblot assay of liver lysates from the treatment groups described in FIGS. 3B and 3C receiving vehicle, bempedoic acid 30 mg/kg/d, tolvaptan 100 mg/kg/d, or tolvaptan 100 mg/kg/d+bempedoic acid 30 mg/kg/d, comparing the pACC expression relative to total protein expression among the treatment groups.
Figure 13B:
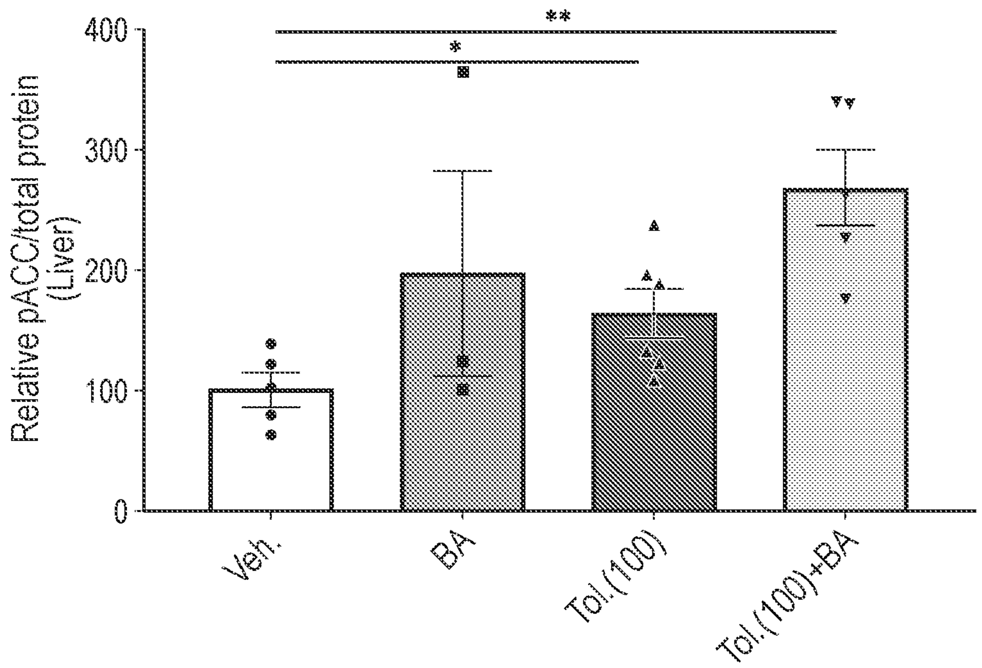
FIG. 13B is a histogram comparing the liver lysate pACC expression relative to total protein expression among the treatment groups described in FIG. 13A.
Figure 14A:
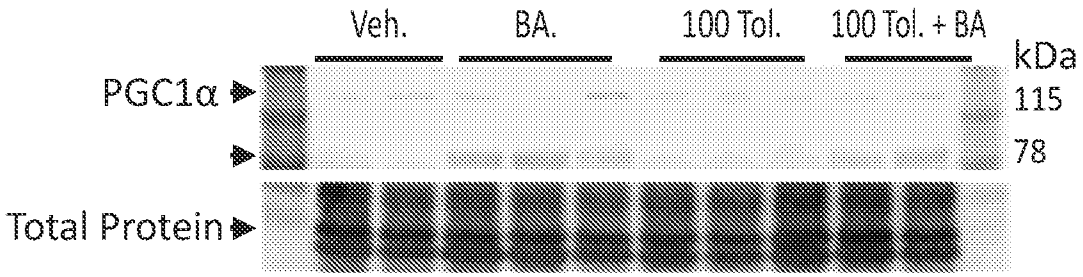
FIG. 14A is an immunoblot assay of liver lysates from the treatment groups described in FIGS. 3B and 3C receiving vehicle, bempedoic acid 30 mg/kg/d, tolvaptan 100 mg/kg/d, or tolvaptan 100 mg/kg/d+bempedoic acid 30 mg/kg/d, comparing the PGC1a expression relative to total protein expression among the treatment groups.
Figure 14B:
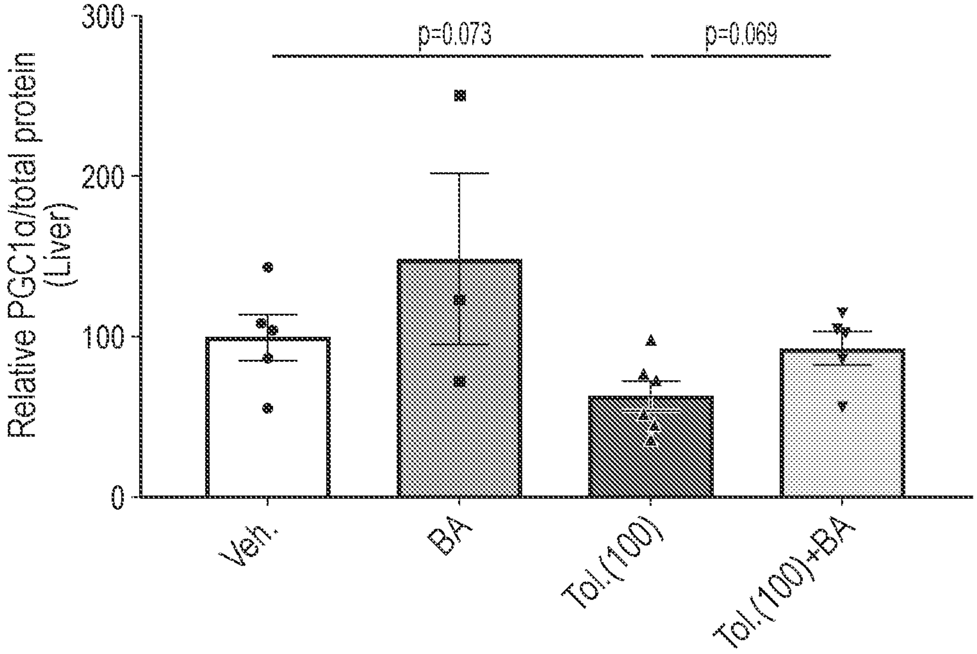
FIG. 14B is a histogram comparing the liver lysate PGC1a expression relative to total protein expression among the treatment groups described in FIG. 14A.
Figure 15A:
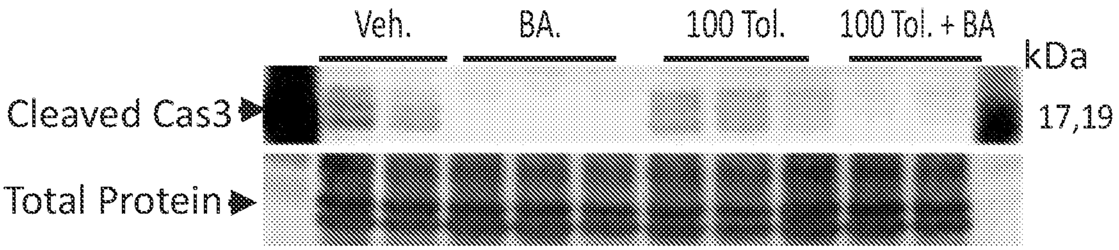
FIG. 15A is an immunoblot assay of liver lysates from the treatment groups described in FIGS. 3B and 3C receiving vehicle, bempedoic acid 30 mg/kg/d, tolvaptan 100 mg/kg/d, or tolvaptan 100 mg/kg/d+bempedoic acid 30 mg/kg/d, comparing the cleaved Cas3 expression relative to total protein expression among the treatment groups.
Figure 15B:
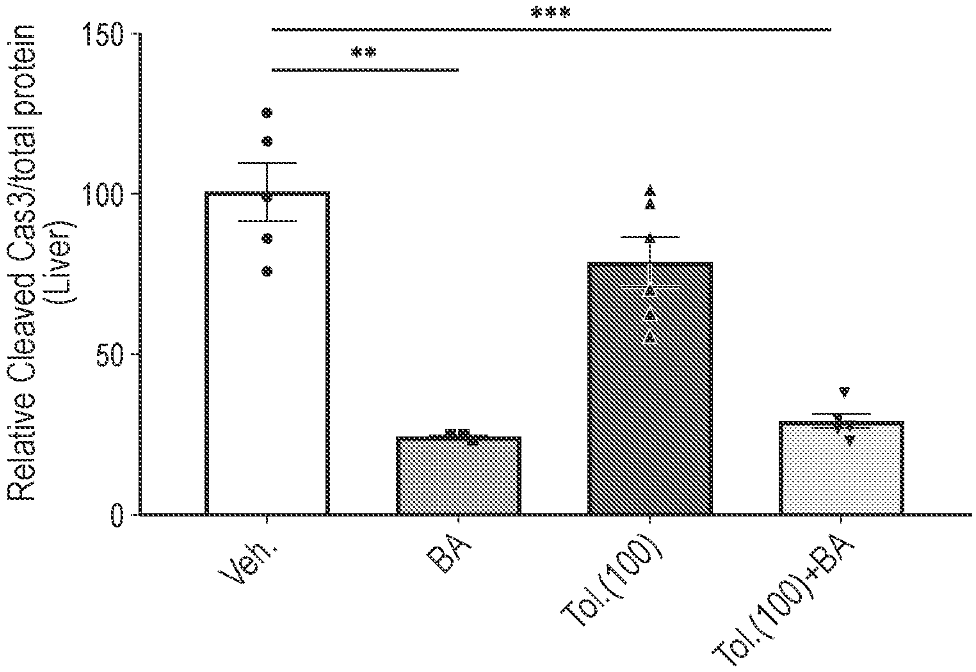
FIG. 15B is a histogram comparing the liver lysate cleaved Cas3 expression relative to total protein expression among the treatment groups described in FIG. 15A.
Figure 16:
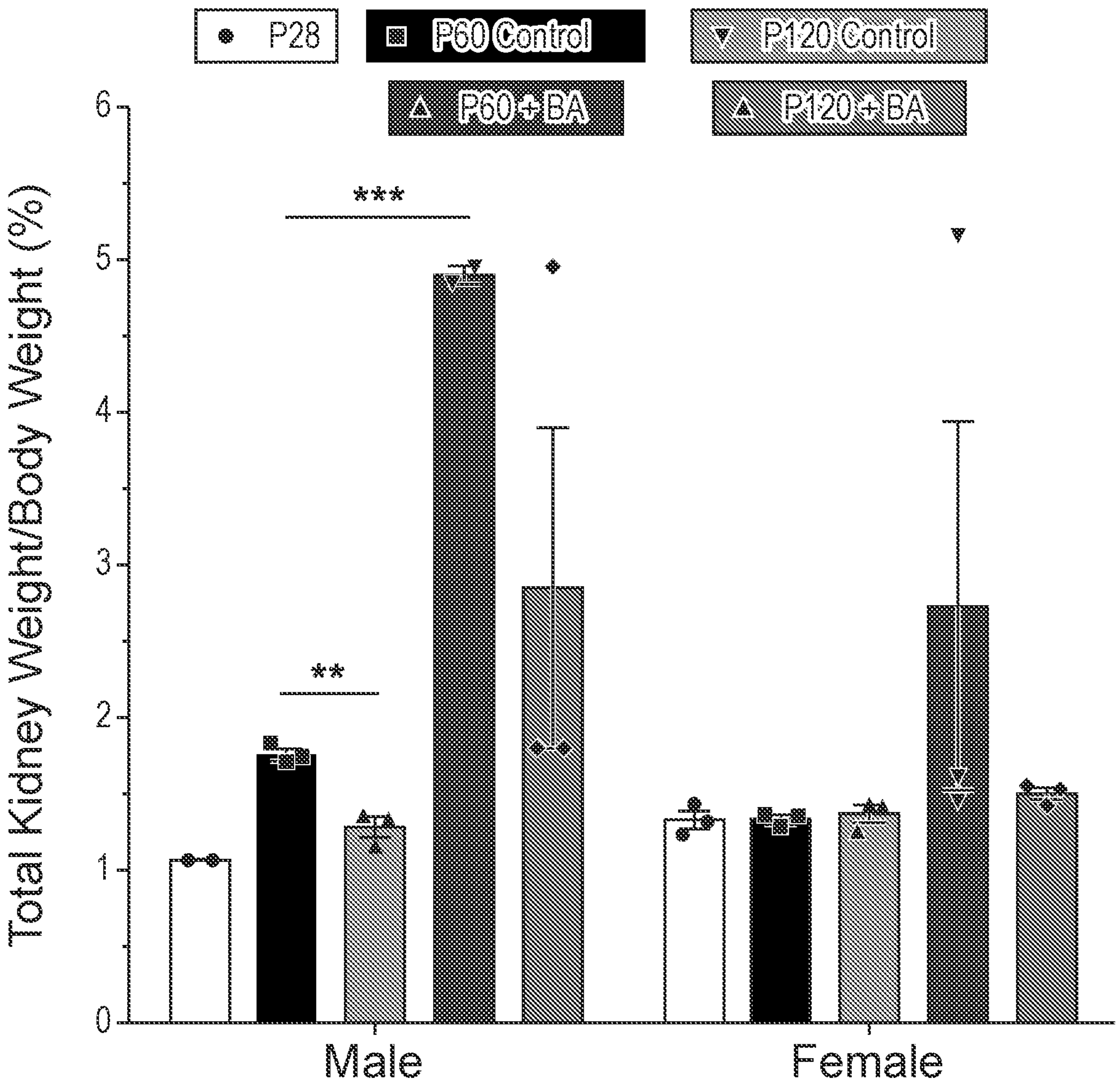
FIG. 16 is a histogram comparing the total kidney weight to body weight percent in a late onset, slowly developing ADPKD mouse model. Mice were divided into three groups. Two groups were each sacrificed at different points in time after PKD induction, both of which were divided into subgroups receiving either bempedoic acid or control. One group was sacrificed upon induction of PKD to act as a control and facilitate interpretation of the magnitude of treatment effect.

Liver sample lysates were prepared in buffer and separated using SDS-PAGE. Separated proteins were then electrophoretically transferred to membranes. Nonspecific binding was blocked and membranes were probed with antibodies against pACLY, pThr172AMPKα, PGC1alpha, FATP2, pACC, and cleaved Cas3. Membranes were incubated with appropriate detection antibodies and relative signal intensity determined. Target protein levels were normalized to total protein levels. Bempedoic acid inhibited pACLY (activation marker) (FIG. 10A/10B) and increased FATP2 expression (FIG. 11A/11B) both alone and in combination with tolvaptan. Bempedoic acid also increased AMPK activity (FIG. 12A/12B), and promoted phosphorylation of conical AMPK target ACC in liver tissue (FIG. 13A/13B).

Example 4—Studies Examining the Effects of Bempedoic Acid in a Slowly Developing Late Onset ADPKD Mouse Model The example describes characterization of the late onset, slowly developing ADPKD mouse model Pkd1fl/fl;Pax8-rtTA;Tet-On-Cre when treated with bempedoic acid.

Figure 9B:
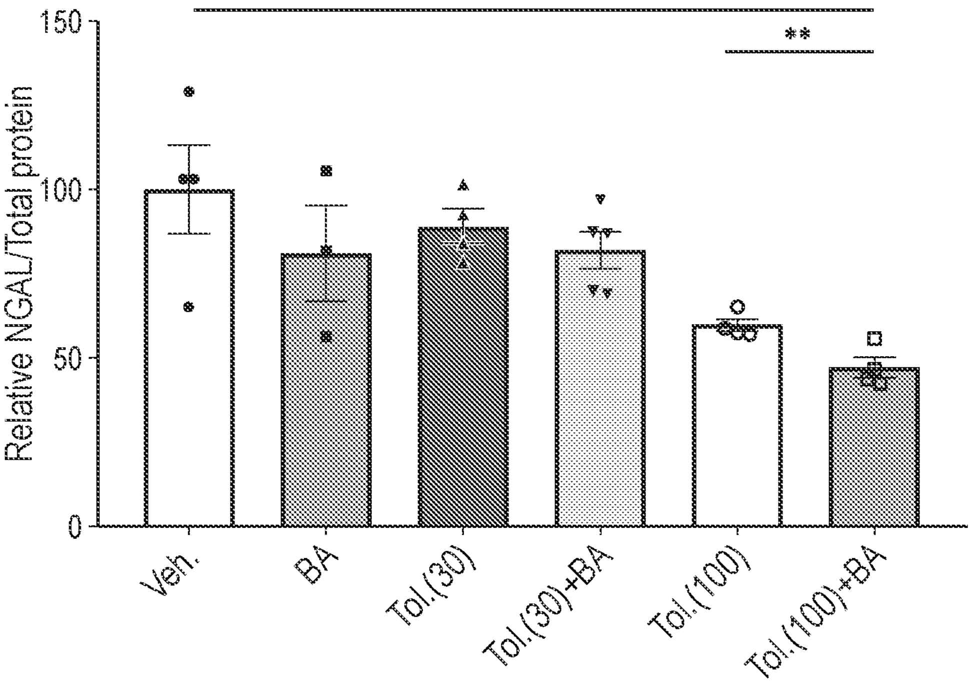
FIG. 9B is a histogram comparing the kidney lysate NGAL expression relative to total protein expression among the treatment groups described in FIGS. 3B and 3C.

Doxycycline was administered intraperitoneally (50 mg/kg/day) on postnatal days 27-29 (P27-P29) and again on P43 and P57 to induce later Pkd1 knockout and slowly progressive PKD in the Cre+ mice. Mice were then sacrificed at P28, P60, and P120 for measurements of total kidney weight to body weight ratios. The ratio was dramatically increased in male control mice at P60, and both male and female control mice at P120 compared to P28 Cre− control mice. Treatment with bempedoic acid (30 mg/kg/d, mixed with food, beginning on P30 and continuing through P60 or P120) significantly reduced total kidney weight to body weight ratio at P60 in male mice, a trend that was also observed at P120 in both male and female mice (FIG. 9).

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

We claim:

1. A fixed-dose combination comprising bempedoic acid and tolvaptan.

2. The fixed-dose combination of claim 1, wherein the fixed-dose combination comprises about 30 mg to about 240 mg bempedoic acid.

3. The fixed-dose combination of claim 1, wherein the fixed-dose combination comprises about 5 mg to about 120 mg tolvaptan, about 5 mg to about 90 mg tolvaptan, or about 5 mg to about 60 mg tolvaptan.

4. The fixed-dose combination of claim 1, wherein the fixed-dose combination comprises about 5 mg, about 10 mg, about 15 mg, about 30 mg, about 45 mg, about 60 mg, or about 90 mg tolvaptan.

5. The fixed-dose combination of claim 1, wherein the fixed-dose combination comprises about 180 mg bempedoic acid.

6. A pharmaceutical composition comprising:
bempedoic acid;
tolvaptan; and
one or more pharmaceutically acceptable excipients.

7. The pharmaceutical composition of claim 6, wherein the pharmaceutical composition comprises about 30 mg to about 240 mg bempedoic acid.

8. The pharmaceutical composition of claim 6, wherein the pharmaceutical composition comprises about 5 mg to about 120 mg tolvaptan, about 5 mg to about 90 mg tolvaptan, or about 5 mg to about 60 mg tolvaptan.

9. The pharmaceutical composition of claim 6, wherein the pharmaceutical composition comprises about 5 mg, about 10 mg, about 15 mg, about 30 mg, about 45 mg, about 60 mg, or about 90 mg tolvaptan.

10. The pharmaceutical composition of claim 6, wherein the pharmaceutical composition comprises about 180 mg bempedoic acid.

11. The pharmaceutical composition of claim 6, wherein the pharmaceutical composition is formulated for oral delivery.

12. The pharmaceutical composition of claim 11, wherein the pharmaceutical composition is formulated as an oral solid dosage form selected from the group consisting of a tablet, a capsule, a softgel capsule, a pill, a solution, and a suspension.

13. The pharmaceutical composition of claim 6, wherein the pharmaceutical composition provides immediate release of bempedoic acid.

14. The pharmaceutical composition of claim 6, wherein the pharmaceutical composition provides sustained release of bempedoic acid.

15. A method of treating autosomal dominant polycystic kidney disease (ADPKD) or slowing the progression of ADPKD in a subject in need thereof or preventing kidney failure in a subject with ADPKD, the method comprising administering to the subject an effective amount of bempedoic acid.

16. The method of claim 15, wherein the effective amount of bempedoic acid is about 30 mg to about 240 mg bempedoic acid, or about 180 mg bempedoic acid.

17. The method of claim 15, further comprising administering to the subject an effective amount of tolvaptan.

18. The method of claim 17, wherein the effective amount of tolvaptan is about 5 mg, about 10 mg, about 15 mg, about 30 mg, about 45 mg, about 60 mg, or about 90 mg tolvaptan.

19. The method of claim 15, wherein the subject receiving the effective amount of bempedoic acid has a lower composite incidence of clinical endpoints selected from worsening kidney function, kidney pain, hypertension, and albuminuria than a subject receiving a placebo, or has an equivalent or a lower composite incidence of clinical endpoints selected from worsening kidney function, kidney pain, hypertension, and albuminuria than a subject receiving tolvaptan therapy.

20. The method of claim 15, wherein the subject is a human.

* * * * *